US010006006B2

(12) United States Patent
Rezania

(10) Patent No.: US 10,006,006 B2
(45) Date of Patent: Jun. 26, 2018

(54) USE OF SMALL MOLECULES TO ENHANCE MAFA EXPRESSION IN PANCREATIC ENDOCRINE CELLS

(71) Applicant: Janssen Biotech, Inc., Horsham, PA (US)

(72) Inventor: Alireza Rezania, Raritan, NJ (US)

(73) Assignee: Janssen Biotech, Inc., Horsham, PA (US)

( * ) Notice: Subject to any disclaimer, the term of this patent is extended or adjusted under 35 U.S.C. 154(b) by 182 days.

(21) Appl. No.: 14/706,310

(22) Filed: May 7, 2015

(65) Prior Publication Data

US 2015/0329828 A1 Nov. 19, 2015

Related U.S. Application Data

(60) Provisional application No. 61/994,259, filed on May 16, 2014.

(51) Int. Cl.
*C12N 5/071* (2010.01)

(52) U.S. Cl.
CPC ...... *C12N 5/0676* (2013.01); *C12N 2501/115* (2013.01); *C12N 2501/119* (2013.01); *C12N 2501/40* (2013.01); *C12N 2501/727* (2013.01); *C12N 2501/999* (2013.01); *C12N 2506/02* (2013.01); *C12N 2506/22* (2013.01)

(58) Field of Classification Search
CPC .................................................. C12N 5/0676
See application file for complete search history.

(56) References Cited

U.S. PATENT DOCUMENTS

| | | |
|---|---|---|
| 3,209,652 A | 10/1965 | Burgsmueller |
| 3,845,641 A | 11/1974 | Waller |
| 3,935,067 A | 1/1976 | Thayer |
| 4,499,802 A | 2/1985 | Simpson |
| 4,537,773 A | 8/1985 | Shenvi |
| 4,557,264 A | 12/1985 | Hinsch |
| 4,737,578 A | 4/1988 | Evans et al. |
| 5,215,893 A | 6/1993 | Mason et al. |
| 5,449,383 A | 9/1995 | Chatelier et al. |
| 5,525,488 A | 6/1996 | Mason et al. |
| 5,567,612 A | 10/1996 | Vacanti et al. |
| 5,665,568 A | 9/1997 | Mason et al. |
| 5,686,090 A | 11/1997 | Schilder et al. |
| 5,713,957 A | 2/1998 | Steele et al. |
| 5,716,810 A | 2/1998 | Mason et al. |
| 5,718,922 A | 2/1998 | Herrero-Vanrell |
| 5,759,830 A | 6/1998 | Vacanti et al. |
| 5,770,417 A | 6/1998 | Vacanti et al. |
| 5,780,454 A | 7/1998 | Adams et al. |
| 5,834,308 A | 11/1998 | Peck et al. |
| 5,843,780 A | 12/1998 | Thomson |
| 5,888,816 A | 3/1999 | Coon et al. |
| 5,908,782 A | 6/1999 | Marshank et al. |
| 5,914,262 A | 6/1999 | MacMichael et al. |
| 5,942,435 A | 8/1999 | Wheeler |
| 6,001,647 A | 12/1999 | Peck et al. |
| 6,022,743 A | 2/2000 | Naughton et al. |
| 6,087,113 A | 6/2000 | Caplan et al. |
| 6,083,903 A | 7/2000 | Adams et al. |
| 6,200,806 B1 | 3/2001 | Thomson |
| 6,261,549 B1 | 6/2001 | Fernandez et al. |
| 6,281,012 B1 | 8/2001 | McIntosh et al. |
| 6,297,217 B1 | 10/2001 | Adams et al. |
| 6,306,424 B1 | 10/2001 | Vyakarnam et al. |
| 6,328,960 B1 | 12/2001 | McIntosh et al. |
| 6,331,298 B1 | 12/2001 | Ferguson et al. |
| 6,333,029 B1 | 12/2001 | Vyakarnam et al. |
| 6,365,149 B2 | 2/2002 | Vyakarnam et al. |
| 6,413,773 B1 | 7/2002 | Ptasznik et al. |
| 6,436,704 B1 | 8/2002 | Roberts et al. |
| 6,458,589 B1 | 10/2002 | Rambhatla |
| 6,458,593 B1 | 10/2002 | Musick et al. |
| 6,509,369 B2 | 1/2003 | Scott et al. |
| 6,521,427 B1 | 2/2003 | Evans |
| 6,534,084 B1 | 3/2003 | Vyakarnam et al. |
| 6,599,323 B2 | 7/2003 | Melican et al. |
| 6,617,152 B2 | 9/2003 | Bryhan et al. |
| 6,617,317 B1 | 9/2003 | Adams et al. |
| 6,626,950 B2 | 9/2003 | Brown et al. |
| 6,642,048 B2 | 11/2003 | Xu |
| 6,656,488 B2 | 12/2003 | Yi et al. |
| 6,670,127 B2 | 12/2003 | Evans |

(Continued)

FOREIGN PATENT DOCUMENTS

| | | |
|---|---|---|
| CN | 1389565 A | 7/2002 |
| CN | 1602351 A | 3/2005 |

(Continued)

OTHER PUBLICATIONS

Brevini et al., 2010, Theriogenology, vol. 74, pp. 544-550.*
Paris et al. (2010, Theriogenology, vol. 74, pp. 516-524).*
Munoz et al. (2008, Theriogenology, vol. 69, pp. 1159-1164).*
Gomez et al. (2010, Theriogenology, vol. 74, pp. 498-515).*
Jean et al. (2013, Develop. Growth Differ., vol. 55, pp. 41-51).*
Buta et al. (2013, Stem Cell Res., vol. 11, pp. 552-562).*
Nishimura et al. (2006, Developmental Biology, vol. 293, pp. 526-539).*
Chen, et al., A Small Molecule That Directs Differentiation of Human ESCs into the Pancreatic Lineage, Nature Chemical Biology, 2009, pp. 258-265, vol. 5, No. 4.
Fomina-Yadlin, et al., Small-Molecule Inducers of Insulin Expression in Pancreatic Cells, Proceedings of the National Academy of Sciences, 2010, pp. 15099-15104, vol. 107.

(Continued)

*Primary Examiner* — Thaian N Ton
*Assistant Examiner* — David A. Montanari
(74) *Attorney, Agent, or Firm* — Lois A. Gianneschi

(57) ABSTRACT

The present invention provides methods, cell cultures and differentiation media to promote differentiation of pluripotent stem cells to pancreatic endocrine cells of a mature phenotype. The resulting pancreatic endocrine cells express single hormonal insulin, PDX1, NKX6.1, and MAFA. In one or more differentiation stages, culturing may be carried out in a culture vessel at the air-liquid interface.

20 Claims, 22 Drawing Sheets

(56) References Cited

U.S. PATENT DOCUMENTS

| | | |
|---|---|---|
| 6,703,017 B1 | 3/2004 | Peck et al. |
| 6,713,446 B2 | 3/2004 | Gupta |
| 6,793,945 B2 | 9/2004 | Bathurst et al. |
| 6,800,480 B1 | 10/2004 | Bodnar et al. |
| 6,815,203 B1 | 11/2004 | Bonner-Weir et al. |
| 6,958,319 B2 | 10/2005 | Gupta |
| 6,987,110 B2 | 1/2006 | Zhang et al. |
| 7,005,252 B1 | 2/2006 | Thomson et al. |
| 7,033,831 B2 | 4/2006 | Fisk et al. |
| 7,157,275 B2 | 1/2007 | Guarino et al. |
| 7,297,539 B2 | 11/2007 | Mandalam et al. |
| 7,326,572 B2 | 2/2008 | Fisk et al. |
| 7,371,576 B2 | 5/2008 | Tsang et al. |
| 7,410,798 B2 | 8/2008 | Mandalam et al. |
| 7,413,734 B2 | 8/2008 | Mistry et al. |
| 7,442,548 B2 | 10/2008 | Thomson et al. |
| 7,449,334 B2 | 11/2008 | Thomsom et al. |
| 7,510,873 B2 | 3/2009 | Mistry et al. |
| 7,510,876 B2 | 3/2009 | D'Amour et al. |
| 7,534,608 B2 | 5/2009 | Martinson et al. |
| 7,569,385 B2 | 8/2009 | Haas |
| 7,585,672 B2 | 9/2009 | Odorico et al. |
| 7,704,738 B2 | 4/2010 | D'Amour et al. |
| 7,993,920 B2 | 8/2011 | Martinson et al. |
| 8,187,878 B2 | 5/2012 | Dalton et al. |
| 8,859,286 B2 | 10/2014 | Agulnick |
| 9,234,178 B2 * | 1/2016 | Rezania ............... C12N 5/0676 |
| 2002/0072117 A1 | 7/2002 | Xu |
| 2003/0082155 A1 | 5/2003 | Habener |
| 2003/0138948 A1 | 7/2003 | Fisk et al. |
| 2003/0180903 A1 | 9/2003 | Bryhan et al. |
| 2004/0015805 A1 | 1/2004 | Kidd |
| 2004/0058412 A1 | 3/2004 | Ho et al. |
| 2004/0062753 A1 | 4/2004 | Rezania |
| 2004/0106196 A1 | 6/2004 | Fraser et al. |
| 2004/0121460 A1 | 6/2004 | Lumelsky et al. |
| 2004/0121461 A1 | 6/2004 | Honmou et al. |
| 2004/0132729 A1 | 7/2004 | Salituro et al. |
| 2004/0161419 A1 | 8/2004 | Strom et al. |
| 2004/0171623 A1 | 9/2004 | Reynolds et al. |
| 2004/0209901 A1 | 10/2004 | Adams et al. |
| 2004/0220393 A1 | 11/2004 | Ward et al. |
| 2004/0241761 A1 | 12/2004 | Sarvetnick |
| 2005/0037491 A1 | 2/2005 | Mistry et al. |
| 2005/0053588 A1 | 3/2005 | Yin et al. |
| 2005/0054093 A1 | 3/2005 | Haas |
| 2005/0054098 A1 | 3/2005 | Mistry et al. |
| 2005/0054102 A1 | 3/2005 | Wobus et al. |
| 2005/0058631 A1 | 3/2005 | Kihm et al. |
| 2005/0063961 A1 | 3/2005 | Friedlander et al. |
| 2005/0148070 A1 | 7/2005 | Thomson et al. |
| 2005/0158852 A1 | 7/2005 | D'Amour et al. |
| 2005/0187298 A1 | 8/2005 | Vasudevan et al. |
| 2005/0037488 A1 | 9/2005 | Mitalipova |
| 2005/0208029 A1 | 9/2005 | Umezawa et al. |
| 2005/0233446 A1 | 10/2005 | Parsons |
| 2005/0244962 A1 | 11/2005 | Thomson et al. |
| 2005/0260749 A1 | 11/2005 | Odorico et al. |
| 2005/0266554 A1 | 12/2005 | D'Amour |
| 2006/0003446 A1 | 1/2006 | Keller |
| 2006/0030042 A1 | 2/2006 | Brivaniou et al. |
| 2006/0040387 A1 | 2/2006 | Fisk |
| 2006/0148081 A1 | 7/2006 | Kelly et al. |
| 2006/0194315 A1 | 8/2006 | Condie et al. |
| 2006/0194321 A1 | 8/2006 | Colman et al. |
| 2006/0281174 A1 | 12/2006 | Xu et al. |
| 2007/0010011 A1 | 1/2007 | Parsons |
| 2007/0082397 A1 | 4/2007 | Hasson et al. |
| 2007/0122903 A1 | 5/2007 | Rezania et al. |
| 2007/0122905 A1 | 5/2007 | D'Amour et al. |
| 2007/0154981 A1 | 7/2007 | Hori et al. |
| 2007/0155013 A1 | 7/2007 | Akaike et al. |
| 2007/0155661 A1 | 7/2007 | Kim |
| 2007/0254359 A1 | 11/2007 | Rezania |
| 2007/0259421 A1 | 11/2007 | D'Amour et al. |
| 2007/0259423 A1 | 11/2007 | Odorico |
| 2007/0264713 A1 | 11/2007 | Terstegge et al. |
| 2008/0091234 A1 | 4/2008 | Kladakis et al. |
| 2008/0159994 A1 | 7/2008 | Mantalaris et al. |
| 2008/0241107 A1 | 10/2008 | Copland, III et al. |
| 2008/0260700 A1 | 10/2008 | Accili et al. |
| 2008/0267926 A1 | 10/2008 | Martinson et al. |
| 2008/0268533 A1 | 10/2008 | Dalton et al. |
| 2008/0268534 A1 | 10/2008 | Robins et al. |
| 2009/0004152 A1 | 1/2009 | Martinson et al. |
| 2009/0029462 A1 | 1/2009 | Beardsley et al. |
| 2009/0053182 A1 | 2/2009 | Ichim et al. |
| 2009/0093055 A1 | 4/2009 | Fisk et al. |
| 2009/0170198 A1 | 7/2009 | Rezania |
| 2009/0203141 A1 | 8/2009 | Lin et al. |
| 2009/0263896 A1 | 10/2009 | Kelly et al. |
| 2009/0269845 A1 | 10/2009 | Rezania et al. |
| 2009/0298178 A1 | 12/2009 | D'Amour |
| 2009/0325293 A1 | 12/2009 | Davis et al. |
| 2010/0003749 A1 | 1/2010 | Uchida et al. |
| 2010/0015100 A1 | 1/2010 | Xu |
| 2010/0015711 A1 | 1/2010 | Davis et al. |
| 2010/0028307 A1 | 2/2010 | O'Neil |
| 2010/0093053 A1 | 4/2010 | Oh et al. |
| 2010/0112691 A1 | 5/2010 | Green et al. |
| 2010/0112693 A1 | 5/2010 | Rezania et al. |
| 2010/0255580 A1 | 10/2010 | Rezania |
| 2011/0014703 A1 | 1/2011 | Xu et al. |
| 2011/0104805 A1 | 5/2011 | Fung et al. |
| 2011/0151560 A1 | 6/2011 | Xu |
| 2011/0151561 A1 | 6/2011 | Davis |
| 2011/0229441 A1 | 9/2011 | Benchoua et al. |
| 2011/0281355 A1 | 11/2011 | Xu |
| 2012/0045830 A1 | 2/2012 | Green et al. |
| 2012/0052576 A1 | 3/2012 | Rezania |
| 2012/0190111 A1 | 7/2012 | Davis et al. |
| 2012/0264209 A1 | 10/2012 | Odorico et al. |
| 2013/0189777 A1 | 7/2013 | Rezania |
| 2013/0224156 A1 | 8/2013 | Takahashi et al. |

FOREIGN PATENT DOCUMENTS

| | | |
|---|---|---|
| CN | 1671835 A | 9/2005 |
| CN | 1946838 A | 4/2007 |
| CN | 101092606 A | 12/2007 |
| CN | 101310012 A | 11/2008 |
| CN | 101410509 A | 4/2009 |
| CN | 101541953 A | 9/2009 |
| CN | 101611016 A | 12/2009 |
| EP | 0363125 A2 | 4/1990 |
| EP | 348969 B1 | 5/1993 |
| EP | 0617126 B1 | 9/1994 |
| EP | 0800829 B1 | 10/1997 |
| EP | 0092302 B1 | 11/2006 |
| EP | 1873237 A1 | 1/2008 |
| EP | 1391505 B1 | 1/2009 |
| EP | 2088190 A1 | 8/2009 |
| EP | 2 604 685 A1 | 6/2013 |
| EP | 2479260 B1 | 6/2016 |
| GB | 2484873 B2 | 4/2014 |
| JP | 2005506074 A2 | 3/2003 |
| JP | 2006-500003 A2 | 1/2006 |
| JP | 2008500809 A2 | 1/2008 |
| JP | 2009513143 A2 | 4/2009 |
| KR | 10-2008-0020098 A | 3/2008 |
| RU | 2359671 C2 | 6/2009 |
| WO | WO199219759 A2 | 2/1992 |
| WO | 199847892 A1 | 10/1998 |
| WO | WO199920741 A1 | 4/1999 |
| WO | 200029549 A1 | 5/2000 |
| WO | 200123528 A1 | 4/2001 |
| WO | WO200151616 A2 | 7/2001 |
| WO | WO200181549 A3 | 11/2001 |
| WO | 200246183 A2 | 6/2002 |
| WO | 200246197 A1 | 6/2002 |
| WO | 2002086107 A2 | 10/2002 |
| WO | 02092756 A2 | 11/2002 |
| WO | 03033697 A1 | 4/2003 |
| WO | 2003026584 A2 | 4/2003 |

(56) References Cited

FOREIGN PATENT DOCUMENTS

| | | |
|---|---|---|
| WO | 2003029445 A1 | 4/2003 |
| WO | 2003042405 A2 | 5/2003 |
| WO | WO200305049 A1 | 6/2003 |
| WO | 2003054169 A1 | 7/2003 |
| WO | 2003062405 A2 | 7/2003 |
| WO | 2003095452 A1 | 11/2003 |
| WO | 03103972 A1 | 12/2003 |
| WO | WO2003102134 A2 | 12/2003 |
| WO | 2004016747 A2 | 2/2004 |
| WO | WO2004011621 A2 | 2/2004 |
| WO | 2004044158 | 5/2004 |
| WO | 2004050827 A2 | 6/2004 |
| WO | 2004055155 A2 | 7/2004 |
| WO | 2004073633 A1 | 9/2004 |
| WO | 2004087885 | 10/2004 |
| WO | WO2004090110 A2 | 10/2004 |
| WO | 2004067001 A1 | 12/2004 |
| WO | 2005080598 A1 | 1/2005 |
| WO | WO2005001077 A2 | 1/2005 |
| WO | 2005017117 A2 | 2/2005 |
| WO | WO2005014799 A1 | 2/2005 |
| WO | 2005058301 A1 | 6/2005 |
| WO | 2005063971 A1 | 7/2005 |
| WO | 2005065354 A2 | 7/2005 |
| WO | 2005080551 A2 | 9/2005 |
| WO | 2005086845 A2 | 9/2005 |
| WO | 2005097977 A2 | 10/2005 |
| WO | 2005097980 A2 | 10/2005 |
| WO | WO2005116073 A3 | 12/2005 |
| WO | 2006020919 A2 | 2/2006 |
| WO | WO2006016999 A1 | 2/2006 |
| WO | 2006026473 A1 | 3/2006 |
| WO | 2006029197 A1 | 3/2006 |
| WO | 2006036925 A1 | 4/2006 |
| WO | 2006080952 A2 | 8/2006 |
| WO | 2006083782 A2 | 8/2006 |
| WO | 2006100490 A1 | 9/2006 |
| WO | WO2006094286 A2 | 9/2006 |
| WO | 2006108361 A1 | 10/2006 |
| WO | 2006113470 A2 | 10/2006 |
| WO | 2006114098 A2 | 11/2006 |
| WO | 2006135824 A1 | 12/2006 |
| WO | 2006137787 A1 | 12/2006 |
| WO | 2006138433 A2 | 12/2006 |
| WO | 2007002086 A2 | 1/2007 |
| WO | 2007003525 A2 | 1/2007 |
| WO | 2007012144 A1 | 2/2007 |
| WO | 2007016485 A2 | 2/2007 |
| WO | 2007026353 A2 | 3/2007 |
| WO | 2007030870 A1 | 3/2007 |
| WO | WO2007027157 A1 | 3/2007 |
| WO | 2007047509 A1 | 4/2007 |
| WO | 2007051038 A2 | 5/2007 |
| WO | 2007069666 A1 | 6/2007 |
| WO | WO2007082963 A1 | 7/2007 |
| WO | 2007101130 A2 | 9/2007 |
| WO | WO2007103282 A1 | 9/2007 |
| WO | 2007127927 A2 | 11/2007 |
| WO | 2007143193 A1 | 12/2007 |
| WO | 2007149182 A2 | 12/2007 |
| WO | WO2007139929 A2 | 12/2007 |
| WO | 2008004990 A2 | 1/2008 |
| WO | 2008013664 A1 | 1/2008 |
| WO | 2008015682 A2 | 2/2008 |
| WO | 2008035110 A1 | 3/2008 |
| WO | 2008036447 A2 | 3/2008 |
| WO | 2008048671 A1 | 4/2008 |
| WO | WO2008048647 A1 | 4/2008 |
| WO | 2009096049 A1 | 5/2008 |
| WO | 2008086005 A1 | 7/2008 |
| WO | 2008094597 | 8/2008 |
| WO | 2008102118 A1 | 8/2008 |
| WO | 2009012428 A1 | 1/2009 |
| WO | 2009018453 A1 | 2/2009 |
| WO | 2009027644 A2 | 3/2009 |
| WO | WO2009048675 A1 | 4/2009 |
| WO | 2009061442 A1 | 5/2009 |
| WO | 2009070592 A1 | 6/2009 |
| WO | 2009096902 A1 | 8/2009 |
| WO | 2009101407 A2 | 8/2009 |
| WO | WO2009105570 A2 | 8/2009 |
| WO | 2009110215 A1 | 9/2009 |
| WO | 2009131568 A1 | 10/2009 |
| WO | 2009132083 A2 | 10/2009 |
| WO | 2009154606 A1 | 12/2009 |
| WO | 2010000415 A1 | 1/2010 |
| WO | 2010002846 A1 | 1/2010 |
| WO | 2010051213 A1 | 5/2010 |
| WO | 2010053472 A1 | 5/2010 |
| WO | 2010057039 A2 | 5/2010 |
| WO | 2010059775 A1 | 5/2010 |
| WO | WO 2010/051223 A1 | 5/2010 |
| WO | 2011011300 A2 | 1/2011 |
| WO | 2011067465 A1 | 6/2011 |
| WO | 2011108993 A1 | 9/2011 |
| WO | 2011123572 A1 | 10/2011 |
| WO | 2011139628 A1 | 11/2011 |
| WO | 2012019122 A2 | 2/2012 |
| WO | 2012117333 A1 | 9/2012 |
| WO | 2013055834 A2 | 4/2013 |
| WO | WO 2013/055397 A1 | 4/2013 |
| WO | WO 2013/095953 A1 | 6/2013 |
| WO | 2013184888 A1 | 12/2013 |
| WO | WO 2014/033322 A1 | 3/2014 |
| WO | WO 2014/105546 A1 | 7/2014 |
| WO | 2014152321 A1 | 9/2014 |

OTHER PUBLICATIONS

Kunisada, et al., Small Molecules Induce Efficient Differentiation Into Insulin-Producing Cells from Human Induced Pluripotent . . . , Stem Cell Res., 2012, pp. 272-284, vol. 8.

Buta, et al., Reconsidering pluripotency tests: Do we still need teratoma assays?, Stem Cell Research, Mar. 26, 2013, pp. 552-562, vol. 11.

Chen, et al., Retinoic acid signaling is essential for pancreas development and promotes endocrine at the expense of exocrine cell differentiation in Xenopus, Developmental Biology, May 4, 2004, pp. 144-160, vol. 271.

Cirulli, et al., Netrins: beyond the brain, Molecular Cell Biology, Apr. 2007, pp. 296-306, vol. 8.

Furue, et al., Heparin promotes the growth of human embryonic stem cells in a defined serum-free medium, PNAS, Sep. 9, 2008, pp. 13409-13414, vol. 105 Issue 36.

Gibco, Insulin-Transferin-Selenium-X 100X, Invitrogen Cell Culture, Apr. 2005, pp. 1, Form No. 3032.

Gomez, et al., Derivation of cat embryonic stem-like cells from in vitro-produced blastocysts on homologous and heterologous feeder cells, Theriogenology, May 11, 2010, pp. 498-515, vol. 74.

Gordon Weir., Do stem cells hold the key to a future cure for diabetes?, DiabetesVoice, Jun. 2008, pp. 29-31, vol. 53 Issue 2.

Jean, et al., Pluripotent genes in avian stem cells, Development Growth & Differentitaion, 2013, pp. 41-51, vol. 55.

Kang, et al., Plasma treatment of textiles—Synthetic Polymer-Based Textiles, AATCC Review, 2004, pp. 29-33, Page number.

McMahon, et al., Noggin-mediated antagonsim of BMP signaling is required for growth and patterning of the neural tube and somite, Genes & Development, Mar. 16, 1998, pp. 1438-1452, vol. 12.

Nakase, et al., Myeliod Antigen, CD13, CD14, and/ or CD33 Expression Is Restricted to Certain Lymphiod Neoplasms, Hematopathology, Jun. 1996, pp. 761-768, vol. 105 Issue 6.

Quziel-Yahalom, et al., Expansion and redifferentiation of adult human pancreatic islet cells, Biochemical and Biophysical Research Communications, Jan. 19, 2006, pp. 291-298, vol. 341.

Ramiya, et al., Reversal of insulin-dependent diabetes using islets generated in vitro from pancreatic stem cells, Nature Medicine, Mar. 2000, pp. 278-282, vol. 6 Issue 3.

Rother, et al., Challenges facing islet transplantation for the treatment of type 1 diabetes mellitus, The Journal of Clinical Investigation, 2004, pp. 877-883, vol. 114 Issue 7.

(56) References Cited

OTHER PUBLICATIONS

Rowely, et al., Meeting Lot-size Challenges of Manufacturing Adherent Cells for Therapy, Bio Process International, Mar. 2012, pp. 16-22, vol. 10 Issue 3.
Strizzi, et al., Netrin-1 regulates invasion and migration of mouse mammary epithelial cells overexpressing Cripto-1 in vitro and in vivo, Journal of Cell Science, Jul. 7, 2005, pp. 4633-4643, vol. 118 Issue 20.
Suzuken., Differentiation of Multifunctional Stem Cells Using Human Feeder Cells, Research Papers of the Suzuken Memorial Foundation, 2007, pp. 193-197, vol. 2.
Yang JW, et al., Evaluation of human MSCs cell cycle, viability and differentiation in micromass culture, Bioheology, 2006, pp. 1-2, vol. 43 Issue (3-4).
Yim,et al., Proliferation and differentiation of human embryonic germ cell derivatives in bioactive polymeric fibrous scaffold, J.Biomater.Sci.Polymer Edn,, Jan. 19, 2005, pp. 1193-1217, vol. 16 Issue 10.
Zulewski, et al., Multipotentital Nestin-Positive Stem Cells Iasolated From Adult Pancreatic Islets Differentiate Ex Vivo Into Pancreatic Endocrine, Exocrine, and Hepatic Phenotypes, Diabetes, 2001, pp. 521-533, vol. 50.
Abe, et al., Evidence That P13K, Rac, Rho, and Rho Kinase Are Involved in Basic Fibroblast Growth Factor-Stimulated Fibroblast-Collagen Matrix Contraction, Journal of Cellular Biochemistry, 2007, pp. 1290-1299, vol. 102.
Abeyta, et al., Unique Gene Expression Signatures of Independently-Derived Human Embryonic Stem Cells Lines, Human Molecular Genetics, Jan. 28, 2004, pp. 601-608, vol. 13, No. 6, Oxford University Press.
Abranches, et al., Expansion of Mouse Embryonic Stem Cells on Microcarriers, Biotechnology Bioengineering, Apr. 15, 2007, pp. 1211-1221, vol. 96, No. 6, Wiley InterScience.
Ackermann, et al., Molecular Regulation of Pancreatic B-Cell Mass Development, Maintenance, and Expansion, Journal of Molecular Endocrinology, 2007, pp. 193-206, vol. 38.
Adams, et al., Proteasome Inhibition in Cancer: Development of PS-341, Seminars in Oncology, 2001, pp. 613-619, vol. 28, No. 6.
Age-Related Eye Disease Study Research Group, A Randomized, Palcebo-Controlled, Clinical Trial of High-Dose Supplementation with Vitamins C and E, Beta Carotene, and Zinc for Age-Related Macular Degeneration and Vision Loss, Arch Ophthalmology, 2001, pp. 1417-1436, AREDS Report No. 8, vol. 119.
Ali, et al., Exploitation of Protein Kinase C: A Useful Target for Cancer Therapy, Cancer Treatment Reviews, 2009, pp. 1-8, vol. 35.
Allegrucci, et al., Differences between Human Embryonic Stem Cell Lines, Human Reproduction Update, Aug. 26, 2006, pp. 1-18, Advance Access.
Almond, et al., The Proteasome: A Novel Target for Cancer Chemotherapy, Leukemia, 2002, pp. 433-443, vol. 16.
Amit et al., Human Feeder Layers for Human Embryonic Stem Cells, Biology of Reproduction, Jan. 22, 2003, 2150-2156, 68, No. 6, Society for the Study of Reproduction, Inc.
Amit, et al., Clonally Derived Human Embryonic Stem Cell Lines Maintain Pluripotency and Proliferative Potential for Prolonged Periods of Culture, Developmental Biology, 2000, pp. 271-278, vol. 227.
Amit, et al., Dynamic Suspension Culture for Scalable Expansion of Undifferentiated Human Pluripotent Stem Cells, Nature Protocols, Apr. 7, 2011, pp. 572-579, vol. 6, No. 5.
Amit, et al., Feeder Layer- and Serum-Free Culture of Human Embryonic Stem Cells, Biology of Reproduction, 2004, pp. 837-845, vol. 70.
Arai, et al., Purification of Recombinant Activin A Using the Second Follistatin Domain of Follistatin-Related Gene (FLRG), Protein Expression & Purification, 2006, pp. 78-82, vol. 49.
Armstrong, et al., The Role of P13K/AKT, MAPK/ERK and NFκβ Signalling in the Maintenance of Human Embryonic Stem Cell Pluripotency and Viability Highlighted by Transcriptional Profiling and Functional Analysis, Human Molecular Genetics, 2006, pp. 1894-1913, vol. 15, No. 11.
Assady, et al., Insulin Production by Human Embryonic Stem Cells, Diabetes, 2001, pp. 1691-1697, vol. 50.
Baertschiger, et al., Mesenchymal Stem Cells Derived From Human Exocrine Pancrea Express Transcription Factors Implicated in Beta-Cell Development, Pancreas, 2008, pp. 75-84, vol. 37, No. 1.
Baetge, Production of B-Cells from Human Embryonic Stem Cells, Diabetes, Obesity, Metabolism, 2008, pp. 186-194, vol. 10, Supplement 4.
Bai, et al., Glucagon-Like Peptide-1 Enhances Production of Insulin in Insulin-Producing cells Derived from Mouse Embryonic Stem Cells, Journal of Endocrinology, 2005, pp. 343-352, vol. 186, No. 2.
Balsam, et al., Haematopoeitic Stem Cells Adopt Mature Haeatopoietic Fates in Ischaemic Myocardium, Nature, Apr. 8, 2004, pp. 668-673, ?, Nature Publishing Group.
Bandyopadhyay, et al., Inhibition of Pulmonary and Skeletal Metastasis by a Transforming Growth Factor-B Type I Receptor Kinase Inhibitor, Cancer Research, 2006, pp. 6714-6721, vol. 66, No. 13.
Barclay, et al., The Leucocyte Antigen Facts Book, The Leucocyte Antigen Facts Book, 1997, Textbook, 2[sup] edition, Academic Press.
Bellinger, et al., Swine Models of Type 2 Diabetes Mellitus: Insulin Resistance, Glucose Tolerance, and Cardiovascular Complications, ILAR Journal, 2006, pp. 243-258, vol. 47, No. 3.
Beltrami, et al., Adult Cardiac Stem Cells are Multipotent and Support Myocardial Regeneration, Cell, Sep. 19, 2003, pp. 763-776, vol. 114, Cell Press.
Best, et al., Embryonic Stem Cells to Beta-Cells by Understanding Pancreas Development, Molecular and Cellular Endorinology, 2008, pp. 86-94, vol. 288.
Bigdeli, et al., Adaptation of Human Embryonic Stem Cells to Feeder-Free and Matrix-Free Culture Conditions Directly on Plastic Surfaces, Journal of Biotechnology, 2008, pp. 146-153, vol. 133.
Blin, et al., A Purified Population of Multipotent Cardiovascular Progenitors Derived from Primate Pluripotent Stem Cells Engrafts in Postmyocardial Infarcted Nonhumans Primates, The Journal of Clinical Investigation, Apr. 2010, pp. 1125-1139, vol. 120, No. 4.
Blyszczuk et al., Expression of Pax4 in embryonic stem cells promotes differentiation of nestin-positive progenitor and insulin-producing cells, Proceedings of the National Academy of Sciences, Feb. 4, 2003, 998-1003, 100-3, National Academy of Sciences.
Bo, et al., Research Progress of Pancreatic Islet Development and Pancreatic Stem Cells, Journal of Clinical Surgery, 2009, pp. 208-210, vol. 17, No. 3.
Bocian-Sobkowska, et al., Polyhormonal Aspect of the Endocrine Cells of the Human Fetal Pancreas, Histochem Cell Biol, 1999, pp. 147-153, vol. 112, Issue 2.
Bonner-Weir et al., In vitro cultivation of human islets from expanded ductal tissue, Proceedings of the National Academy of Sciences, Jul. 5, 2000, 7999-8004, 97-14, National Academy of Sciences.
Borowiak, et al., How to Make AB Cells, Current Opinion Cell Biology, 2009, pp. 727-732, vol. 21, Issue 6.
Borowitz, et al., Prognostic Significance of Fluorescence Intensity of Surface Marker . . . , Blood, Jun. 1, 1997, 3960-3966, 89-11, American Society of Hematology, Washington, D.C., US.
Braam, et al., Improved Genetic Manipulation of Human Embryonic Stem Cells, Nature Methods, May 2008, pp. 389-392, vol. 5, No. 5.
Brakenhoff et al., Development of a Human Interleukin-6 Receptor Antagonist, Journal of Biological Chemistry, Jan. 7, 1994, 86-93, 269-1, US.
Brambrink, et al., Sequential Expression of Pluripotency Markers During Direct Reprogramming of Mouse Somatic Cells, Cell Stem Cell, 2008, pp. 151-159, vol. 2.
Brevig, et al., The Recognition of Adsorbed and Denatured Proteins of Different Topographies by β2 Integrins and Effects on Leukocyte Adhesion and Activation, Biomaterials, 2005, pp. 3039-3053, vol. 26.

(56) References Cited

OTHER PUBLICATIONS

Brevini et al, Embryonic Stem Cells in Domestic Animals: No Shortcuts to Pig Embryonic Stem Cells, Theriogenology, 2010, 544-550, 74.

Bross, et al., Approval Summary for Bortezomib for Injection in the Treatment of Multiple Myeloma, Clinical Cancer Research, Jun. 15, 2004, pp. 3954-3964, vol. 10.

Brown, et al., Optimal Control of Blood Glucose: The Diabetic Patient or the Machine?, Science Translation Medicine, Apr. 14, 2010, pp. 1-5, vol. 2 Issue 27.

Burkard et al, Conditional Neuronal Nitric Oxide Synthase Overexpression Impairs Myocardial Contractility, Circulation Reseach, Jan. 18, 2007, pp. e32-e44, vol. 100.

Buzzard et al., Karyotype of human ES cells during extended culture, Nature Biotechnology, Apr. 1, 2004, 381-382, 22-4, Nature Publishing Group.

Cai, et al., Generation of Homogeneous PDX1+Pancreatic Progenitors from Human ES Cell-derived Endoderm Cells, Journal of Molecular Cell Biology, Nov. 12, 2009, pp. 50-60, vol. 2.

Cao, et al., High Glucose is Necssary for Complete Maturation of Pdx1-VP16-Expressing Hepatic Cells into Functional Insulin-Producing Cells, Diabetes, 2004, pp. 3168-3176, vol. 53.

Castaing, et al., Blood Glucose Normalization Upon Transplantation of Human Embryonic Pancreas into Beta-Cell-Deficient SCID Mice, Diabetologica, 2001, pp. 2066-2076, vol. 44.

Chambers, et al., Functional Expression Cloning of Nanog, a Pluripotency Sustaining Factor in Embryonic Stem Cells, Cell, May 30, 2003, pp. 643-655, vol. 113.

Chapple, et al., Unfolding Retinal Dystrophies: A Role for Molecular Chaperones?, Trends in Molecluar Medicine, 2001, pp. 414-421, vol. 7, No. 9.

Chen, et al., A Small Molecule that Directs Differentiation of Human ESCs into the Pancreatic Lineage, Nature Chemical Biology, Apr. 11, 2009, pp. 258-265, vol. 5, No. 4.

Chen, et al., Chemically Defined Conditions for Human iPSC Derivation and Culture, Nature Methods, 2011, pp. 424-429, vol. 8, Issue 5.

Chen, et al., Differentiation of Embryonic Stem Cells Towards Pancreatic Progenitor Cells and their Transplantation into Strepozotocin-Induced Diabetic Mice, Cell Biology International, 2008, pp. 456-461, vol. 32.

Chen, et al., Differentiation of Rat Marrow Mesencymal Stem Cells in Pancreatic Islet Beta-Cells, World Journal of Gastroenterology, Oct. 15, 2004, 3016-3020, 10.

Chen, et al., Retinoic Acid Signaling is Essential for Pancreas Development and Promotes Endocrine at the Expense of Exocrine Cell Differentiation in Xenopus, Developmental Biology, 2004, pp. 144-160, vol. 271.

Cheon et al., Secretory Leukocyte Protease Inhibitor (SLPI) Regulate the Embryonic Differentiation During Periimplantation Stage, Biology of Reproduction, 2007, 64, 77, Society for the Study of Reproduction, Inc.

Cheon et al., Defined Feeder-Free Culture System of Human Embryonic Stem Cells, Biol Reprod, 2005, 105.046870, DOI10/1095.

Chetty, et al., A Simple Tool ti Improve Pluripotent Stem Cell Differentiation, Nature Methods, 2013, pp. 553-558, vol. 10, No. 6.

Choi, et al., In Vitro Trans-Differentiation of Rat Mesenchymal Cells into Insulin-Producing Cells by Rat Pancreatic Extract, Biochemical and Biophysical ResearchCommunications, 2005, pp. 1299-1305, vol. 330.

Chung, et al., Human Embryonic Stem Cell Lines Generated without Embryo Destruction, Cell Stem Cell, 2008, pp. 113-117, vol. 2.

Cohick, et al., The Insulin-Like Growth Factors, Annual Reviews Physiol, 1993, pp. 131-153, vol. 55, Annual Reviews Inc.

Corbeil, et al., Rat Prominin, Like its Mouse and Human Orthologues, is a Pentaspan Membrane Glycoprotein, Biochemical and Biophysical Research Communications, 2001, pp. 939-944, vol. 285, No. 4.

Crane, et al., An Embryogenic Model to Explain Cytogenetic Inconsistencies Observed in Chorionic Villus Versus Fetal Tissue, Prenatal Diagnosis, 1988, pp. 119-129, vol. 8.

Cresta, et al., Phase I Study of Bortezomib with Weekly Paclitaxel in Patients with Advanced Solid Tumours, European Journal of Cancer, 2008, pp. 1829-1834, vol. 44.

Cure, et al., Improved Metabolic Control and Quality of Life in Seven Patients with Type 1 Diabetes Following Islet After Kidney Transplantation, Cell Therapy and Islet Transplantation, Mar. 27, 2008, pp. 801-812, vol. 85, No. 6.

D'Amour et al., Production of pancreatic hormone-expressing endocrine cells from human embryonic stem cells, Nature Biotechnology, Oct. 19, 2006, 1392-1401, 24-11, Nature Publishing Group, US.

D'Amour et al., Efficient differentiation of human embryonic stem cells to definitive endoderm, Nature Biotechnology, Oct. 28, 2005, 1-8, :W.1038/nbt1163, Nature Publishing Group.

Damy, et al., Increased Neuronal Nitric Oxide Synthase-Derived NO Production in the Failing Human Heart, Research Letters, Apr. 24, 2004, pp. 1365-1367, vol. 363.

David M. Chacko, et al., Survival and Differentiation of Cultured Retinal Progenitors Transplanted in the Subretinal Space of the Rat, Biochemical and Biophysical Research Communications, 2000, pp. 842-846, vol. 268, Academic Press.

De Coppi, et al., Isolation of Amniotic Stem Cell Lines with Potential for Therapy, Nature Biotechnology, 2007, pp. 100-106, vol. 25, No. 1.

De Rosa, 11-color, 13-parameter flow cytometry: Identification of . . . , Nature, Feb. 1, 2001, 245-248, 7-2, Nature Publishing Group, US.

Dekker, et al., Adhesion of Endothelial Cells and Adsorption of Serum Proteins on Gas Plasma-Treated Polytetrafluoroethylene, Biomaterials, 1991, pp. 130-138, vol. 12.

Denning, et al., Common Culture Conditions for Maintenance and Cardiomyocyte Differentiation of the Human Embryonic Stem Cell Lines, BG01 and HUES-7, Int. J. Del. Biol., 2006, pp. 27-37, vol. 50.

Deramaudt, et al., The PDX1 Homeodomain Transcription Factor Negatively Regulates the Pancreatic Ductal Cell-specific Keratin 19 Promoter*, Journal of Biological Chemistry, 2006, pp. 38385-38395, vol. 281, No. 50.

Donovan, et al., The End of the Beginning for Pluripotent Stem Cells, Nature, Nov. 2001, pp. 92-97, vol. 414.

Dorrell, et al., Editorial, Stem Cell Research, 2008, pp. 155-156, vol. 1.

Doyle, et al., Cell and Tissue Culture: Laboratory Procedures in Biotechnology, Cell and Tiossue Culture: Laboratory Procedures in Biotechnology, 1995, Textbook, Textbook, Wiley.

Draper, et al., Recurrent Gain of Chromosomes 17q and 12 in Cultured Human Embryonic Stem Cells, Nature Biotechnology, 2004, pp. 53-54, vol. 22, No. 1.

Draper, et al., Surface Antigens of Human Embryonic Stem Cells: Changes Upon Differentiation in Culture, Journal Anatomy, 2002, pp. 249-258, vol. 200, Anatomical Society of Great Britain and Ireland.

Dufour, et al., Development of an Ectopic Site for Islet Transplantation Using Biodegradable Scaffolds, Tissue Engineering, 2005, pp. 1323-1331 XP002699177, vol. 11, No. 9/10.

Dupont-Gillain, et al., Plasma-Oxidized Polystyrene: Wetting Properties and Surface Reconstruction, Langmuir, 2000, pp. 8194-8200, vol. 16.

Edlund, Pancreatic Organogenisis—Pancreatic Mechanisims and Implications for Therapy, Nature, Jul. 1, 2002, 524-532, 3, Nature Publishing Group, US.

Eguizabal, et al., Embryonic Stem Cells/Induced Pluriptent Stem Complete Meiosis from Human Induced Pluripotent Stem Cells, Stem Cells, 2011, pp. 1186-1195, vol. 29.

Ellerstrom, et al., Derivation of a Xeno-Free Human Embryonic Stem Cell Line, Stem Cells, 2006, pp. 2170-2176, vol. 24.

Ellerstrom, et al., Facilitated Expansion of Human Embryonic Stem Cells by Single-Cell Enzymatic Dissociation, Stem Cells, 2007, pp. 1690-1696, vol. 25, No. 7.

(56) References Cited

OTHER PUBLICATIONS

Ellmers, et al., Transforming Growth Factor-B Blockade Down-Regulates the Renin-Angiotensin System and Modifies Cardiac Remodling after Myoardial Infarction, Endocrinology, Jul. 24, 2008, pp. 5828-5834, vol. 149—Issue 11, The Endocrine Society.
Enzmann, et al., Enhanced Induction of RPE Lineage Markers in Pluripootent Neural Stem Cells Engrafted into the Adult Rat Subretinal Space, Ophthamology & Visual Science, Dec. 2003, pp. 5417-5422, vol. 44, No. 12, Association for Research in Vision and Ophthamology.
Eventov-Friedman, et al., Embryonic Pig Pancreatic Tissue Transplantation for the Treatment of Diabetes, PLoS Medicine, Jul. 2006, e215, pp. 1165-1177, vol. 3, Issue 7.
Ezashi, et al., Low O2 Tensions and the Prevention of Differentiation of hES Cells, Proceedings of the National Academy of Sciences of USA, Mar. 29, 2005, pp. 4783-4788, vol. 102, No. 13.
Fauza, Amniotic Fluid and Placental Stem Cells, Ballieres Best Practice and Research Clinical Obsterics and Gynaecology, 2004, pp. 877-891, vol. 18, No. 6.
Fidler et al., Selective Immunomodulation by the Antineoplastic Agent Mitoxantrone, Journal of Immunology, Jul. 15, 1986, 727-732, 137-2, American Society of Immunologists, US.
Fischer, et al., Residues in the C-Terminal Region of Activin A Determine Specificity for Follistatin and Type II Receptor Binding, Journal of Endocrinology, 2003, pp. 61-68, vol. 176, Society for Endocrinology.
Florio, et al., Activin A Stimulates Insulin Secretion in Cultured Human Pancreatic Islets, J. Endocrinol. Invest., 2000, pp. 231-234, vol. 23.
Fok, et al., Shear-Controlled Single-Step Mouse Embryonic Stem Cell Expansion and Embryoid Body-Based Differentiation, Stem Cells, 2005, pp. 1333-1342, vol. 23.
Foster, et al., Differentiation of Transplanted Microencapsulated Fetal Pancreatic Cells, Experimental Transplantation, Jun. 15, 2007, pp. 1440-1448, vol. 83, No. 11.
Frandsen et al., Activin B mediated induction of Pdx1 in human embryonic stemcell derived embryoid bodies, Biochemical and Biophysical Research Communications, Aug. 15, 2007, 568-574, 362, Elsevier Inc.
Frigui, et al., A Robust Competitive Clustering Algorithm With Applications in Computer Vision, IEEE Transactions on Pattern Analysis and Machine Intelligence, May 1, 1999, pp. 450-465, vol. 21, No. 5, IEEE, US.
Fung, et al., The Effect of Medical Therapy and Islet Cell Transplantation on Diabetic Nephropathy: An Interim Report, Transplantation, Jul. 15, 2007, pp. 17-22, vol. 84, No. 1.
Furue, et al., Heparin Promotes the Growth of Human Embryonic Stem Cells in a Defined Serum-Free Medium, Proceedings of the National Academy of Sciences, Sep. 9, 2008, pp. 13409-13414, vol. 105, No. 36.
Gadue, et al., Wnt and TGB-B Signaling Are Required for the Induction of an in vitro Model of Primitive Streak Formation Using Embryonic Stem Cells, Proceedings of the National Academy of Sciences, Nov. 7, 2006, 16806-16811, 103-45, National Academy of Sciences, US.
Gaspar, et al., Inhibition of Transforming Growth Factor Signaling Reduces Pancreatic Adenocarcinoma Growth and Invasiveness, Molecular Pharmacology, 2007, pp. 152-161, vol. 72, Issue 1.
Gellibert, et al., Identification of 1,5-Naphthyridine Derivatives as a Novel Series of Potent and Selective TGF-B Type I Receptor Inhibitor, J. Med. Chem, 2004, pp. 4494-4506, vol. 47, No. 18.
Gershengorn et al., Epithelial-to-Mesenchymal Transition Generates Proliferative Human Islet Precursor Cells, Science, Dec. 24, 2004, 2261-2264, 306, US.
Gibco, Solutions for Life Science Research and Drug Discovery, Catalogue Cell Culture Products, 2004-2005, pp. 1-4E, 281406 26 5 27.
Giltaire, et al., The CYP26 Inhibitor R115866 Potentiates the Effects of All-Trans Retinoic Acid on Cultured Human Epidermal Keratinocytes, British Journal of Dermatology, 2009, pp. 505-513, vol. 160.
Ginis, et al., Differences Between Human and Mouse Embryonic Stem Cells, Developmental Biology, 2004, pp. 360-380, vol. 269.
Gittest, Developmental Biology of the Pancreas: A comprehensive Review, Developmental Biology, 2009, pp. 4-35 XP025995041, vol. 326, No. 1.
Gordon Weir, Do stem cells hold the key to creation of a cure for diabetes?, Diabetes Voice, 2008, pp. 29-31, Edition 53, No. 2.
Gosden, et al., Amniotic Fluid Cell Types and Culture, British Medical Bulletin, 1983, pp. 348-354, vol. 39, No. 4.
Graham, et al., Characteristics of a Human Cell Line Transformed by DNA from Human Adenovirus Type 5, Journal General Virology, 1977, pp. 59-72, vol. 36.
Gregg Duester, Retionoic Acid Synthesis and Signaling During Early Organogenesis, Cell, 2008, pp. 921-931, vol. 134.
Guo, et al., Stem Cells to Pancreatic B-Cells: New Sources for Diabetes Cell Therapy, Endocrine Reviews, May 2009, pp. 214-227, vol. 30, No. 3, The Endocrine Society.
Hadley, et al., Extracellular Matrix Regulates Sertoli Cell Differentiation, Testicular Cord Formation, and Germ Cell Development In Vitro, The Journal of Cell Biology, Oct. 1985, 1511-1522, 101, Rockefeller University Press.
Hainsworth, et al., Retinal Capillary Basement Membrane Thickening in a Porcine Model of Diabetes Mellitus, Comp Med, 2002, pp. 523-529, vol. 52.
Hamann, et al., Phenotypic and Functional Separation of Memory and and Effector Human CD8+ T Cells, Journal of Experimental Medicine, Mar. 11, 1997, 1407-1418, 186-9, Rockefeller University Press, US.
Harb, et al., The Rho-Rock-Myosin Signaling Axis Determines Cell-Cell Integrity of Self-Renewing Pluripotent Stem Cells, Plos One, 2008, Article e3001, XP002530386, vol. 3, Issue 8.
Harmon, et al., GDF11 Modulates NGN3+ Islet Progenitor Cell Number and Promotes B-Cell Differentiation in Pancreas Development, Development, 2004, pp. 6163-6174, vol. 131.
Haruta, et al., In Vitro and In Vivo Characterization of Pigment Epithelieal Cells Differentiated from Primate Embryonic Stem Cells, Investigative Ophthalmology & Visual Science, Mar. 2004, pp. 1020-1025, vol. 45, No. 3, Association for Research in Vision and Ophthalmology.
Hasegawa, et al., A Method for the Selection of Human Embryonic Stem Cell Sublines with High Replating Efficiency After Single-Cell Dissociation, Stem Cells, 2006, pp. 2649-2660, vol. 24.
Hashemi, et al., A Placebo Controlled, Dose-Ranging, Safety Study of Allogenic Mesenchymal Stem Cells Injected by Endomyocardial Delivery after an Acute Myocardial Infarction, European Heart Journal, Dec. 11, 2007, pp. 251-259, vol. 29.
Hay, et al., Highly Efficient Differentiation of hESCs to Functional Hepatic Endoderm Requires ActivinA and Wnt3a Signaling, PNAS, 2008, pp. 12301-12306, vol. 105, No. 34.
Hebrok, et al., Notochord repression of endodermal Sonic hedgehog permits pancreas development, Genes & Development, Jun. 1, 1998, pp. 1705-1713, vol. 12 , Issue 11, Cold Spring Harbor Laboratory Press.
Heinis, et al., HIF1a and Pancreatic Beta-Cell Development, The FASEB Journal, 2012, pp. 2734-2742, vol. 26.
Heinis, et al., Oxygen Tension Regulates Pancreatic Beta-Cell Differentiation Through Hypoxia-Inducible Factor 1x, Diabetes, 2010, pp. 662-669, vol. 59.
Heit, et al., Embryonic Stem Cells and Islet Replacement in Diabetes Mellitus, Pediatric Diabetes, 2004, pp. 5-15, vol. 5.
Held, et al., The Effect of Oxygen Tension on Colony Formation and Cell Proliferation of Amniotic Fluid Cells In-Vitro, Prenatal Diagnosis, 1984, pp. 171-180, vol. 4, No. 3.
Henderson, et al., Preimplantation Human Embryos and Embryonic Stem Cells Show Comparable Expression of Stage-Specific Embryonic Antigens, Stem Cells, 2002, pp. 329-337, vol. 20.
Heng, et al., Mechanical dissociation of human embryonic stem cell colonies by manual scraping after collagenase treatment is much

(56) References Cited

OTHER PUBLICATIONS more detrimental to cellular viability than is trypsinization with gentle pipetting, Biotechnol. Appl. Biochem., 2007, 33-37, 47, Portland Press Ltd., GB.
Heremans, et al., Recapitulation of Embryonic Neuroendocrine Differentiation in Adult Human Pancreatic Duct Cells Expressing Neurogenin 3, The Journal of Cell Biology, 2002, pp. 303-311, vol. 159.
Herrera, Adult-Insulin- and Glucagon-Producing Cells Differentiate from Two Independent Cell Lineages, Development, 2000, pp. 2317-2322 XP001004766, vol. 127, No. 11.
Herzenberg, et al., Fluorescence-activated Cell Sorting, Scientific American, 1976, 108-117, 234, Scientific American, US.
Hess, et al., Bone Marrow-Derived Stem Cells Initiate Pancreatic Regeneration, Nature Biotechnology, Jul. 2003, pp. 763-770, vol. 21, No. 7.
Ho, et al., Animal Cell Bioreactors, Animal Cell Bioreactors, 1991, 1-512, Hardcover, Butterworth-Heinemann.
Hoehn, et al., Morphological and Biochemical Heterogeneity of Amniotic Fluid Cells in Culture, Methods in Cell Biology, 1982, pp. 11-34, vol. 26, Academic Press, Inc.
Hoffman, et al., Characterization and Culture of Human Embryonic Stem Cells, Nature Biotechnology, 2005, pp. 699-708, vol. 23, No. 6.
Hori, et al., Growth inhibitors promote differentiation of insulin-producing tissue from embryonic stem cells, Proceedings of the National Academy of Sciences, Dec. 10, 2002, 16105-16110, 99-25, National Academy of Sciences.
Hosoya, et al., Induction of Differentiation of Undifferentiated Cells into Pancreatic Beta-Cells in Vertebrates, Int. J. Dev. Biol., 2012, pp. 313-323, vol. 56.
Hussain, et al., Stem-Cell Therapy for Diabetes Mellitus, Lancet, 2004, pp. 203-205, vol. 364.
Ianus, et al., In Vivo Derivation of Glucose-Competent Pancreatic Endocrine Cells from Bone Marrow Without Evidence of Cell Fusion, The Journal of Clinical Investigation, Mar. 2003, pp. 843-850, vol. 111, No. 6.
Inami, et al., Differentiation of Induced Pluripotent Stem Cells to Thymic Epithelial Cells by Phenotype, Immunology and Cell Biology, Jun. 24, 2010, pp. 1-8, doi:10.1038/icb.2010.96.
Inman, et al., SB-431542 is a Potent and Specific Inhibitor of Transforming Growth Factor-B Superfamily Type I Activing Receptor-Like Kinase (ALK) Receptors ALK4, ALK5, and ALK7, Molecular Pharmacology, 2002, pp. 65-74, vol. 62, No. 1.
INT Anker, et al., Amniotic Fluid as a Novel Source of Mesenchymal Stem Cells for Therapeutic Transplantation, Blood, Aug. 15, 2003, pp. 1548-1549, vol. 102, No. 4.
Inzunza, et al., Derivation of Human Embryonic Stem Cell Lines in Serum Replacement Medium Using Postnatal Human Fibroblasts as Feeder Cells, Stem Cells, 2005, 544-549, 23, AlphaMed Press.
Itkin-Ansari, et al., Cell-Based Therapies for Diabetes: Progress Towards a Transplantable Human B Cell Line, Annals of the New York Academy of Sciences, 2003, pp. 138-147, vol. 1005, No. 1.
Jaenisch, et al., Stem Cells, the Molecular Circuitry of Pluripotency and Nuclear Reprogramming, cell, Feb. 22, 2008, pp. 567-582, vol. 132, Elsevier Inc.
Jafary, et al., Differential effect of activin on mouse embryonic stem cell differentiation in insulin-secreting cells under nestin-positive selection and spontaneous differentiation protocols, Cell Biology International, 2008, 278-286, 32, Elsevier.
Jeon, et al., Endocrine Cell Clustering During Human Pancreas Development, J Histochem Cytochem, 2009, pp. 811-824, vol. 57, Issue 9.
Jiang, et al., Generation of Insulin-Producing Islet-Like Clusters from Human Embryonic Stem Cells, Stem Cells, 2007, pp. 1940-1953, vol. 25, Issue 8.
Jiang, et al., In Vitro Derivation of Functional Insulin-Producing Cells from Human Embryonic Stem Cells, Cell Research, 2007, pp. 333-344, vol. 17.
Johansson, et al., Temporal Control of Neurogenin3 Activity in Pancreas Progenitors Reveals Competence Windows for the Generation of Different Endocrine Cell Types, Developmental Cell, Mar. 2007, pp. 457-465, vol. 12.
Kahan, Pancreatic Precursors and Differentiated Islet Cell Types from Murine Embryonic Stem Cells, Diabetes, Aug. 2003, pp. 2016-2042, vol. 52.
Karvonen, et al., Incidene of Childhood Type 1 Diabetes Worldwide, Diabetes Care, 2000, pp. 1516-1526, vol. 23, No. 10.
Kelly, et al., Cell-Surface Markers for the Isolation of Pancreatic Cell Types Derived from Human Embryonic Stem Cells, Nature Biotechnology, 2011, pp. 750-756, vol. 29, Issue 8.
Kicic, et al., Differentiation of Marrow Stromal Cells into Photoreceptors in the Rat Eye, The Journal of Neuroscience, Aug. 27, 2003, pp. 7742-7749, vol. 23, Issue 21.
Kingsley, The TGF-B Superfamily: New Members, New Receptors, and New Genetic Tests of Function in Different Organisms, Genes & Development, 1994, pp. 133-146, XP009011502, vol. 8, Cold Spring Harbor Laboratory Press.
Kinkel, et al., Cyp26 Enzymes Function in Endoderm to Regulate Pancreatic Field Size, PNAS, May 12, 2009, pp. 7864-7869, vol. 106, No. 19.
Klajnert, et al., Fluorescence studies on PAMAM dendrimers interactions with bovine serum albumin, Bioelectrochemistry, 2002, pp. 33-35, vol. 55.
Kleinman et al., Basement Membrane Complexes with Biological Activity, Biochemistry, 1986, 312-318, 25, American Chemical Society.
Klimanskaya, et al., Human Embryonic Stem Cells Derived without Feeder Cells, Lancet, May 2005, pp. 1636-1641, vol. 365, No. 9471.
Koblas, et al., Differentiation of CD133-Positive Pancreatic Cells Into Insulin-Producing Islet-Like Cell Clusters, Transplantation Proceedings, 2008, pp. 415-418, vol. 40.
Kohen, et al., Characterization of Matrigel Interfaces During Defined Human Embryonic Stem Cell Culture, Characterization of Matrigel Interfaces During Defined Human Embryonic Stem Cell Culture, Sep. 3, 2010, pp. 6979, vol. 4.
Koller, et al., Effects of Synergistic Cytokine Combinations, Low Oxygen, and Irradiated Stroma on the Expansion of Human Cord Blood Progenitors, Blood, Jul. 15, 1992, pp. 403-411, vol. 80, No. 2.
Konstantinova_et_al_2007, EphA—Ephrin-A-Mediated Beta Cell Communication Regulates Insulin Secretion from Pancreatic Islets, Cell, Apr. 20, 2007, pp. 359-370, vol. 129.
Koyangi et al., Inhibitio nof the Rho/ROCK Pathway Reduces Apoptosis During Transplantatation of Embryonic Stem Cell-Derived Neural Precursors, Journal of Neurosciene Research, Sep. 7, 2007, 270-280, 86, Wiley-Liss, Inc.
Kozikowski, et al., New Amide-Bearing Benzolactam-Based Protein Kinase C Modulators Induce Enhanced Secretion of the Amyloid Precuros Protein Metabolite sAPPa, J. Med. Chem., 2003, pp. 364-373, vol. 46, No. 3.
Krapcho et al., Synthesis and Antineoplastic Evaluations of 5,8-Bis[(aminoalkyl)amino]-1-azaanthracene-9,10-diones, Journal of Medical Chemistry, 1985, 1124-1126, 28, American Chemical Society.
Krawetz, et al., Human Embryonic Stem Cells: Caught Between a ROCK Inhibitor and a Hard Place, BioEssays: News and Reviews in Molecular Cellular and Developmental Biology, 2009, pp. 336-343, vol. 31.
Kron, et al., Expression of Human Activin C Protein in Insect Larvae Infected with a Recombinant Baculovirus, Journal of Virological Methods, 1998, pp. 9-14, vol. 72.
Kroon, et al., Pancreatic Endoderm Derived from Human Embryonic Stem Cells Generates Glucose-Responsive Insulin-Secreting Cells in vivo, Nature Biotechnology, Apr. 2008, pp. 443-452, vol. 26, No. 4.
Krutzik, et al., Coordinate Analysis of Murine Immune Cell Surface Markers and Intracellular Phosphoproteins by Flow Cytometry, Journal of Immunology, May 30, 2005, 2357-2365, 175, American Association of Immunologists, Inc., US.

(56) References Cited

OTHER PUBLICATIONS

Ku et al., Committing Embryonic Stem Cells to Early Endocrine Pancreas In Vitro, Stem Cells, 2004, 1205-1217, 22, AlphaMed Press.

Kubo et al., Development of definitive endoderm from embryonic stem cells in culture, Development, 2004, 1651-1662, 131, The Company of Biologists.

Kubota,et al., Growth factors essential for self-renewal and expansion of mouse spermatogonial stem cells, cell Biology, Nov. 23, 2004, pp. 16489-16494, vol. 101 , Issue 47.

Kurihara-Bergstrom, et al., Characterization of the Yucatan Miniature Pig Skin and Small Intestine for Pharmaceutical Applications, Laboratory Animal Science, 1986, pp. 396-399, vol. 36, No. 4.

Lanza, et al., Characteristics and Characterization of Human Pluripotent Stem Cells, Stem Cell Anthology, 2010, pp. 141, 142, 144 and 146, 1st Edition.

Laplante, et al., RhoA/ROCK and Cdc42 Regulate Cell-Cell Contact and N-Cadherin Protein Level During Neurodetermination of P19 Embryonal Stem Cells, Journal of Neurobiology, 2004, pp. 289-307, vol. 60, No. 3.

Larsen, et al., Evaluation of B-Cell Mass and Function in the Gottingen Minipig, Diabetes, Obesity and Metabolism, 2007, pp. 170-179, vol. 9, Supplement 2, Blackwell Publishing Ltd.

Larsen, et al., Use of the Gootingen Minipig as a Model of Diabetes, with Special Focus on Type 1 Diabetes Research, ILAR Journal, 2004, pp. 303-313, vol. 45, No. 3.

Lavon et al., The Effect of Overexpression of Pdx1 and Foxa2 on the Differentiation of Human Embryonic Stem Cells into Pancreatic Cells, Stem Cells, 2006, 1923-1930, 24, Alpha Med Press, IL.

Le Blanc, et al., Mesenchymal Stem Cells Inhibit and Stimulate Mixed Lymphocyte Cultures and Mitogenic Responses Independently of the Major Histocompatibility Complex, Scandinavian Journal of Immunology, 2003, pp. 11-20, vol. 57, Blackwell Publishing Ltd.

Lee et al., Establishment and Maintenance of Human Embryonic Stem Cell Lines on Human Feeder Cells Derived from Uterine Endometrium under Serum-Free Condition, Biology of Reproduction, Aug. 18, 2004, 42-49, 72.

Lee, et al., Human B-cell Precursors Mature into Functional Insulin-Producing Cells in an Immunoisolation Device: Implications for Diabetes Cell Thereapies, Transplantation, Apr. 15, 2009, pp. 983-991, vol. 87, No. 7.

Lee, et al., PKC—Inhibitors Sustain Self-Renewal of Mouse Embryonic Stem Cells Under Hypoxia in Vitro, Experimental and Molecular Medicine, Apr. 2010, pp. 294-301, vol. 43, No. 4.

Lee, et al., Protein Kinase A- and C-Induced Insulin Release from Ca2+-Insensitive Pools, Cellular Signalling, 2003, pp. 529-537, vol. 15.

Lee, et al., Retionic Add-Induced Human Secretin Gene Expression in Neuronal Cells is Mediated by Cyclin-Dependent Kinase 1, Annals of the New York Academy of Sciences, 2006, pp. 393-398, vol. 1070.

Leeper, et al., Stem Cell Therapy for Vascular Regeneration Adult, Embryonic, and Induced Pluripotent Stem Cells, Circulation, Aug. 3, 2010, pp. 517-526, vol. 122, No. 5.

Leon-Quinto, et al., In Vitro Directed Differentiation of Mouse Embryonic Stem Cells into Insulin-Producing Cells, Diabetologia, 2004, pp. 1442-1451 XP002699175, vol. 47, No. 8.

Levenstein et al., Basic Fibroblast Growth Factor Support of Human Embryonic Stem Cell Self-Renewal, Stem Cells, Nov. 10, 2005, 568-574, 24, AlphaMed Press.

Li et al., Generation of Rat and Human Induced Pluripotent Stem Cells by Combining Genetic Reprogramming and Chemical Inhibitors, Cell Stem Cell, Jan. 9, 2009, pp. 16-19, vol. 4.

Li, et al., Pluripotency Can be Rapidly and Efficiently Induced in Human Amniotic Fluid-Derived Cells, Human Molecular Genetics, 2009, pp. 4340-4349, vol. 18, No. 22.

Lilja et al., Cyclin-dependent Kinase 5 Promotes Insulin Exocytosis, Journal of Biological Chemistry, Jul. 6, 2001, 34199-34205, 36-7, JBC Papers in Press.

Lim, et al., Proteome Analysis of Conditioned Medium from Mouse Embryonic Fibroblast Feeder Layers which Support the Growth of Human Embryonic Stem Cells, Proteomics, 2002, pp. 1187-1203, vol. 2.

Liu, et al., A Novel Chemical-Defined Medium with bFGF and N2B27 Supplements Supports Undifferentiated Growth in Human Embryonic Stem Cells, Biochemical and Biophysical Research Communications, 2006, pp. 131-139, vol. 346.

Loh, et al., Genomic Approaches to Deconstruct Puripotency, Annu Rev Genomics Hum Genet, 2011, pp. 165-185, vol. 12.

Ludwig, et al., Defined Culture Media for Human Embryonic Stem Cells, Embryonic Stem Cells, 2007, pp. 1-16, XP009185398, Springer.

Ludwig, et al., Derivation of Human Embryonic Stem Cells in Defined Conditions, Nature Biotechnology, Feb. 2006, pp. 185-187, vol. 24 No. 2.

Lumelsky, et al., Differentiation of Embryonic Stem Cells to Insulin-Secreting Structures Similar to Pancreatic Islets, Science, 2001, 1389-1394, 292, HighWire Press.

Lund, et al., Cell Transplantation as a Treatment for Retinal Disease, Progress in Retinal and Eye Research, 2001, pp. 415-449, vol. 20, No. 4, Elsevier Science Ltd.

Lund, et al., Retinal Transplantation: Progress and Problems in Clinical Application, Journal of Leukocyte Biology, Aug. 2003, pp. 151-160, vol. 74.

Lyttle, et al., Transcription Factor Expression in the Developing Human Fetal Endocrine Pancreas, Diabetologica, 2008, pp. 1169-1180, vol. 51, Spring-Verlag.

MacFarlane, et al., Glucose Stimulates Translocation of the Homeodomain Transcription Factor PDX1 from the Cytoplasm to the Nucleus in Pancreatic B-Cells, The Journal of Biological Chemistry, 1999, pp. 1011-1016, vol. 274, No. 2.

Maherali, et al., Directly Reprogrammed Fibroblasts Show Global Epigenetic Remodeling and Widespread Tissue Contribution, Cell Stem Cell, Jul. 2007, pp. 55-70, vol. 1, Elsevier, Inc.

Mao, et al., The Reversal of Hyperglycaemia in Diabetic Mice Using PLGA Scaffolds Seeded with Islet-like Cells Derived from Human Embyonica Stem Cells, Biomaterials, 2009, pp. 1706-1714, vol. 30.

Marshall, et al., Early Micro- and Macro-Angiopathy in the Streptozotocin, Research in Experimental Medicine, 1980, pp. 145-158, vol. 177, Springer-Verlag.

Marshall, et al., Isolation and Maintenance of Primate Embryonic Stem Cells, Methods in Molecular Biology, 2001, pp. 11-18, vol. 158.

Martin, et al., Bioreactors for Tissue Mass Culture: Design, Characterization, and Recent Advances, Biomaterials, Jul. 14, 2005, pp. 7481-7503, vol. 26.

Marzo, et al., Pancreatic Islets from Cyclin-Dependent Kinase 4/R24C (Cdk4) Knockin Mice have Significantly Increased Beta Cell Mass and are Physiologically Functional, Indicating that Cdk4 is a Potential Target for Pancreatic . . . , Diabetologia, 2004, pp. 686-694, vol. 47.

Mathis, et al., B-Cell Death During Progression to Diabetes, Nature, 2001, pp. 792-798, vol. 414.

Matveyenko, et al., Inconsistent Formation and Nonfunction of Insulin-Positive Cells from Pancreatic Endoderm Derived from Human Embyonic Stem Cells in Athymic Nude Rats, American Journal of Physiol Endocrinol Metab, 2010, pp. E713-E720, vol. 299.

McKiernan, et al., Directed Differentiation of Mouse Embryonic Stem Cells into Pancreatic-Like or Neuronal- and Glial-Like Phenotypes, Tissue Engineering, 2007, pp. 2419-2430, vol. 13, No. 10.

McLean et al., Activin A Efficiently Specifies Definitive Endoderm from Human Embryonic Stem Cells Only When Phosphatidylinositol 3-Kinase Signaling Is Suppressed, Stem Cells, 2007, 29-38, 25, AlphaMed Press.

McLin, et al., Repression of WNT/(szligbeta)-6atenin Signaling in the Anterior Endoderm is Essential for Liver and Pancreas Development, Development, 2007, pp. 2207-2217, vol. 134, Issue 12.

Meijer, et al., Pharmacological Inhibitors of Glycogen Synthase Kinase 3, Trends in Pharmacological Sciences, Sep. 2004, pp. 471-480, vol. 25, No. 9.

(56) References Cited

OTHER PUBLICATIONS

Micallef et al., Retinoic Acid Induces Pdx1-Positive Endoderm in Differentiating Mouse Embryonic Stem Cells, Diabetes, Feb. 2005, 301-305, 54, American Diabetes Association.
Miller, et al., The Pig as a Model for Human Nutrition, Annual Review of Nutrition, 1987, pp. 361-382, vol. 7, Annual Reviews Inc.
Milunsky, et al., Genetic Disorders and the Fetus: Diagnosis Prevention and Treatment, Pediatric and Developmental Pathology, 2011, pp. 84, vol. 14, Society for Pediatric Pathology.
Minami, et al., A Small Molecule that Promotes Cardiac Differentiation of Human Pluripotent Stem Cells Under Defined, Cytokine- and Xeno-free Conditions, Cell Reports, 2012, pp. 1448-1460, vol. 2, No. 5.
Mitalipova, et al., Preserving the Genetic Integrity of Human Embyonic Stem Cells, Nature Biotechnology, 2005, pp. 19-20, vol. 23, No. 1.
Mitsui, et al., The Homeoprotein Nanog is Required for Maintenance of Pluripotency in Mouse Epiblast and ES Cells, Cell, May 30, 2003, pp. 631-642, vol. 113, Cell Press.
Miyamoto et al., Human Placenta Feeder Layers Support Undifferentiated Growth of Primate Embryonic Stem Cells, Stem Cells, 2004, 433-440, 22, AlphaMed Press.
Miyazaki et al., Regulated Expression of pdx-1 Promotes In Vitro Differentiation of Insulin-Producing Cells From Embryonic Stem Cells, Diabetes, Apr. 2004, 1030-1037, 53, American Diabetes Association.
Moore, et al., The Corneal Epithelial Stem Cell, DNA and Cell Biology, 2002, pp. 443-451, vol. 21, No. 5/6.
Moran, et al., Bidirectional-Barbed Sutured Knotless Running Anastomosis v Classic van Velthoven in a Model System, Journal of Endourology, 2007, pp. 1175-1177, vol. 21, No. 10.
Morrison, et al., Culture in Reduced Levels of Oxygen Promotes Clonogenic Sympathoadrenal Differentiation by Isolated Neural Crest Stem Cells, Journal of Neuroscience, Oct. 1, 2000, pp. 7370-7376, vol. 20, No. 19.
Movassat, et al., Keratinocyte Growth Factor and Beta-Cell Differentiation in Human Fetal Pancreatic Endocrine Precursor Cells, Diabetologia, 2003, pp. 822-829, vol. 46.
Muchamuel, et al., Preclinical Pharmacology and in Vitro Characterization of PR-047, An Oral Inhibitor of the 20s Proteasome, Blood, Nov. 16, 2008, pp. 1257, vol. 112, No. 11.
Munoz, et al., Conventional Pluripotency Markers are Unspecific for Bovine Embryonic-Derived Cell-Lines, Theriogenology, 2008, pp. 1159-1164, vol. 69.
Murtha, et al., Evaluation of a Novel Technique for Wound Closure Using a Barbed Suture, Cosmetic, Aug. 2, 2005, pp. 1769-1780, vol. 117, No. 6.
Nakagawa, et al., Generation of Induced Pluripotent Stem Cells without Myc from Mouse and Human Fibroblasts, Generation of Induced Pluripotent Stem Cells without Myc from Mouse and Human Fibroblasts, Jan. 2008, pp. 101-106, vol. 26, No. 1.
Nakamura, et al., Ocular Surface Reconstruction Using Cultivated Mucosal Epithelial Stem Cells, Cornea, Oct. 2003, S75-S80, vol. 22, Supplement 1.
Nelson, et al., The Transcription Factors Nkx6.1 and Nkx6.2 Possess Equivalent Activities in Promoting Beta-Cell Fate Specification in Pdx1+ Pancreatic Progenitor Cells, Development, 2007, pp. 2491-2500, vol. 134.
Nicholas et al., A Method for Single-Cell Sorting and Expansion of Genetically modified Human Embryonic Stem Cells, Stem Cells and Development, 2007, 109-119, 16, Mary Ann Liebert, Inc.
Nie, et al., Scalable Passaging of Adherent Human Pluripotent Stem Cells, PLOS One, 2014, pp. 1-9, vol. 9, Issue 1.
Nishimura, et al., Expression of MafA in Pancreatic Progenitors is Detrimental for Pancreatic Development, Developmental Biology, 2009, pp. 108-120, vol. 333.
Nostro, et al., Generation of Beta Cells from Human Pluripotent Stem Cells: Potential for Regenerative Medicine, Seminars in Cell & Developmental Biology, 2012, pp. 701-710, vol. 23.
Nostro, et al., Stage-Specific Signaling Through TGF Family Members and WNT Regulates Patterning and Pancreatic Specification of Human Pluripotent Stem Cells, Development, 2011, pp. 861-871, vol. 138, Issue 5.
Odom, et al., Control of Pancreas and Liver Gene Expression by HNF Transcription Factors, Science, 2004, pp. 1378-1381, vol. 303, No. 5662.
Oh, et al., Human Embryonic Stem Cells: Technological Challenges Towards Therapy, Clinical and Experimental Pharmacology and Physiology, 2006, pp. 489-495, vol. 33.
Okita, et al., Generation of Germline-Competent Induced Pluripotent Stem Cells, Nature, Jul. 19, 2007, pp. 313-317, vol. 448.
Orlowski, et al., Safety and Antitumor Efficacy of the Proteasome Inhibitor Carfilzomib (PR-171) Dosed for Five Consecutive Days in Hematologic Malignancies: Phase 1 Results, Blood, 2007, Part 1, vol. 110, No. 11.
Osborne, et al., Some Current Ideas on the Pathogenesis and the Role of Neuroprotection in Glaucomatous Optic Neuropathy, European Journal of Ophthalmology, 2003, S19-S26, vol. 13, Supplement 3, Wichtig Editore.
Ostrom, et al., Retinoic Acid Promotes the Generation of Pancreatic Endocrine Progenitor Cells and Their Further Differentiation into B-Cells, PLOS One, Jul. 30, 2008, e2841, pp. 1-7, vol. 3, No. 7.
Ouziel-Yahalom, et al., Expansion and Redifferentiation of Adult Human Pancreatic islet Cells, Biochemical and Biophysical Research Communications, 2006, pp. 291-298, vol. 341.
Paling, et al., Regulation of Embryonic Stem Cell, Self-Renewal by Phosphoinositide 3-kinase-dependent Signaling, Journal of Biological Chemistry, 2004, pp. 48063-48070, vol. 279, No. 46.
Panchision, et al., Optimized Flow Cytometric Analysis of Central Nervous System Tissue Reveals Novel Functional Relationships Among Cells Expressing CD133, CD15, and CD24, Stem Cells, 2007, pp. 1560-1570, vol. 25.
Panepinto, et al., The Yucatan Miniature Pig: Characterization and Utilization in Biomedical Research, Laboratory Animal Science, Aug. 1986, pp. 344-347, vol. 36, No. 4, American Association for Laboratory Animal Science.
Pangas, et al., Production and Purification of Recombinant Human Inhibin and Activin, Journal of Endocrinology, 2002, pp. 199-210, vol. 172.
Pardo, et al., Corning CellBIND Surface: An Improved Surface for Enhanced Cell Attachment, Corning Technical Report, 2005, 8 page report, XP002530385.
Paris, et al., Equine Embryos and Embryonic Stem Cells: Defining Reliable Markers of Pluripotency, Theriogeneology, 2010, pp. 516-524, vol. 74.
Park, et al., Effects of Activin A on Pancreatic Ductal Cells in Streptozotocin-Inducted Diabetic Rats, Experimental Transplantation, 2007, pp. 925-930, vol. 83.
Peerani, et al., Niche-Mediated Control of Human Embryonic Stem Cell Self-Renewal and Differentiation, The EMBO Journal, 2007, pp. 4744-4755, vol. 26.
Perrier, et al., Derivation of Midbrain Dopamine Neurons from Human Embryonic Stem Cells, PNAS, Aug. 24, 2004, pp. 12543-12548, vol. 101, No. 34.
Phillips, et al., Attachment and Growth of Human Embryonic Stem Cells on Microcarriers, Journal of Biotechnology, 2008, pp. 24-32, vol. 138.
Phillips, et al., Directed Differentiation of Human Embryonic Stem Cells into the Pancreatic Endocrine Lineage, Stem Cells and Development, 2007, pp. 561-578 XP009090586, vol. 16, No. 4.
Pouton, et al., Embryonic Stem Cells as a Source of Models for Drug Discovery, Nature Reviews Drug Discovery, Aug. 2007, pp. 1474-1776, vol. 6, No. 8.
Prichard, et al., Adult Adipose Derived Stem Cell Attachment to Biomaterials, Biomaterials, 2006, pp. 936-946, vol. 28, No. 6.
Prowse, et al., A Proteome Analysis of Conditioned Media from Human Neonatal Fibroblasts Used in the Maintenance of Human Embryonic Stem Cells, Proteomics, 2005, pp. 978-989, vol. 5.
Prusa, et al., Oct-4-Expressing Cells in Human Amniotic Fluid: a New Source for Stem Cell Research?, Human Reproduction, 2003, pp. 1489-1493, vol. 18, No. 7.

(56) References Cited

OTHER PUBLICATIONS

Ptasznik, et al., Phosphatidylinositol 3-Kinase Is a Negative Regulator of Cellular Differentiation, The Journal of Cell Biology, 1997, pp. 1127-1136, vol. 137, No. 5.
R&D Systems, Embryonic & Induced Pluripotent Stem Cell Transcription Factors, Embryonic & Induced Pluripotent Stem Cell Transcription Factors, 2013, http://www.rndsystems.com/molecule_group.aspx?r=1&g-3041, 2 page web printout.
R&D Systems, Pancreatic Endoderm, Pancreatic Endoderm, Jun. 24, 2013, http://www.rndsystems.com/molecule_group.aspx?g=801&r, 1 page web printout.
Rajagopal, et al., Insulin Staining of ES Cell Progeny from Insulin Uptake, Science, Jan. 17, 2003, pp. 363, vol. 299.
Rajala, et al., Testing of Nine Different Xeno-free Culture Media for Human Embryonic Stem Cell Cultures, Human Reproduction, Jan. 24, 2007, pp. 1231-1238, vol. 22, No. 5.
Ramiya, et al., Reversal of Insulin-Dependent Diabetes Using Islets Generated in vitro from Pancreatic Stem Cells, Nature Medicine, 2000, pp. 278-281, vol. 6.
Rao, Conserved and Divergent Paths that Regulate Self-Renewal in Mouse and Human Embryonic Stem Cells, Developmental Biology, Aug. 10, 2004, pp. 269-286, vol. 275, Elsevier, Inc.
Ratanasavanh,et al., Immunocytochemical Evidence for the Maintenance of Cytochrome P450 Isozymes, NADPH Cytochrome C Reductase, and Epoxide Hydrolase in Pure and Mixed Primary Cultures of Adult Human Hepatocytes1, The Journal of Histochemistry and Cytocheinistry, 1986, pp. 527-533, vol. 34, Issue 4.
Rebbapragada, et al., Myostatin Signals Through a Transforming Growth Factor B-Like Signaling Pathway to Block Adipogenesis, Molecular and Cellular Biology, 2003, pp. 7230-7242, vol. 23, No. 20.
Rebollar, et al., Proliferation of Aligned Mammalian Cells on Laser-Nanostructured Polystyrene, Biomaterials, 2008, pp. 1796-1806, vol. 29.
Reisner, Growing Organs for Transplantation form Embryonic Precursor Tissues, Immunol. Res., 2007, pp. 261-273, vol. 38.
Reubinoff et al., Embryonic stem cell lines from human blastocysts: somatic differentiation in vitro, Nature Biotech, Apr. 18, 2000, 399-404, 18, Nature America Inc.
Rezania, E al., Maturation of Human Embryonic Stem Cell-Derived Pancreatic Progenitors Into Functional Islets Capable of Treating Pre-Existing Diabetes in Mice, Diabetes, 2012, pp. 2016-2029, vol. 61.
Rezania, et al., Enrichman of Human Embryonic Stem Cell-Derived NKX6.1-Expressing Pancreatic Progenitor Cells Accelerates the Maturation of Insulin-Secreting Cells In Vivo, Stem Cells, 2013, pp. 2432-2442, vol. 31.
Rezania, et al., Reversal of Diabetes with Insulin-Producing Cells Derived in vitro from Human Pluripotent Stem Cells, Nature Biotechnology, 2014, pp. 1121-1133, vol. 32, No. 11.
Rezania, Production of Functional Glucagon-Secreting-Cells from Human Embryonic Stem Cells, Diabetes, 2011, pp. 239-247, vol. 60, Issue 1.
Richards et al., Comparative Evaluation of Various Human Feeders for Prolonged Undifferentiated Growth of Human Embryonic Stem Cells, Stem Cells, 2003, 546-556, 21, AlphaMed Publlishing.
Richards, et al., Development of Defined Media for the Serum-Free Expansion of Primary Keratinocytes and Human Embryonic Stem Cells, Tissue Engineering, 2008, pp. 221-232, vol. 14, No. 3.
Richardson, et al., Bortezomid (PS-341): A Novel, First-in-Class Proteasome Inhibitor for the Treatement of Multiple Myeloma and Other Cancers, Cancer Control, 2003, pp. 361-369, vol. 10, No. 5.
Ricordi et al., Automated Method for Isolation of Human Pancreatic Islets, Diabetes, Apr. 1988, 413-420, 37, American Diabetes Association.
Ross, et al., Cytochrome P450s in the Regulation of Cellular Retinoic Acid Metabolism, Annu. Rev. Nutr., 2011, pp. 65-87, vol. 31.
Rowley, et al., Meeting Lot-Size Challenges of Manufacturing Adherent Cells for Therapy, Cell Therapies Manufacturing, 2012, pp. 16-22, vol. 10, No. 3.
Ryan, et al., Clinical Outcomes and Insulin Secretion After Islet Transplantation with the Edmonton Protocol, Diabetes, Apr. 2001, pp. 710-719, vol. 50.
Sakaguchi, et al., Integration of Adultmesenchymal Stem Cells in the CNS, Society for Neuroscience Abstract Viewer and Itineray Planner, 2002, XP002519394, Program 237.18.
Sander, et al., Homeobox Gene Nkk6.1 Lies Downstream of Nkx2.2 in the Major Pathway of Betta-Cell Formation in the Pancreats, Development, 2000, pp. 5533-5540, vol. 127.
Sato, et al., Maintenance of Pluripotency in Human and Mouse Embryonic Stem Cells Through Activation of Wnt Signaling by a Pharmacological GSK-3-specific Inhibitor, Nature Medicine, Jan. 2004, pp. 55-63, vol. 10, No. 1.
Sato, et al., Manipulation of Self-Renewal in Human Embryonic Stem Cells Through a Novel Pharmacological GSK-3 Inhibitor, Methods in Molecular Biology, 2006, pp. 115-128, vol. 331.
Sato, et al., Molecular Signature of Human Embryonic Stem Cells and its Comparison with the Mouse, Developmental Biology, Apr. 23, 2003, pp. 404-413, vol. 260.
Savino et al., Generation of Interleukin-6 Receptor Antagonists by Molecular-Modeling Guided Mutagenesis of Residues Important for gp130 Activation, EMBO Journal, 1994, 1357-1367, 13-6, IT.
Schaefer-Graf, et al., Patterns of congenital anomalies and relationship to initial maternal fasting glucose levels in pregnancies complicated by type 2 and gestational diabetes, Am J Obstet Gynecol, 2000, pp. 313-320, vol. 182, Issue 2.
Schisler, et al., The Nkx6.1 Homeodomain Transcription Factor Suppresses Glucagon Expression and Regulates Glucose-Stimulated Insulin Secretion in Islet Beta Cells, Proceedings of the National Academy of Sciences of the USA, 2005, pp. 7297-7302, XP002699176, vol. 102, No. 20.
Schnier, et al., G1 Arrest and Down-Regulation of Cyclin E/cyclin-dependent Kinase 2 by the Protein Kinase Inhibitor Staurosporine are Dependent on the Retinoblastoma Protein in the Bladder Carcinoma Cell Line 5637, Proceedings of the National Academy of Sciences, 1996, pp. 5941-5946, vol. 93.
Schraermeyer, et al., Subretinally Transplanted Embryonic Stem Cells Rescue Photoreceptor Cells From Degeneration in the RCS Rats, Cell Transplantation, 2001, pp. 673-680, vol. 10.
Schroeder, et al., Differentiation of Mouse Embryonic Stem Cells to Insulin-Producing Cells, Nature Protocols, 2005, pp. 495-507, vol. 1, No. 2.
Schuldiner, et al., Induced Neuronal Differentiation of Human Embryonic Stem Cells, Brain Research, 2001, pp. 201-205, vol. 913.
Schulz, et al., A Scalable System for Production of Functional Pancreatic Progenitors from Human Embryonic Stem Cells, PLOS One, 2012, pp. 1-17, vol. 7, Issue 5.
Scullica, et al., Diagnosis and Classification of Macular Degenerations: an Approach Based on Retinal Function Testing, Documenta Ophthalmologica, 2001, pp. 237-250, vol. 102.
Seaberg et al., Cfonal identification of multipotent precursors from adult~mouse pancreas that generate neural and pancreatic lineages, Nature Biotechnology, Sep. 2004, pp. 1115-1124, vol. 22, No. 9, Nature Publishing Group.
Segev, et al., Differentiation of Human Embryonic Stem Cells into Insulin-Producing Clusters, Stem Cells, Jan. 1, 2004, pp. 265-274.
Serafimidis, et al., Novel Effectors of Directed and Ngn3-Mediated Differentiation of Mouse Embryonic Stem Cells into Endocrine Pancreas Progenitors, Stem Cells, 2008, pp. 3-16, vol. 26.
Shackleton, et al., Generation of a Functional Mammary Gland from a Single Stem Cell, Nature, Jan. 5, 2006, pp. 84-88, XP002567665, vol. 439.
Shamblott et al., Derivation of pluripotent stem cells from cultured human primordial germ cells, Developmental Biology, Nov. 1998, 13726-13731, 95, National Academy of Sciences.
Shapiro, et al., Islet Transplantation in Seven Patients with Type 1 Diabetes Mellitus Using a Glucocorticoid-Free Immunosuppressive Regimen, The New England Journal of Medicine, Jul. 27, 2000, pp. 230-238, vol. 343, No. 4, The Massachusetts Medical Society.

(56) References Cited

OTHER PUBLICATIONS

Shen, et al., The Effects of Surface Chemistry and Adsorbed Proteins on Monocyte/Macrophage Adhesion to Chemically Modified Polystyrene Surfaces, Journal of Biomedical Matter Research, 2001, pp. 336-345, vol. 57.

Sherwood, et al., Transcriptional Dynamics of Endodermal Organ Formation, Developmental Dynamics, 2009, pp. 29-42, vol. 238, Issue 1.

Shi et al., Inducing Embryonic Stem Cells to Differentiate into Pancreatic β Cells by a Novel Three-Step Approach with Activin A and All-Trans Retinoic Acid, Stem Cells, 2005, 656-662, 23, AlphaMed Press.

Shim, et al., Directed Differentiation of Human Embryonic Stem Cells Towards a Pancreatic Cell Fate, Diabetologia, 2007, pp. 1228-1238, vol. 50.

Shindler et al., A synthetic nanofibrillar matrix promotes in vivo-like organization and morphogenesis for cells in culture, Biomaterials, Apr. 18, 2005, 5624-5631, 26, Elsevier.

Shiraki et al., TGF-B Signaling Potentiates Differentiation of Embryonic Stem Cells to Pdx-1 Expressing Endodermal Cells, Genes to Cells, 2005, 503-516, 10, Blackwell Publishing Limited.

Shiraki, et al., Guided Differentiation of Embryonic Stem Cells into Pdx1-Expressing Regional-Specific Definitive Endoderm, Stem Cells, 2008, pp. 874-885, vol. 26.

Sidhu et al., Derivation of Three Clones from Human Embryonic Stem Cell Lines by FACS Sorting and Their Characterization, Stem Cells and Development, 2006, 61-69, 15, Mary Ann Liebert, Inc.

Simandi, et al., Retinoid Signaling is a Context-Dependent Regulator of Embryonic Stem Cells, Embryonic Stem Cells—Differentiation and Pluripotent Alternatives, 2011, pp. 55-79, Chapter 3.

Simons, et al., Assembly of Protein Tertiary Structures from Fragments with Similar Local Sequences Using Simulated Annealing and Bayesian Scoring Functions, Journal of Molecular Biology, 1997, pp. 209-225, vol. 268.

Simons, et al., Improved Recognition of Native-Like Protein Structures Using a Combination of Sequence-Dependent and Sequence-Independent Features of Proteins, Proteins: Structure, Function, and Genetics, 1999, pp. 82-95, vol. 34, Wiley-Liss, Inc.

Skoudy et al., Transforming growth factor (TGF)β, fibroblast growth factor (FGF) and retinoid signalling pathways promote pancreatic exocrine gene expression in mouse embryonic stem cells, Journal of Biochemistry, 2004, 749-756, 379, Biochemical Society, GB.

Smith et al., Anti-Interleukin-6 Monocolnal Antibody Induces Regression of Human Prostate Cancer Xenografts in Nude Mice, The Prostate, Mar. 2, 2001, 47-53, 48, Wiley-Liss, Inc.

Sneddon, et al., Self-Renewal of Embryonic-Stem-Cell-Derived Progenitors by Organ-Matched Mesenchyme, Nature, Nov. 29, 2012, pp. 765-770, vol. 491.

Soria et al., Insulin-Secreting Cells Derived From Embryonic Stem Cells Normalize Glycemia in Streptozotocin-Induced Diabetic Mice, Diabetes, Feb. 2000, 1-6, 49, American Diabetes Association.

Soria, et al., From Stem Cells to Beta Cells: New Strategies in Cell Therapy of Diabetes Mellitus, Diabetologia, 2001, pp. 407-415, vol. 44.

Spence, et al., Translation Embryology: Using Embryonic Principles to Generate Pancreatic Endocrine Cells from Embryonic Stem Cells, Developmental Dynamics, 2007, pp. 3218-3227, vol. 236.

Stacpoole, et al., Efficient Derivation of Neural Precuros Cells, Spinal Motor Neurons and Midbr, Nat Protoc, 2012, pp. 1-26, vol. 6, Issue 8.

Stadtfeld, et al., Defining Molecular Cornerstones During Fibroblast to iPS Cell Reprogramming in Mouse, Cell Stem Cell, Mar. 2008, pp. 230-240, vol. 2.

Stafford, et al., Retinoic Add Signaling is Required for a Critical Early Step in Zebrafish Pancreatic Development, Current Biology, 2002, pp. 1215-1220, vol. 12, Issue 14.

Stafford, et al., Retinoids Signal Directly to Zebrafish Endoderm to Specify Insuilin-Expressing B-cells, Development, 2005, pp. 949-956, vol. 133.

Stoffel, et al., Navigating the Pathway from Embryonic Stem Cells to Beta Cells, Seminars in Cell & Developmental Biology, 2004, pp. 327-336, vol. 15.

Stojkovic et al., An Autogeneic Feeder Cell System That Efficiently Supports Growth of Undifferentiated Human Embryonic Stem Cells, Stem Cells, 2005, 306-314, 23, AlphaMed Press.

Sugiyama, et al., Conserved Markers of Fetal Pancreatic Epithelium Permit Prospective Isolation of Islet Progenitor Cells by FACS, PNAS, Jan. 2, 2007, pp. 175-180, vol. 104, No. 1.

Sugiyama, et al., Fluorescence-Activated Cell Sorting Purification of Pancreatic Progenitor Cells, Diabetes, Obesity and Metabolism, 2008, pp. 179-185, vol. 10, Supplement 4.

Suh, et al., Characterization of His-X3-His Sites in a-Helices of Synthetic Metal-Binding Bovine Somatotropin, Protein Engineering, 1991, pp. 301-305, vol. 4, No. 3.

Sulbacher, et al., Activin A-Induced Differentiation of Embryonic Stem Cells into Endoderm and Pancreatic Progenitors—The Influence of Differentiation Factors and Culture Conditions, Stem Cell Rev, 2009, pp. 159-173, vol. 5.

Sun, et al., Feeder-Free Derivation of Induced Pluripotent Stem Cells from Adult Human Adipose Stem Cells, Proceedings and the National Academy of Sciences, 2009, pp. 15720-15725, vol. 106, No. 37.

Suzuken, Differentiation of Multifunctional Stem Cells Using Human Feeder Cells, Research Papers of the Suzuken Memorial Foundation, 2007, pp. 193-197, vol. 24, JP.

Swindle, et al., Swine in Biomedical Research: Management and Models, ILAR News, 1994, pp. 1-5, vol. 36, No. 1.

Takahashi, et al., Homogenous Seeding of Mesenchymal Stem Cells into Nonwoven Fabric for Tissue Engineering, Tissue Engineering, 2003, pp. 931-938, vol. 9, No. 5.

Takahashi, et al., Induction of Pluripotent Stem Cells from Adult Human Fibroblasts by Defined Factors, Cell, 2007, pp. 861-872, vol. 131.

Takehara, et al., Rho-Associate Kinase Inhibitor Y-27632 Promotes Survival of Cynomolgus Monkey Embryonic Stem Cells, Molecular Human Reproduction, 2008, pp. 627-634, vol. 14, No. 11.

Tang, et al., Reprogramming Liver-Stem WB Cells into Functional Insulin-Producing Cells by Persistent Expression of Pdx1- and Pdx1-VP16 Mediated by Lentiviral Vectors, Laboratory Investigation, 2006, pp. 83-93, vol. 86.

Tannock, et al., Chemotherapy with Mitoxantrone Plus Prednisone or Prednisone Alone for Symptomatic Hormone-Resistant Prostate Cancer: A Canadian Randomized Trial With Palliative End Points, Journal of Clinical Oncology, 1996, 1756-1764, 14-6, American Society of Clinical Oncology, US.

Teare, et al., Cellular Attachment to Ultraviolet Ozone Modified Polystyrene Surfaces, Langmuir, 2000, pp. 2818-2824, vol. 16.

Thermofisher Scientific, B-27 Serum-Free Supplement (50x) Liquid, Technical Resources, 2016, URL:https://www.thermofisher.com/nl/en/home/technical-resources/media-formulation.250.html, retrieved from the internet.

Thomson et al., Embryonic Stem Cell Lines Derived from Human Blastocysts, Science, Nov. 6, 1998, 1145-1147, 282, HighWire Press.

Thomson et al., Isolation of a primate embryonic stem cell line, Developmental Biology, Aug. 1995, 7844-7848, 92, Proc. Natl. Acad. Sci, US.

Thomson et al., Primate Embryonic Stem Cells, Currenl Topics in Developmental Biology, 1998, 133-154, 38, Academic Press, US.

Tomita, et al., Bone Marrow-Derived Stem Cells Can Differentiate into Retinal Cells in Injured Rat Retina, Stem Cells, 2002, pp. 279-283, vol. 20.

Totonchi, et al., Feeder- and Serum-Free Establishment and Expansion of Human Induced Pluripotent Stem Cells, Int. J. Dev. Biol., 2010, pp. 8770886, vol. 54.

Tsai, et al., Isolation of Human Multipotent Mesenchymal Stem Cells from Second-Trimester Amniotic Fluid Using a Novel Two-Stage Culture Protocol, Human Reproduction, Apr. 22, 2004, pp. 1450-1456, vol. 19, No. 6.

(56) References Cited

OTHER PUBLICATIONS

Tsuchida, et al., Activin Isoforms Signal Through Type I Receptor Serine/Threonin Kinase ALK7, Molecular and Cellular Endocrinology, 2004, pp. 59-65, vol. 22.
Tulachan et al., TGF-β isoform signaling regulates secondary transition and mesenchymal-induced endocrine development in the embryonic mouse pancreas, Developmental Biology, 2007, 508-521, 305, Elsevier.
Ubeda et al., Inhibition of Cyclin-dependent Kinase 5 Activity Protects Pancreatic Beta Cells from Glucotoxicity, Journal of Biological Chemistry, Aug. 3, 2006, 28858-28864, 39, JBC Papers in Press.
Uludag, et al., Technology of Mammalian Cell Encapsulation, Advanced Drug Delivery Reviews, 2000, pp. 29-64, vol. 42.
Ungrin, et al., Reproducible, Ultra High-Throughput Formation of Multicellular Organization from Single Cell Suspension-Derived Human Embryonic Stem Cell Aggregates, Plos ONE, 2008, e1565, pp. 1-12, vol. 3, Issue 2.
Unknown, MeSH Descriptor Data, National Library of Medicine—Medical Subject Headings, Feb. 26, 1992, XP002553615.
Unknown, Preserve the Stability of Your Stem Cells, Stem Cells, 2006, Internet Citation, XP002496166.
Vacanti, et al., Selective Cell Transplantation Using Bioabsorbable Artificial Polymers as Matrices, Journal of Pediactric Surgery, Jan. 1988, 3-9, 23-1.
Valet, et al., Pretherapeutic Identification of High-Risk Acute Myeloid Leukemia (AML) Patients from . . . , Clinical Cytometry, Feb. 17, 2003, 4-10, 53B, Wiley-Liss, Inc., US.
Vallier, et al., Activin/Nodal and FGF Pathways Cooperate to Maintain Pluripotency of Human Embryonic Stem Cells, Journal of Cell Sciences, 2005, pp. 4495-4509, vol. 118.
Van Der Greef et al., Rescuing drug discovery: In vivo systems pathology and systems pharmacology, Nature, Dec. 1, 2005, 961-967, 4-1, Nature Reviews, US.
Van Der Windt, et al., The Chioce of Anatomical Site for Islet Transplantation, Cell Transplantation, 2008, pp. 1005-1014, vol. 17.
Van Kooten, et al., Plasma-Treated Polystyrene Surfaces: Model Surfaces for Studying Cell-Biomaterial Interactions, Biomaterials, 2004, pp. 1735-1747, vol. 25.
Van Wachem, et al., Method for the Fast Application of an Evenly Distributed Cell Layer on Porous Vascular Grafts, Biomaterials, 1990, pp. 602-606, vol. 11.
Vanderford et al., Multiple kinases regulate mafA expression in the pancreatic beta cell line MIN6, Biochemistry and Biophysics, 2008, 138-142, 480, Elsevier.
Verfaillie, et al., Stem Cells: Hype and Reality, Hematology, 2002, pp. 369-391.
Vieira, et al., Modulation of Neuronal Stem Cell Differentiation by Hypoxia and Reactive Oxygen Species, Progress in Neurobiology, 2011, pp. 444-455, vol. 93.
Vodicka, et al., The Miniature Pig as an Animal Model in Biomedical Research, Annals New York Academy of Sciences, 2005, pp. 161-171, vol. 1049.
Vunjak-Novakovic, et al., Dynamic Cell Seeding of Polymer Scaffolds for Cartilage Tissue Engineering, Biotechnology Program, 1998, pp. 193-202, vol. 14, Issue 2.
Wachs, et al., High Efficacy of Clonal Growth and Expansion of Adult Neural Stem Cells, Laboratory Investigation, 2003, pp. 949-962, vol. 83, No. 7.
Wang et al., Derivation and Growing Human Embryonic Stem Cells on Feeders Derived from Themselves, Stem Cells, 2005, 1221-1227, 23, AlphaMed Press.
Wang et al., Relationship of Chemical Structurs of Anthraquinones with their Effects onthe Suppression of Immune Responses, International Journal of Immunopharmacology, 1987, 733-739, 9-6, International Society for Immunopharmacology, GB.
Wang, et al., Noggin and bFGF Cooperate to Maintain the Pluripotency of Human Embryonic Stem Cells in the Absence of Feeder Layers, Biochemical and Biophysical Research Communications, 2005, pp. 934-942, vol. 33, No. 3.
Wang, et al., Three-Dimensional Differentiation of Embryonic Stem Cells into islet-Like Insulin-Producing Clusters, Tissue Engineering: Part A, 2009, pp. 1941-1952, vol. 15, No. 8.
Want, et al., Large-Scale Expansion and Exploitation of Pluripotent Stem Cells for Regenerative Medicine Purposes: beyond the T Flask, Loughborough University Institutional Repository, 2012, pp. 71-84, vol. 7, Issue 1.
Watanabe, et al., A Rock Inhibitor Permits Survival of Dissociated Human Embryonic Stem Cells, Nature Biotechnology, 2007, pp. 681-686, vol. 25, No. 6.
Wei et al., Cdk5-dependent regulation of glucose-stimulated insulin secretion, Nature Medicine, Sep. 11, 2005, 1104-1108, 11-10, Nature Publishing Group.
Wei, et al., Human Amnion-Isolated Cells Normalize Blood Glucose in Strepozotocin Induced Diabetic Mice, Cell Transplantation, 2003, pp. 545-552, vol. 12, No. 5.
Wei, et al., Transcriptome Profiling of Human and Murine ESCs Identifies Divergent Paths Required to Maintain the Stem Cell State, Stem Cells, 2005, pp. 166-185, vol. 23.
Wells, et al., Early Mouse Endoderm is Patterned by Soluble Factors from Adjacent Germ Layers, Development, 2000, pp. 1563-1572, vol. 127, Issue 8.
Wernig, et al., c-Myc is Dispensable for Direct Reprogramming of Mouse Fibroblasts, Cell Stem Cell, Jan. 2008, pp. 10-12, vol. 2.
White, et al., Complex Regulation of cyp26a1 Creates a Robust Retinoic Acid Gradient in the Zebrafish Embryo, PLOS Biology, 2007, pp. 2522-2533, vol. 5, Issue 11.
Wiles et al., Embryonic Stem Cell Development in a Chemically Defined Medium, Experimental Cell Research, 1999, 241-248, 247, Academic Press.
Wilson, et al., The HMG Box Transcription Factor Sox4 Contributes to the Development of the Endcrine Pancreas, Diabetes, 2005, pp. 3402-4309, vol. 54, Issue 12.
Wong, et al., Directed Differentiation of Human Pluripotent Stem Cells into Mature Airway Epithelia Expressing Functional CFTR Protein, Nature Biotechnology, 2012, pp. 876-884, vol. 30, No. 9.
XP002553616_1989, RecName: Full=Inhibin beta B Chain; AltName: Full=Activin beta-B chain; Flags; Precurso, Database UniProt [Online], Jul. 1, 1989, Database Accession No. P09529, EBI Accession No. Uniprot: P09529.
Xu et al., Immortalized Fibroblast-Like Cells Derived from Human Embryonic Stem Cells Support Undifferentiated Cell Growth, Stem Cells, 2004, 972-980, 22, AlphaMed Press.
Xu et al., Basic FGF and Suppression of BMP Signalling Sustain Undifferentiated Proliferation of Human ES Cells, Nature Methods, 2005, pp. 185-189, vol. 2, Issue 3.
Xu, et al., Feeder-free Growth of Undifferentiated Human Embryonic Stem Cells, Nature Biotechnology, 2001, pp. 971-974, vol. 19.
Xudong, et al., Research Progress in Inducing Stem Cels to Differentiate toward the B-like Cells of Pancreatic Islet, Chinese Bulletin of Life Sciences, 2007, pp. 526-530, vol. 19, No. 5.
Yang et al., Novel cell immobilization method utilizing centrifugal force to achieve high-density hepatocyte culture in porous scaffold, Journal of Biomed Materials Research, Feb. 27, 2001, 379-386, 55, John Wiley & Sons, Inc.
Yang, et al., Evaluation of Humam MSCs Cell Cycle, Viability and Differentiation in Micromass Culture, Biorheology, 2006, p. 489-496, vol. 43.
Yang, et al., Survival of Pancreatic Islet Xenografts in NOD Mice with the Theracyte Device, Transplantation Proceedings, 2002, pp. 3349-3350, vol. 34.
Yasuda, et al., Development of Cystic Embryoid Bodies with Visceral Yolk-Sac-Like Structures from Mouse Embryonic Stem Cells Using Low-Adherence 96-Well Plate, Journal of Bioscience and Bioengineering, Apr. 4, 2009, pp. 442-446, vol. 107, No. 4.
Yoneda, et al., The RHO Kinases I and II Regulate Different Aspects of Myosin II Acitivity, The Journal of Cell Biology, 2005, pp. 443-445, vol. 170, No. 3.
Young, et al., Three-Dimensional Culture of Human Uterine Smooth Muscle Nyocytes on a Resorbably Scaffolding, Tissue Engineering, 2003, pp. 451-459, vol. 9, No. 3.

(56) References Cited

OTHER PUBLICATIONS

Yu, et al., Induced Pluripotent Stem Cell Lines Derived from Human Somatic Cells, Science, Dec. 21, 2007, pp. 1917-1920, vol. 318.
Yu, et al., Isolation of a Novel Population of Multipotent Adult Stem Cells from Human Hair Follicles, American Journal of Pathology, Jun. 6, 2006, pp. 1879-1888, vol. 168, No. 6.
Zalzman, et al., Differentiation of Human Liver-Derived, Insulin-Producing Cells Toward the B-Cell Phenotype, Diabetes, 2005, pp. 2568-2575, vol. 54.
Zembower, et al., Peptide Boronic Acids Versatile Synthetic Ligands for Affinity Chromatography of Serine Proteinases, International Journal Peptide Protein, 1996, pp. 405-413, vol. 47.
Zhang et al., MafA Is a Key Regulator of Glucose-Stimulated Insulin Secretion, Molecular and Cellular Biology, Jun. 2005, 4969-4976, 25-12, American Society for Microbiology.
Zhang, et al., Differentiation Potential of Bone Marrow Mesenchymal Stem Cells into Retina in Normal and Laser-Injured Rat Eye, Science in China Series, 2004, pp. 241-250, vol. 47, No. 3.
Zhang, Jie, The Differentiation of Bone Marrow Mesenchymal Stem Cells into Retina in Rat Eye and the Therapeutical Effect on Severe Injured Retina, A Doctoral Thesis of Chinese PLA Acadamey of Military Medical Sciences, 2003, 1-127, 1-127.
Zhang_et al, Highly Efficient Differentiation of Human ES Cells and iPS Cells into Mature Pancreatic Insulin-Producing Cells, Cell Research, 2009, pp. 429-438, vol. 19, Issue 14.
Zhao et al., The Islet B Cell-enriched MafA Activator is a Key Regulator of Insulin Gene Transcription, Journal of Biological Chemistry, Mar. 25, 2005, 11887-11894, 280-12, The Amerian Society for Biochemistry and molecular Biology, Inc.
Zhao, et al., Derivation and Characterization of Hepatic Progenitor Cells from Human Embryonic Stem Cells, PLoS ONE Hepatic Progenitors from hESCs, Jul. 2009, e6468 pp. 1-10, vol. 4, Issue 7.
Zorn, et al., Vertebrate Endoderm Development and Organ Formation, Annual Review Cell Development Biology, 2009, pp. 221-251, vol. 25.
Zubaty, et al., Transplantation of Mesenchymal Stem Cells into RCS Rats for Retinal Repair, Investigative Ophthalmology and Visual Science, 2005, pp. 4160-B518, vol. 46, Supplement S.
Zuscik, et al., Regulation of Chondrogenesis and Chondrocyte Differentiation by Stress, J Clin Invest, 2008, pp. 429-438, vol. 118, Issue 2.

\* cited by examiner

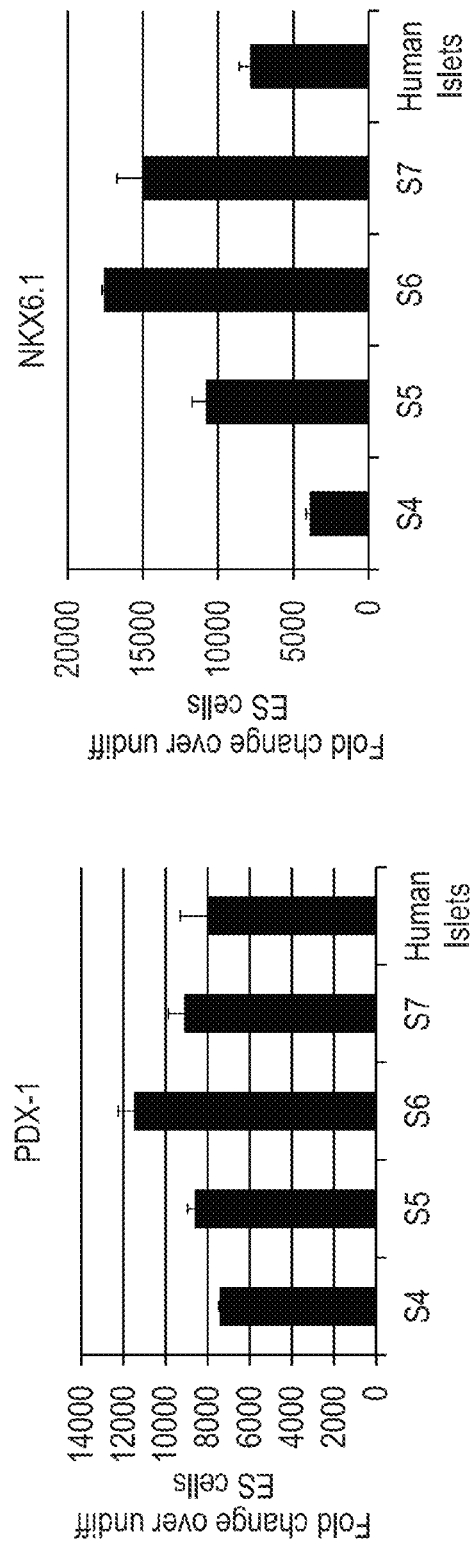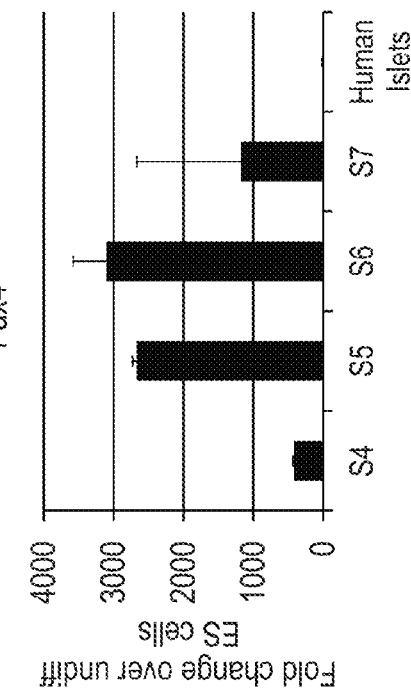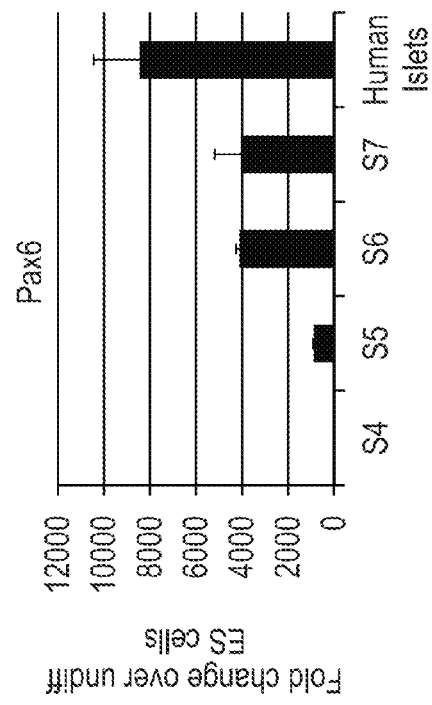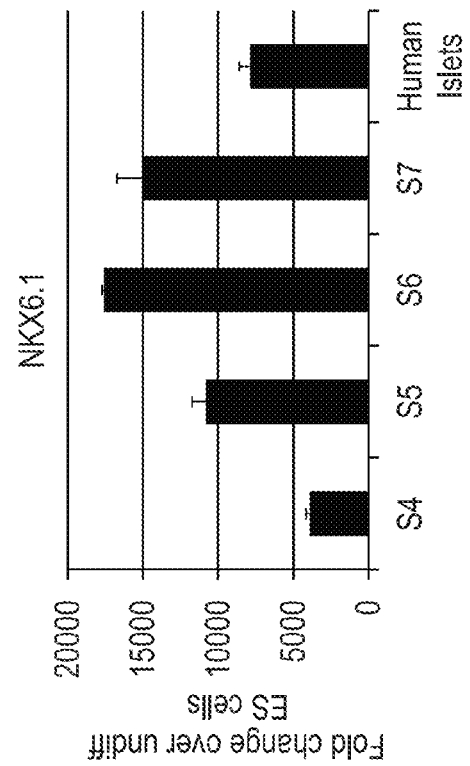

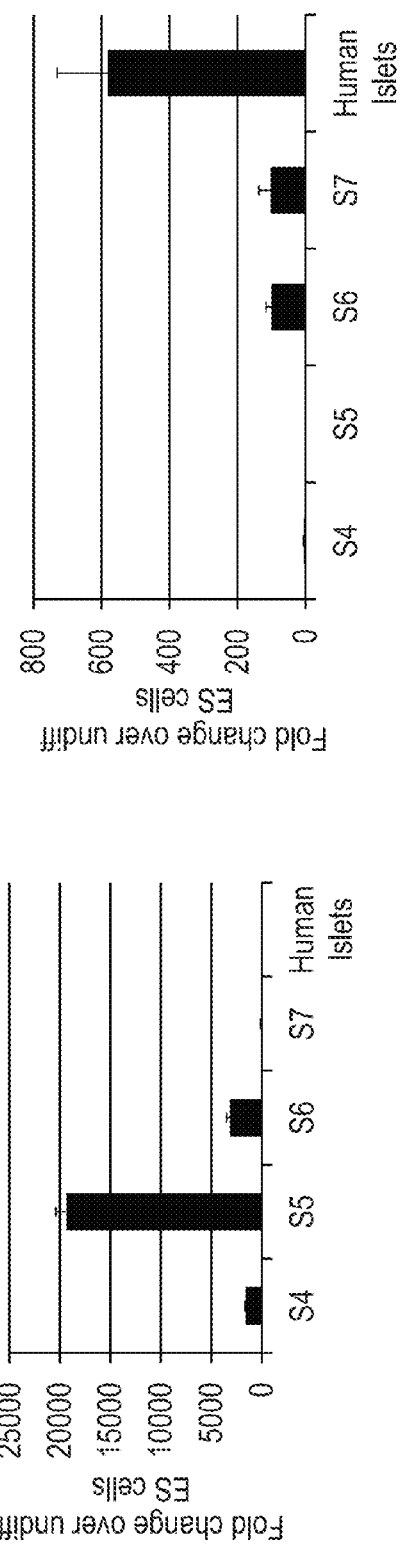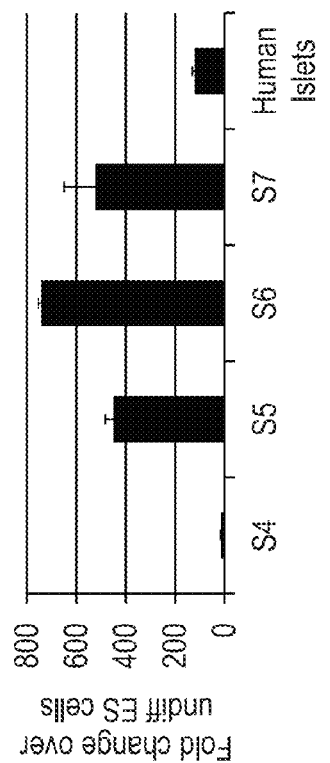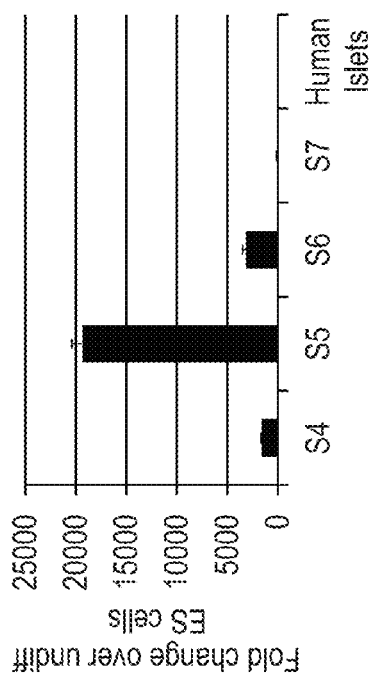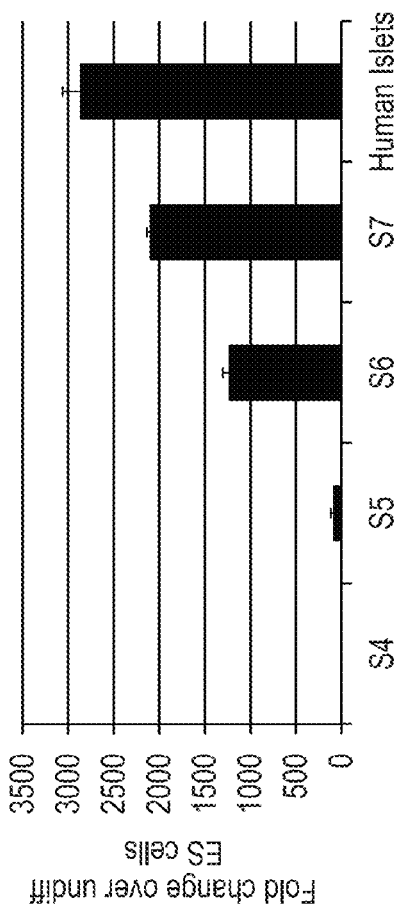
FIG. 1E NGN3
FIG. 1F MAFA
FIG. 1G ABCC8
FIG. 1H Chromogranin-A

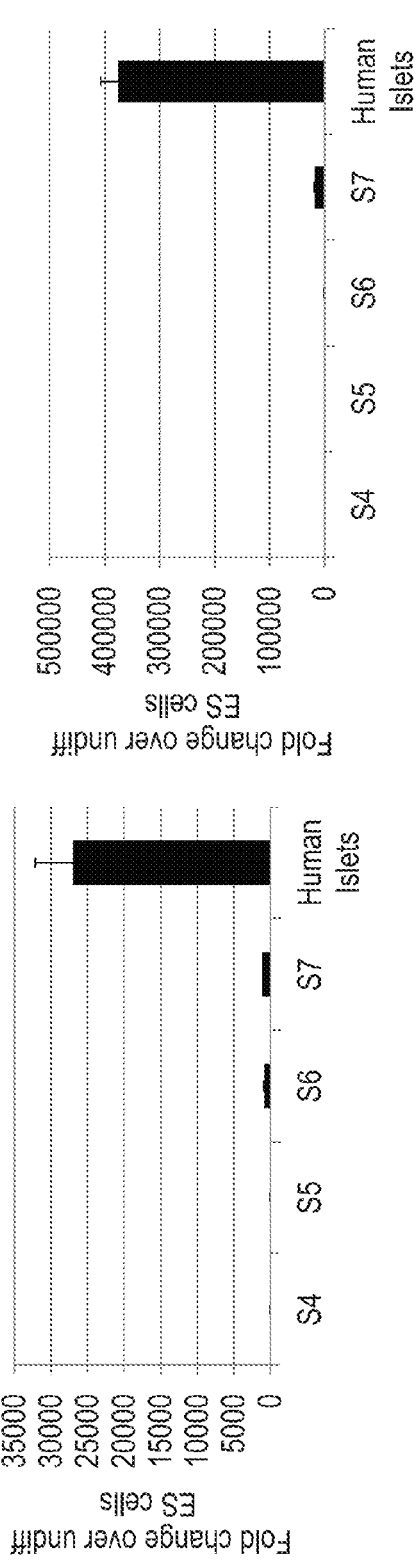

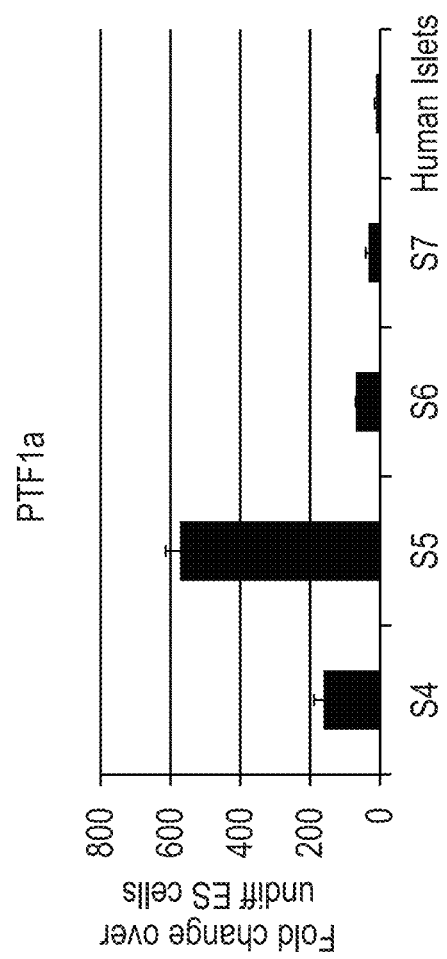

Stage 3

Stage 3

Stage 3

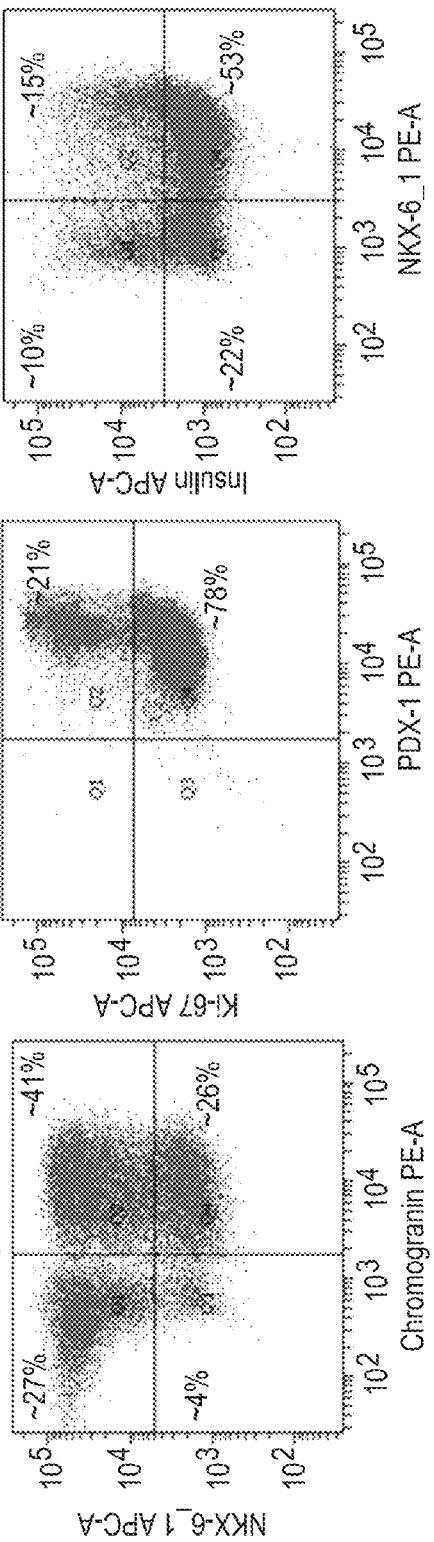
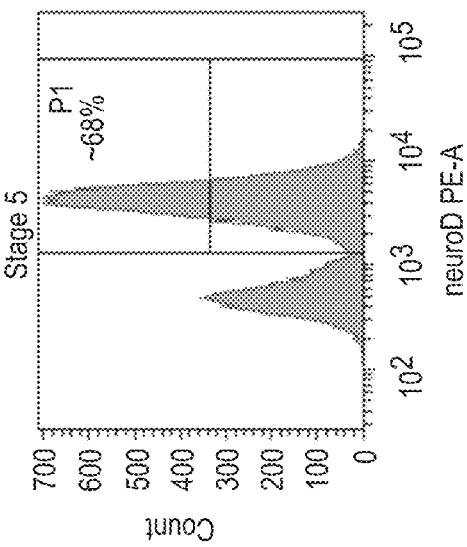
FIG. 4A, FIG. 4B, FIG. 4C, FIG. 4D, FIG. 4E

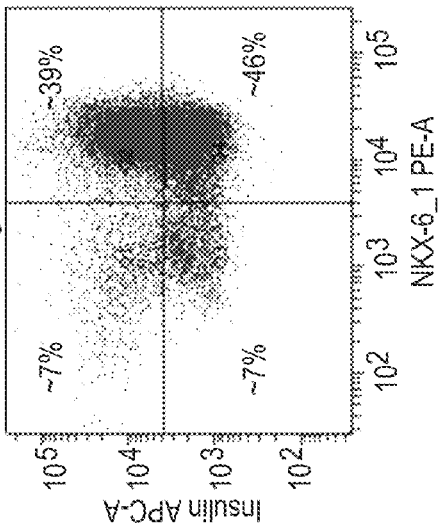
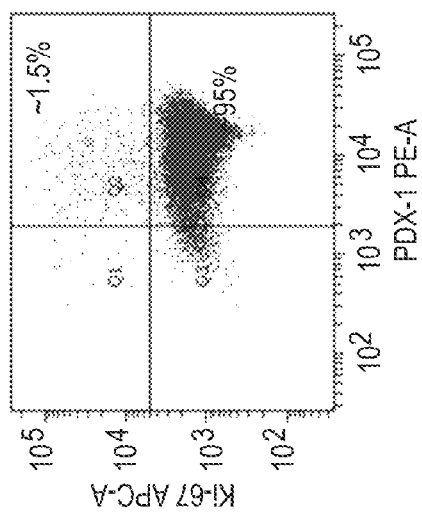
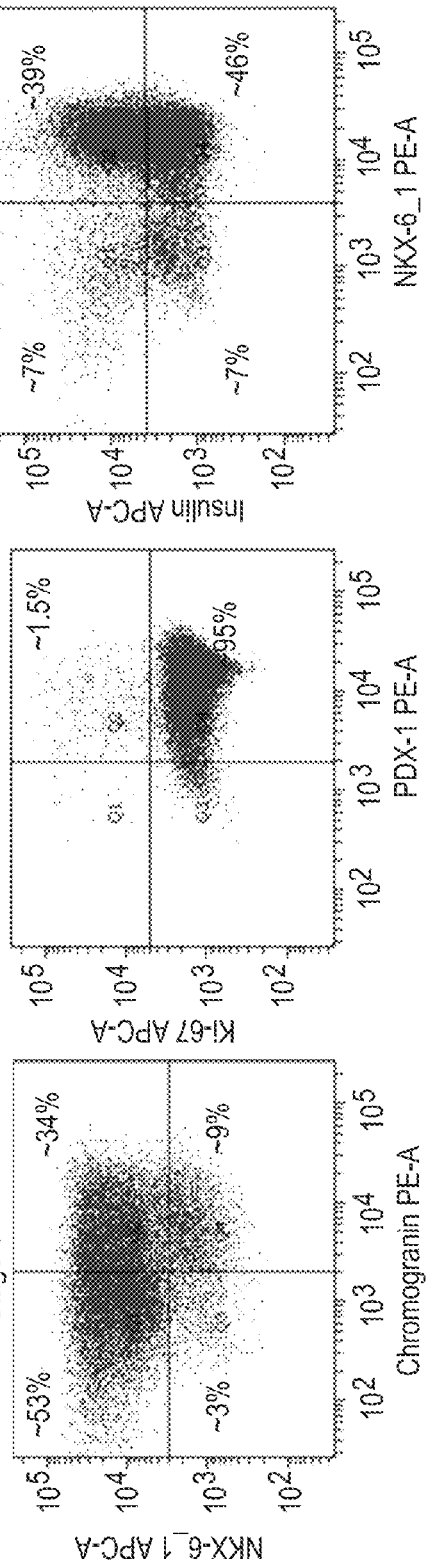
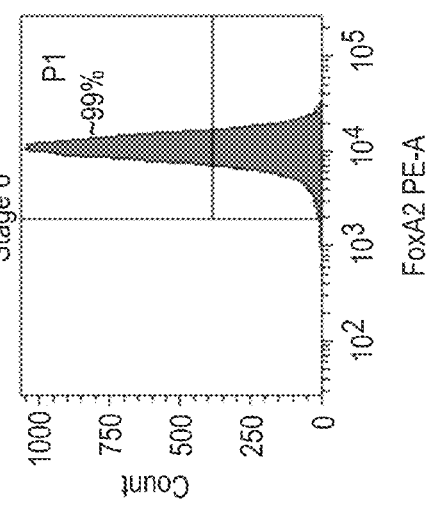
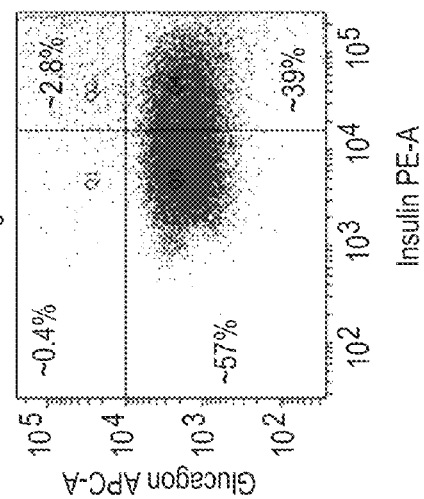
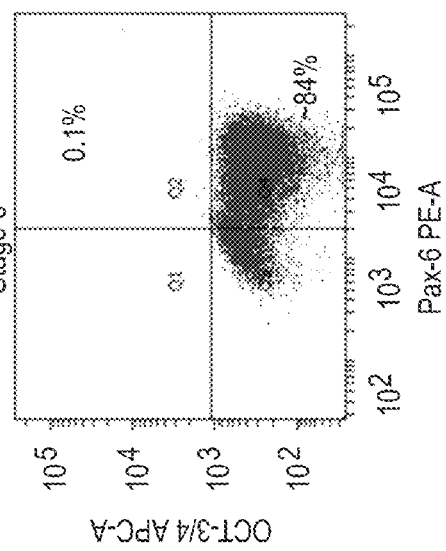

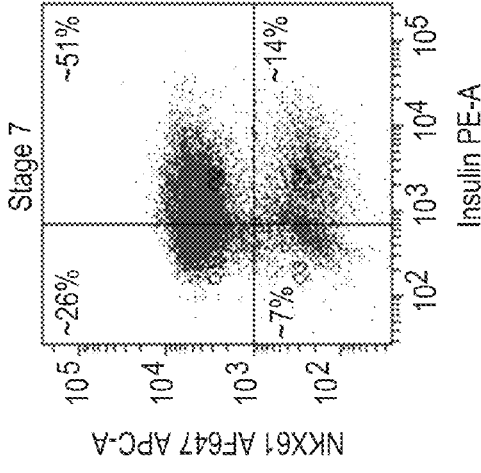
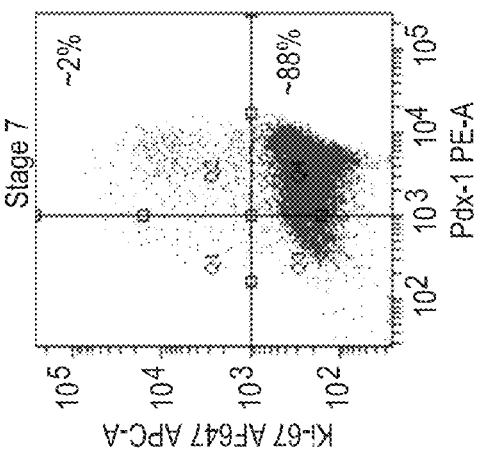
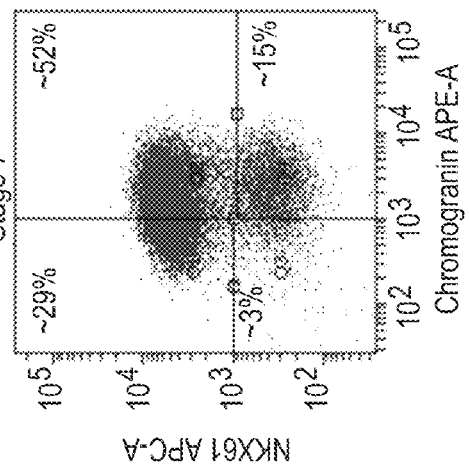
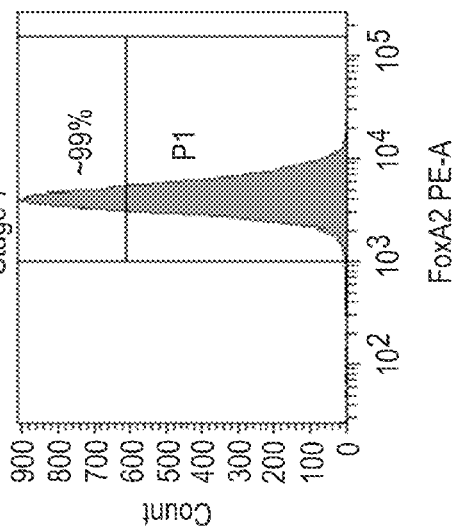
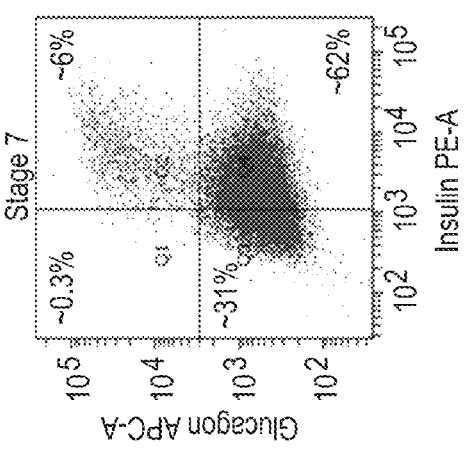
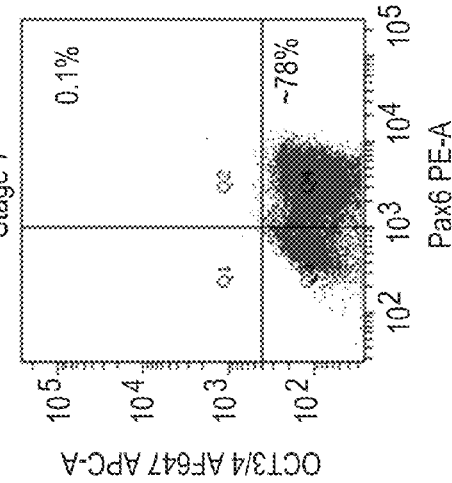

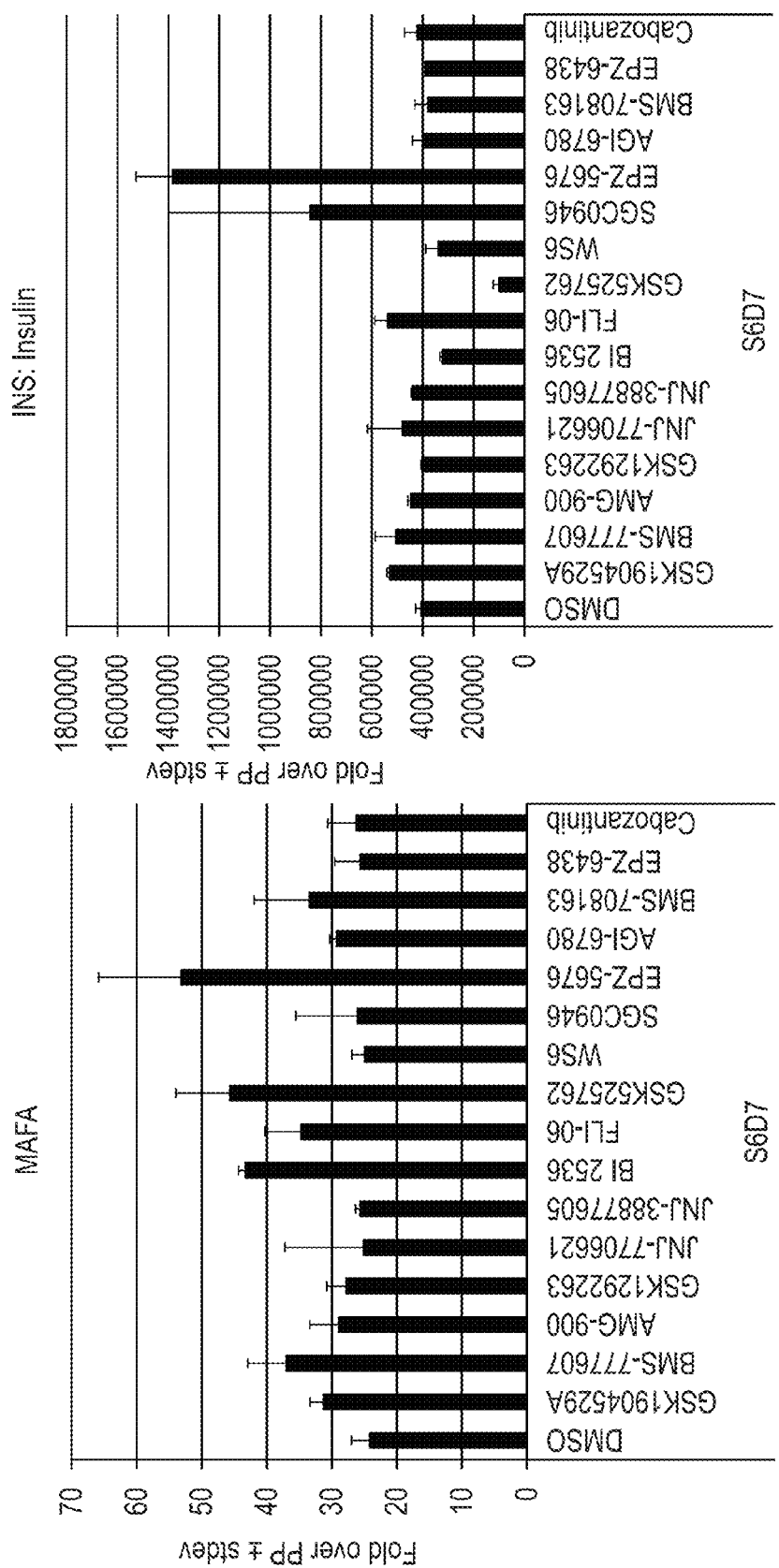

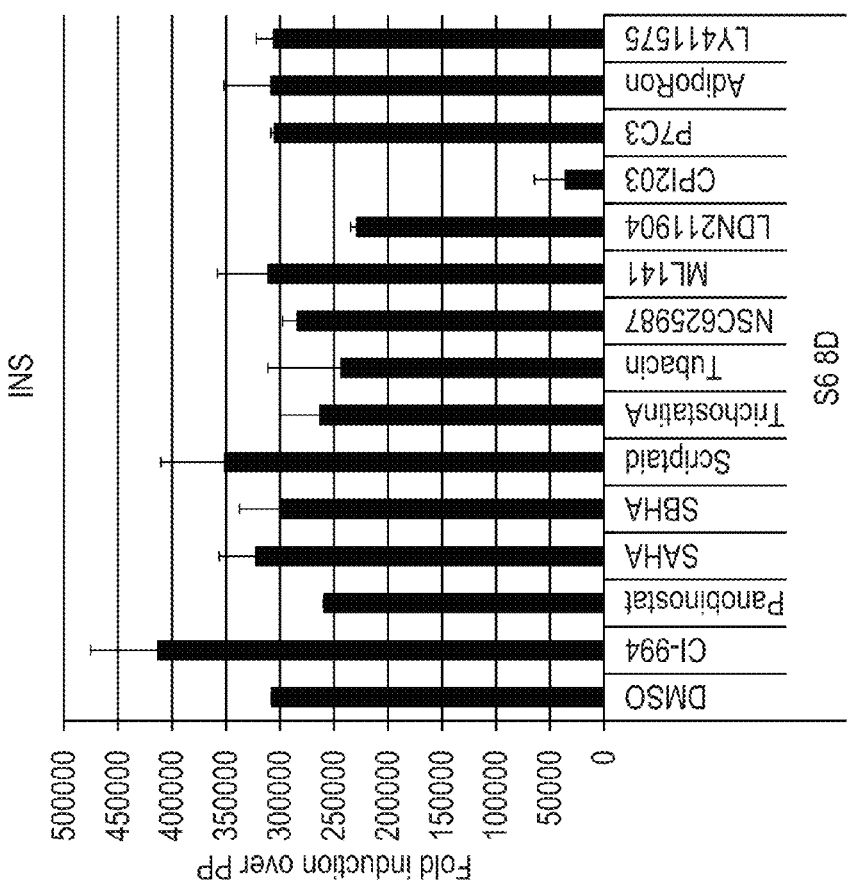
FIG. 8C MAFA
FIG. 8D INS
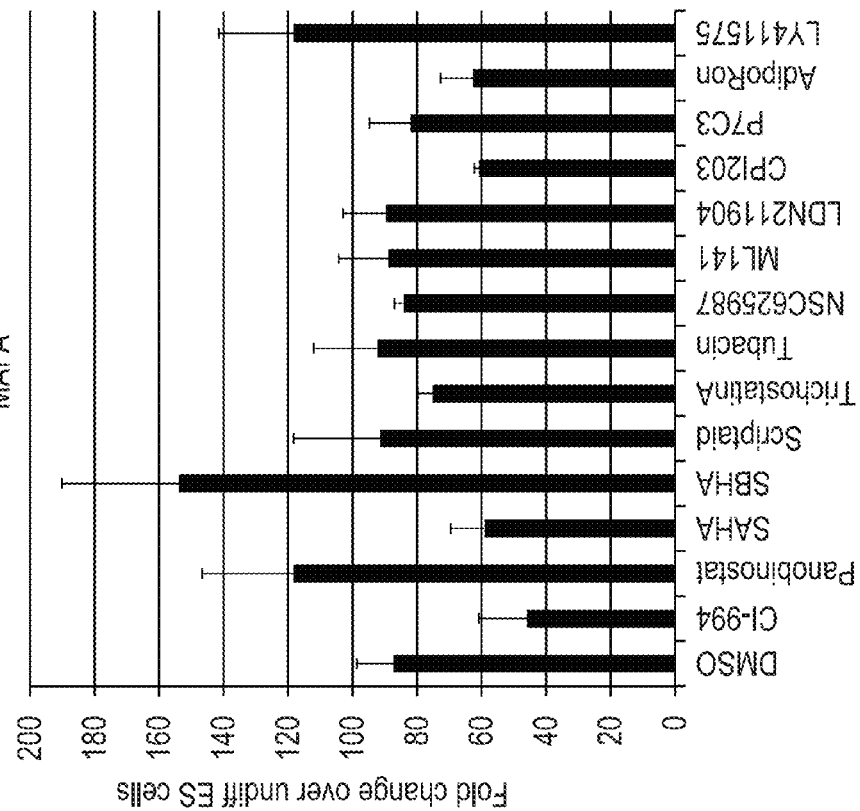

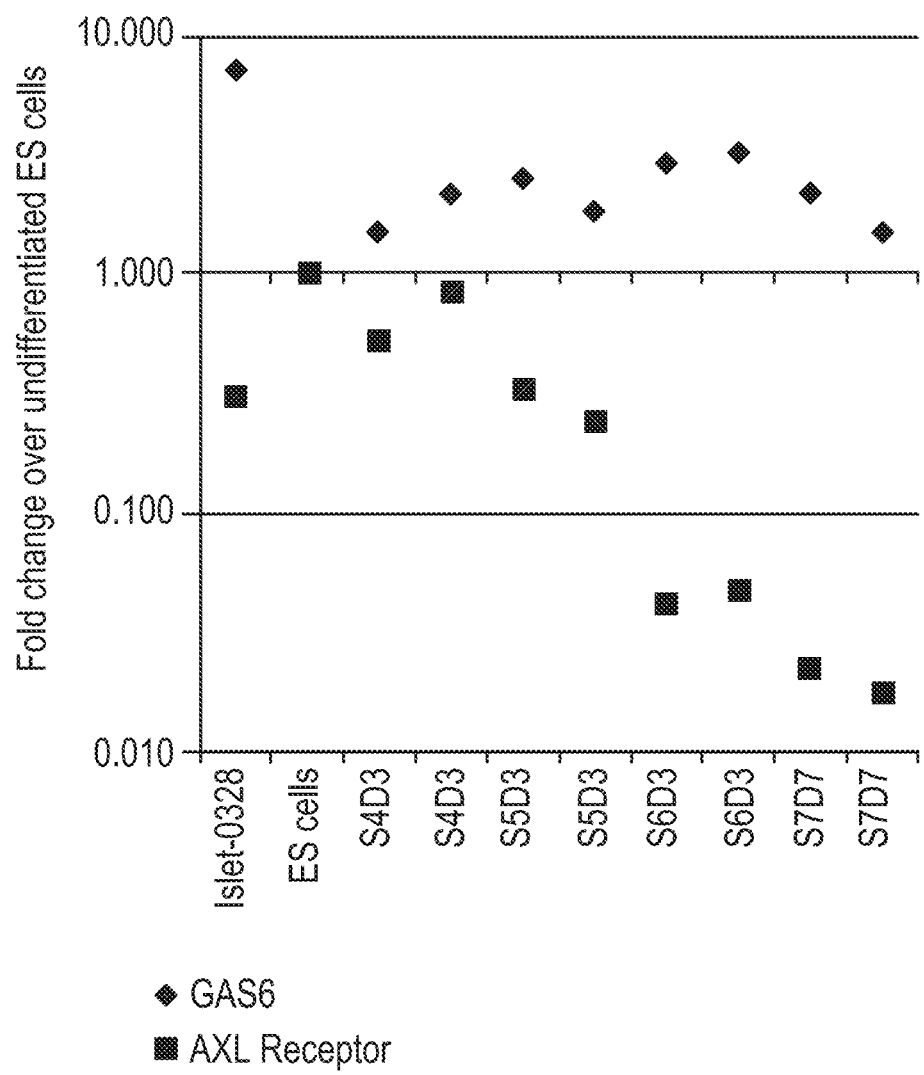

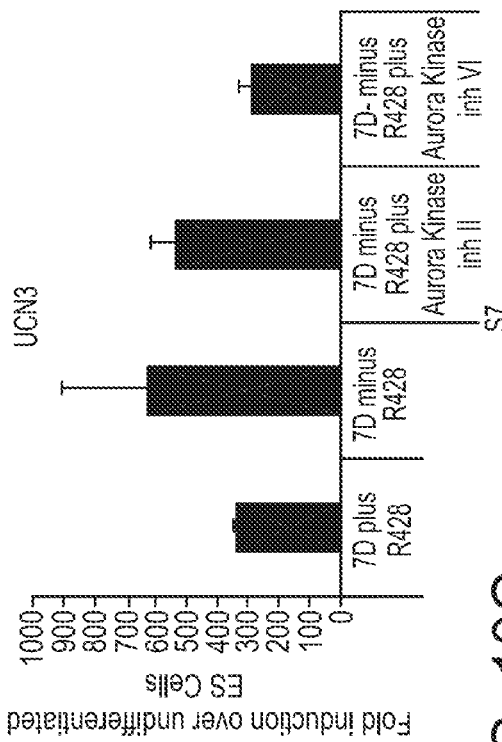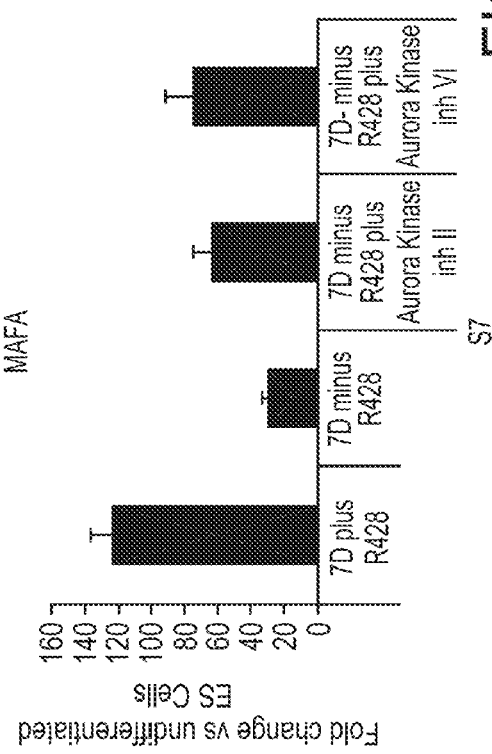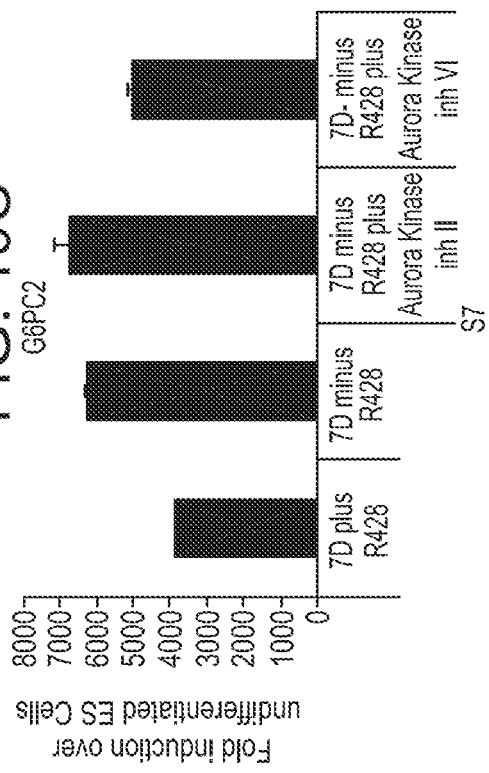

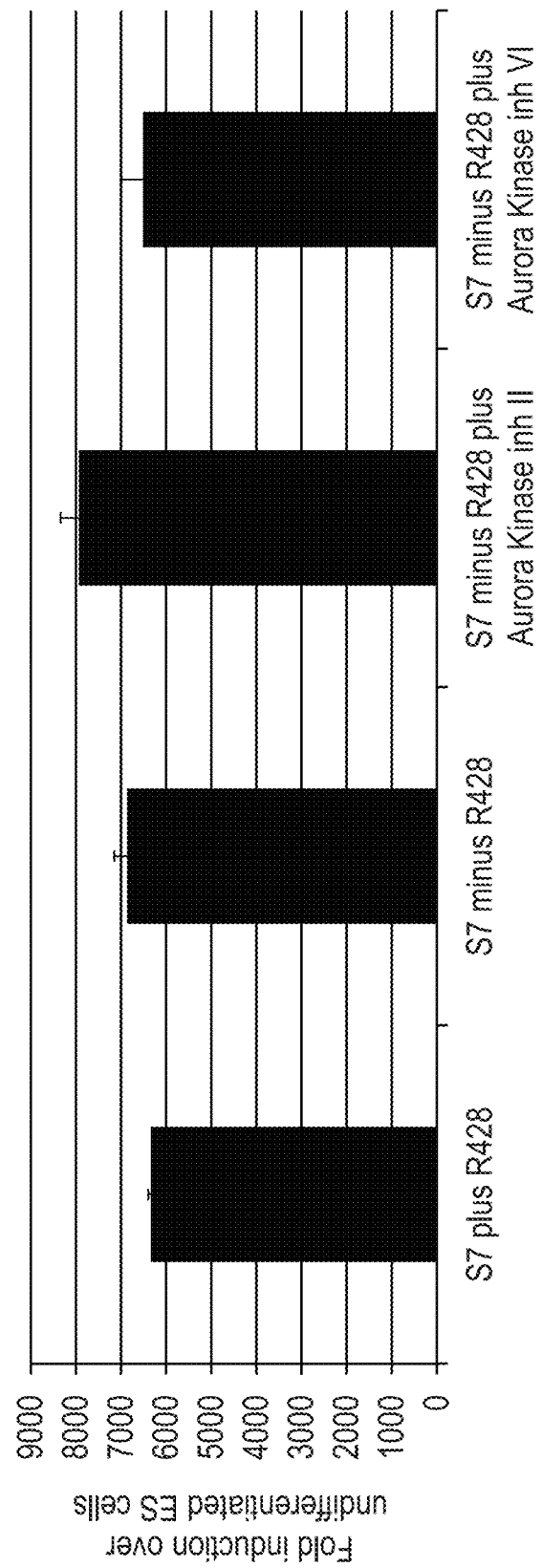

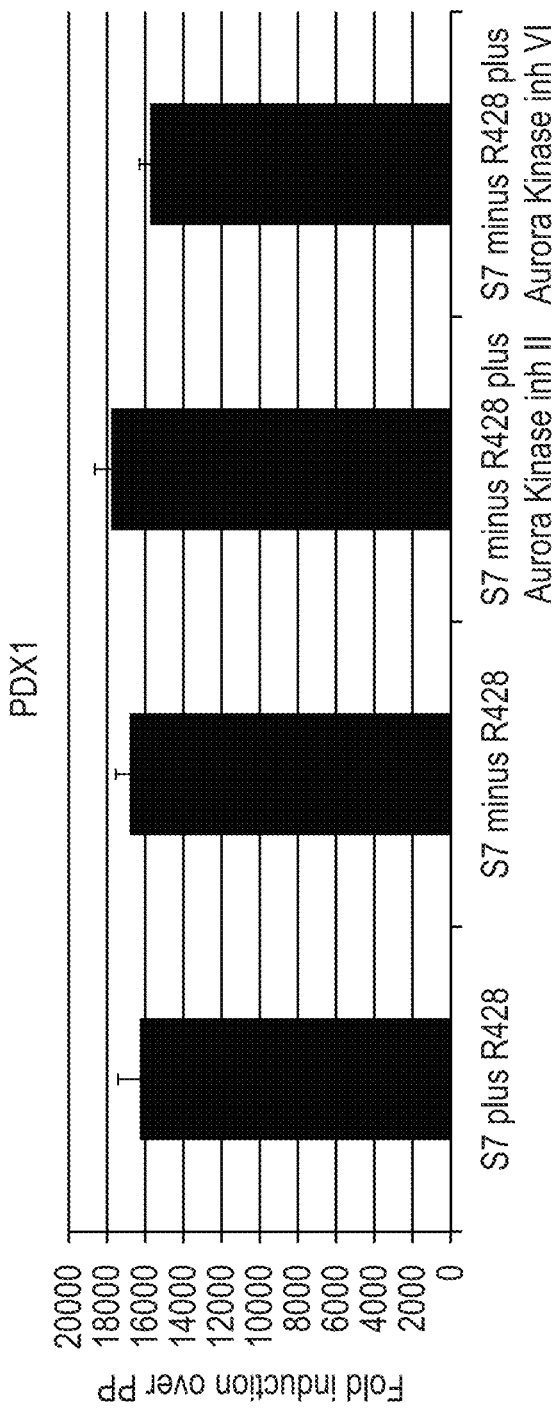

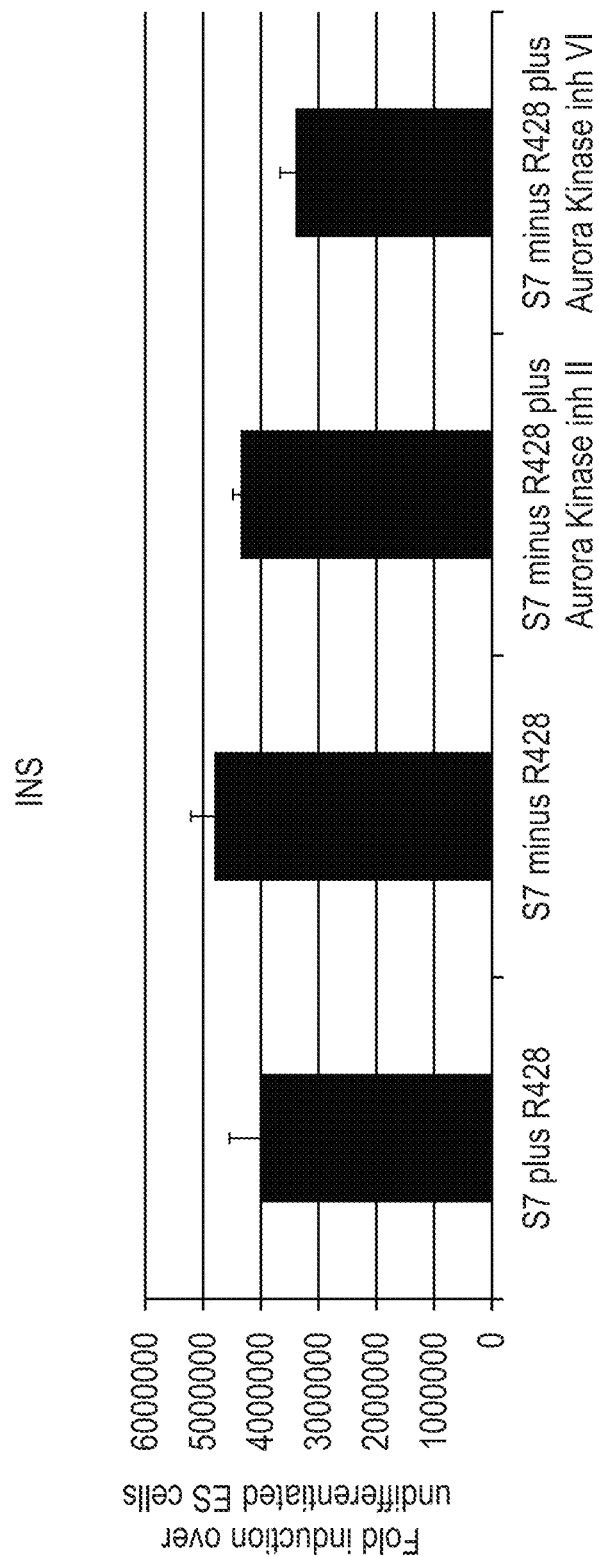

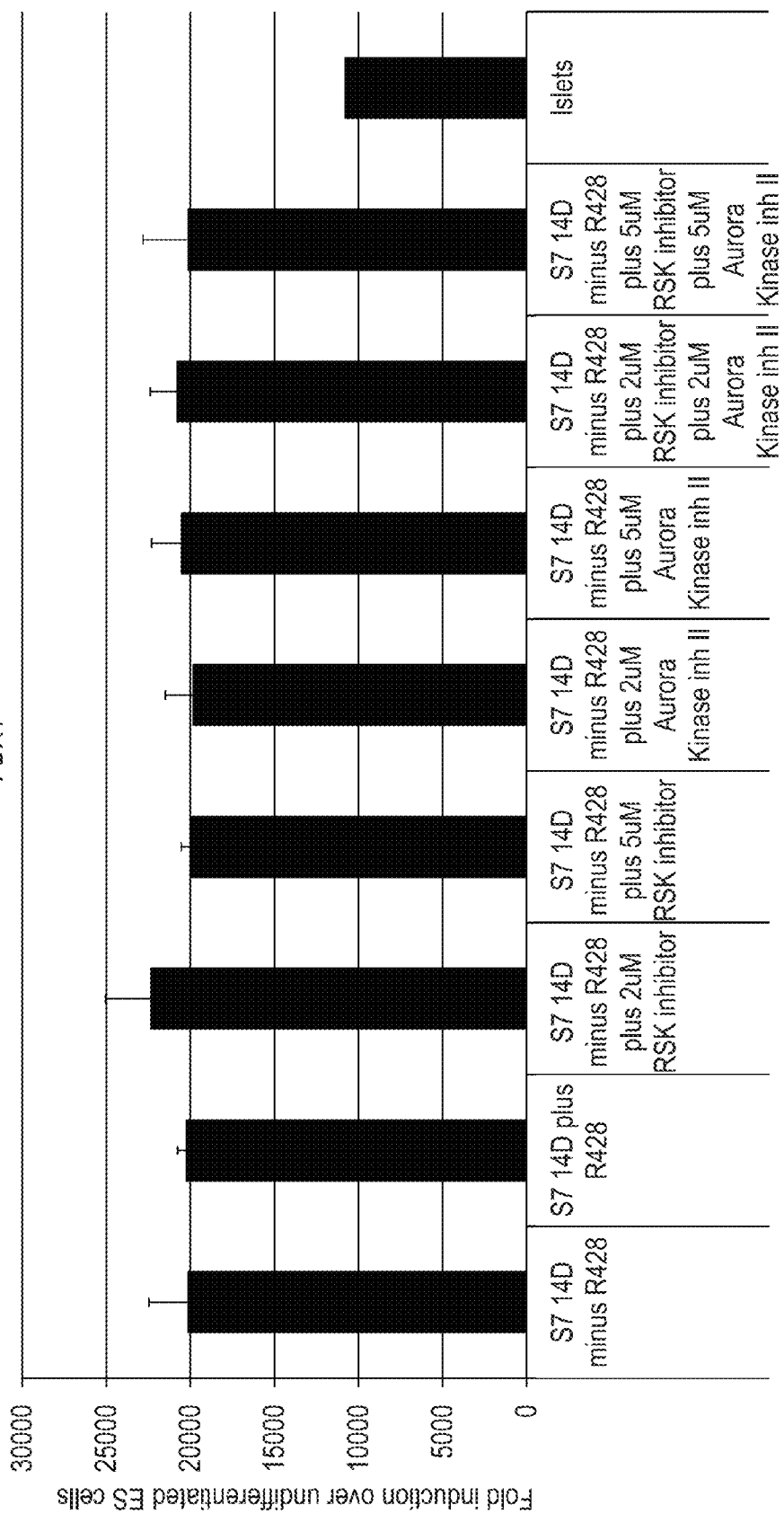

NKX6.1

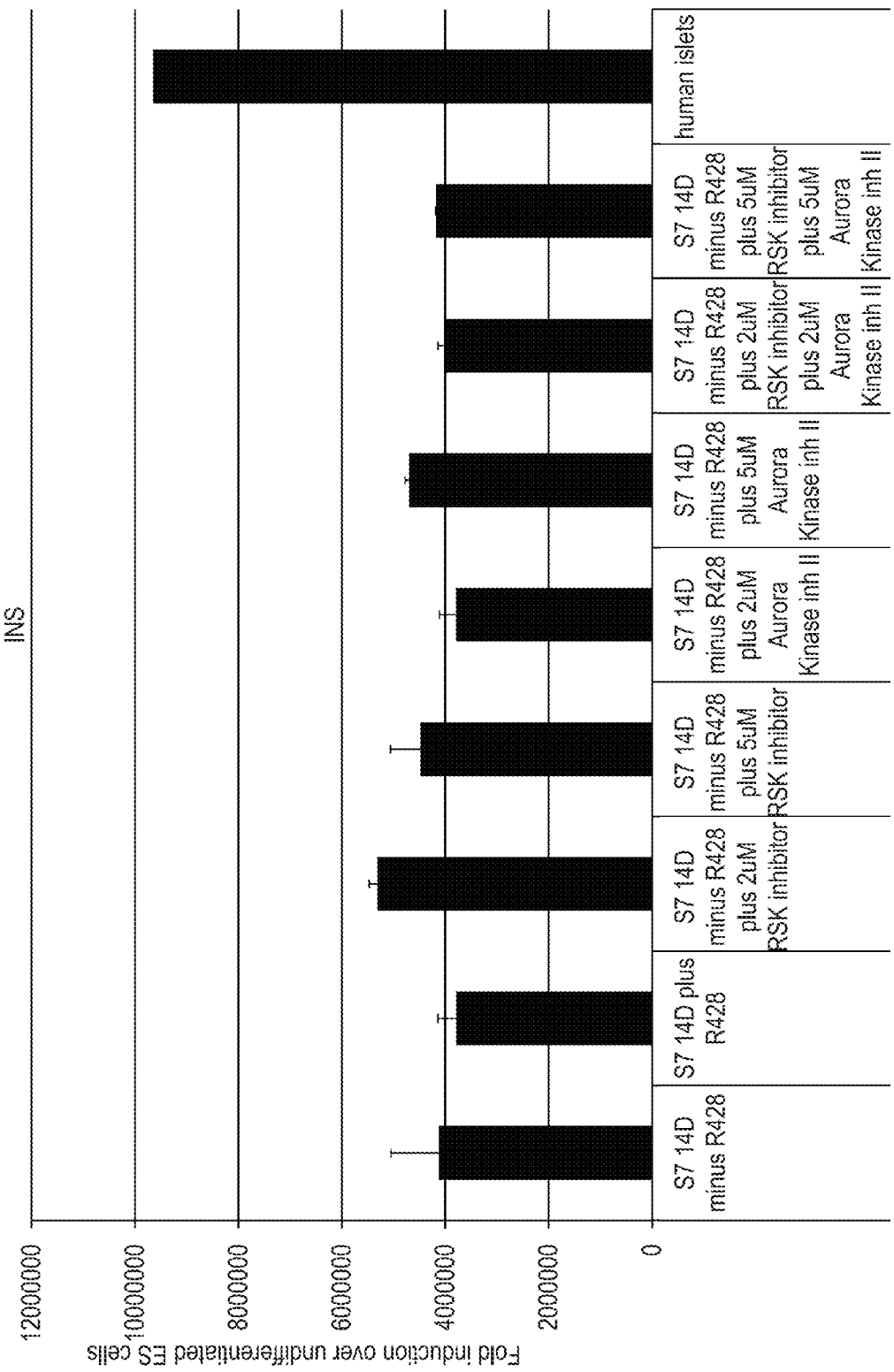

USE OF SMALL MOLECULES TO ENHANCE MAFA EXPRESSION IN PANCREATIC ENDOCRINE CELLS

CROSS REFERENCE TO RELATED APPLICATION

The present application claims the benefit of U.S. Provisional Patent Application Ser. No. 61/994,259, filed May 16, 2014, which is incorporated herein by reference in its entirety for all purpose.

FIELD OF THE INVENTION

The present invention relates to methods for, and cells and populations resulting from, the differentiation of pluripotent stem cells. In particular, the invention relates to the use of certain small molecules to generate pancreatic endocrine cells, and populations of such cells, that exhibit increased expression of MAFA.

BACKGROUND

Advances in cell-replacement therapy for Type I diabetes mellitus and a shortage of transplantable islets of Langerhans have focused interest on developing sources of insulin-producing cells, or beta (β) cells, appropriate for engraftment. One approach is the generation of functional β cells from pluripotent stem cells, such as, embryonic stem cells.

In vertebrate embryonic development, a pluripotent cell gives rise to a group of cells comprising three germ layers (ectoderm, mesoderm, and endoderm) in a process known as gastrulation. Tissues such as, thyroid, thymus, pancreas, gut, and liver will develop from the endoderm via an intermediate stage. The intermediate stage in this process is the formation of definitive endoderm.

By the end of gastrulation, the endoderm is partitioned into anterior-posterior domains that can be recognized by the expression of a panel of factors that uniquely mark anterior, mid, and posterior regions of the endoderm. For example, HHEX, and SOX2 identify the anterior region while CDX1, 2, and 4 identify the posterior region of the endoderm.

Migration of endoderm tissue brings the endoderm into close proximity with different mesodermal tissues that help in regionalization of the gut tube. This is accomplished by a plethora of secreted factors, such as fibroblast growth factors ("FGFs"), WNTS, transforming growth factor betas ("TGF-βs"), retinoic acid, and bone morphogenic protein ("BMP") ligands and their antagonists. For example, FGF4 and BMP promote CDX2 expression in the presumptive hindgut endoderm and repress expression of the anterior genes HHEX and SOX2 (2000 Development, 127:1563-1567). WNT signaling has also been shown to work in parallel to FGF signaling to promote hindgut development and inhibit foregut fate (2007 Development, 134:2207-2217). Lastly, secreted retinoic acid by mesenchyme regulates the foregut-hindgut boundary (2002 Curr. Biol., 12:1215-1220).

The level of expression of specific transcription factors may be used to designate the identity of a tissue. During transformation of the definitive endoderm into a primitive gut tube, the gut tube becomes regionalized into broad domains that can be observed at the molecular level by restricted gene expression patterns. The regionalized pancreas domain in the gut tube shows a very high expression of PDX and very low expression of CDX2 and SOX2. PDX1, NKX6.1/PTF1A, and NKX2.2 are highly expressed in pancreatic tissue and expression of CDX2 is high in intestinal tissue.

Formation of the pancreas arises from the differentiation of definitive endoderm into pancreatic endoderm. Dorsal and ventral pancreatic domains arise from the foregut epithelium. Foregut also gives rise to the esophagus, trachea, lungs, thyroid, stomach, liver, and bile duct system.

Cells of the pancreatic endoderm express the pancreatic-duodenal homeobox gene PDX1. In the absence of PDX1, the pancreas fails to develop beyond the formation of ventral and dorsal buds. Thus, PDX1 expression marks a critical step in pancreatic organogenesis. The mature pancreas contains both exocrine and endocrine tissues arising from the differentiation of pancreatic endoderm.

D'Amour et al. describe the production of enriched cultures of human embryonic stem cell-derived definitive endoderm in the presence of a high concentration of activin and low serum (*Nature Biotechnology* 2005, 23:1534-1541; U.S. Pat. No. 7,704,738). Transplanting these cells under the kidney capsule of mice resulted in differentiation into more mature cells with characteristics of endodermal tissue (U.S. Pat. No. 7,704,738). Human embryonic stem cell-derived definitive endoderm cells can be further differentiated into PDX1 positive cells after addition of FGF-10 and retinoic acid (U.S. Patent App. Pub. No. 2005/0266554). Subsequent transplantation of these pancreatic precursor cells in the fat pad of immune deficient mice resulted in the formation of functional pancreatic endocrine cells following a 3-4 months maturation phase (U.S. Pat. Nos. 7,534,608 and 7,993,920).

Fisk et al. report a system for producing pancreatic islet cells from human embryonic stem cells (U.S. Pat. No. 7,033,831). In this case, the differentiation pathway was divided into three stages. Human embryonic stem cells were first differentiated to endoderm using a combination of sodium butyrate and activin A (U.S. Pat. No. 7,326,572). The cells were then cultured with BMP antagonists, such as Noggin, in combination with EGF or betacellulin to generate PDX1 positive cells. The terminal differentiation was induced by nicotinamide.

Small molecule inhibitors have also been used for induction of pancreatic endocrine precursor cells. For example, small molecule inhibitors of TGF-β receptor and BMP receptors (*Development* 2011, 138:861-871; *Diabetes* 2011, 60:239-247) have been used to significantly enhance the number of pancreatic endocrine cells. In addition, small molecule activators have also been used to generate definitive endoderm cells or pancreatic precursor cells (*Curr. Opin. Cell Biol.* 2009, 21:727-732; *Nature Chem. Biol.* 2009, 5:258-265).

HB9 (also known as H1XB9 and MNX1) is a basic helix-loop-helix ("bHLH") transcriptional activator protein expressed early in pancreas development starting at approximately embryonic day eight. Expression of HB9 is transient and peaks at about day 10.5 in pancreatic epithelium, being expressed in PDX1 and NKX6.1 expressing cells. At about day 12.5, HB9 expression declines and at later stages it becomes restricted only to β cells. In mice homozygous for a null mutation of HB9, the dorsal lobe of the pancreas fails to develop (*Nat. Genet.* 23:67-70, 1999; *Nat. Genet.* 23:71-75, 1999). HB9-/β-cells express low levels of the glucose transporter, GLUT2, and NKX6.1. Furthermore, HB9-/- pancreas shows a significant reduction in the number of insulin positive cells while not significantly affecting expression of other pancreatic hormones. Thus, temporal control of HB9 is essential to normal β cell development and function. While not much is known about factors regulating HB9 expression in β cells, a recent study in zebrafish suggests that retinoic acid can positively regulate expression of HB9 (*Development*, 138, 4597-4608, 2011).

In U.S. patent application Ser. No. 13/998,883, incorporated herein in its entirety by reference, it was demonstrated that triiodothyronine ("T3") may act as an inducer of HB9 protein expression in differentiating cells toward β cells. Methods for generating pancreatic endoderm cells that were positive for NKX6.1, PDX1 and HB9 using of one or both of T3 and T4 are also disclosed therein. Additionally, and as disclosed in U.S. patent application Ser. No. 13/998,884, incorporated herein in its entirety by reference, it was demonstrated that expression of pancreatic endocrine markers can be significantly enhanced by culturing at the air-liquid interface and using T3 and activin receptor-like kinase ("ALK") 5 inhibitors.

A variety of transcription factors regulate the differentiation of pancreatic endocrine cells into insulin secreting β cells. Among these factors is v-maf avian musculoaponeurotic fibrosarcoma oncogene homolog A ("MAFA"). In fact, it is believed that MAFA may be a master regulator in β cells of glucose stimulated insulin secretion.

In general, the process of differentiating progenitor cells to functional β cells goes through various stages and great strides have been made in improving protocols to generate pancreatic cells from progenitor cells, such as human pluripotent stem cells. Despite these advances in research, each step in the process of differentiating progenitor cells presents a unique challenge. As such, there is still a need for a further differentiation protocol development for the purpose of producing functional endocrine cells and, in particular, functional β cells. In particular, it is desirable to develop processes in which the expression of MAFA in pancreatic endocrine cells is enhanced.

BRIEF DESCRIPTION OF THE DRAWINGS

FIGS. 1A, 1B, 1C, 1D, 1E, 1F, 1G, 1H, 1I, 1J, 1K, 1L and 1M are graphs depicting data from real-time PCR analyses of the fold change of gene expression over undifferentiated ES cells of PDX1, NKX6.1, PAX4, PAX6, NGN3, MAFA, ABCC8, chromogranin-A, G6PC2, 1APP, insulin, glucagon and PTF1a from the stem cell line H1 differentiated in accordance with Example 1.

FIGS. 4A, 4B, 4C, 4D and 4E depict FACS profiles of Stage 5 cells, differentiated according to Example 1, and stained for: chromogranin (X-axis) co-stained with NKX6.1 (Y-axis) in FIG. 4A; PDX1 (X-axis) co-stained with Ki67 (Y-axis) in FIG. 4B; and NKX6.1 (X-axis) co-stained with insulin (Y-axis) in FIG. 4C; NeuroD1 in FIG. 4D; and insulin (X-axis) co-stained with glucagon (Y-axis).

FIGS. 5A, 5B, 5C, 5D, 5E and 5F depict FACS profiles of Stage 6 cells, differentiated according to Example 1, and stained for: chromogranin (X-axis) co-stained with NKX6.1 (Y-axis) in FIG. 5A; PDX1 (X-axis) co-stained with Ki67 (Y-axis) in FIG. 5B; and NKX6.1 (X-axis) co-stained with insulin (Y-axis) in FIG. 5C; PAX6 (X-axis) co-stained with Oct 3/4 (Y-axis) in FIG. 5D; insulin (X-axis) co-stained with glucagon (Y-axis) in FIG. 5E; and FOXA2 in FIG. 5F.

FIGS. 6A, 6B, 6C, 6D, 6E and 6F depict FACS profiles of Stage 7 cells, differentiated according to Example 1, and stained for: chromogranin (X-axis) co-stained with NKX6.1 (Y-axis) in FIG. 6A; PDX1 (X-axis) co-stained with Ki67 (Y-axis) in FIG. 6B; and NKX6.1 (X-axis) co-stained with insulin (Y-axis) in FIG. 6C; PAX6 (X-axis) co-stained with Oct 3/4 (Y-axis) in FIG. 6D; insulin (X-axis) co-stained with glucagon (Y-axis) in FIG. 6E; and FOXA2 in FIG. 6F.

FIG. 9 is graph depicting data from real-time PCR analyses of the fold change of expression of AXL and GAS6 of differentiated cells of Example 4 over undifferentiated cells.

FIGS. 10A through 10F are graphs of data from real-time PCR analyses of the fold change of expression of MAFA, UCN3, G6PC2, NKX6.1, PDX1 and insulin of differentiated cells over undifferentiated cells after treatment with small molecules in Stage 7 in accordance with Example 6.

FIGS. 11A through 11D are graphs depicting data from real-time PCR analyses of the fold change of expression of MAFA, PDX1, NKX6.1, and insulin of differentiated cells over undifferentiated cells after treatment with small molecules in Stage 7 in accordance with Example 7.

DETAILED DESCRIPTION OF THE INVENTION

Figure 2C:
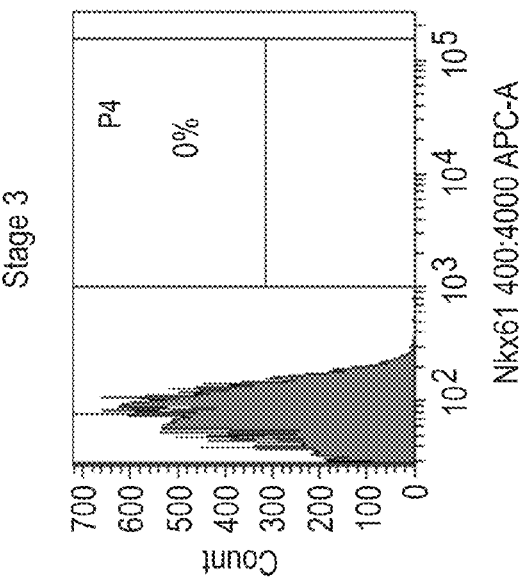
FIGS. 2A, 2B and 2C depict FACS profiles of Stage 3 cells, differentiated according to Example 1, and stained for: PDX1 (X-axis) co-stained with Ki67 (Y-axis) in FIG. 2A; PDX1 (X-axis) co-stained with CDX2 (Y-axis) in FIG. 2B; and NKX6.1 in FIG. 2C.
Figure 2B:
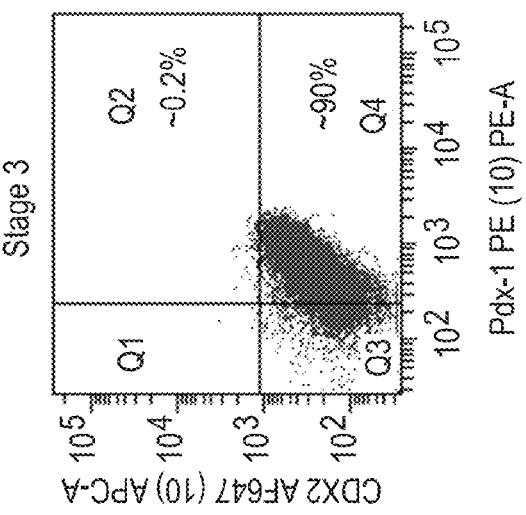
Figure 2A:
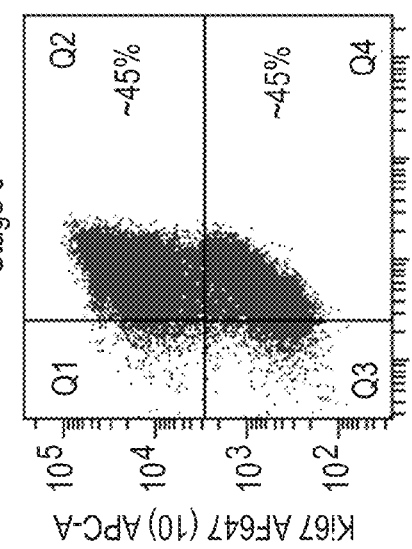
Figure 3A:
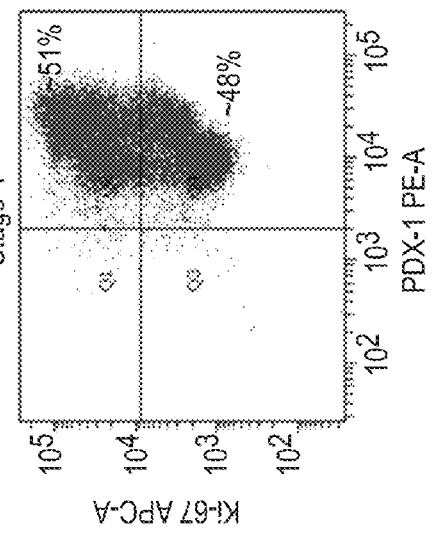
FIGS. 3A, 3B, 3C and 3D depict FACS profiles of Stage 4 cells, differentiated according to Example 1, and stained for: chromogranin (X-axis) co-stained with NKX6.1 (Y-axis) in FIG. 3A; PDX1 (X-axis) co-stained with Ki67 (Y-axis) in FIG. 3B; NKX6.1 (X-axis) co-stained with insulin (Y-axis) in FIG. 3C; and NeuroD1 in FIG. 3D.
Figure 3B:
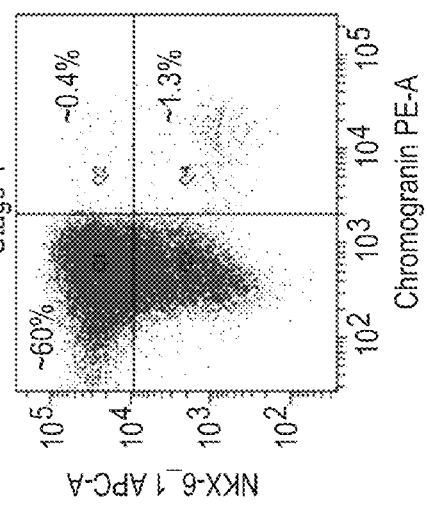
Figure 3C:
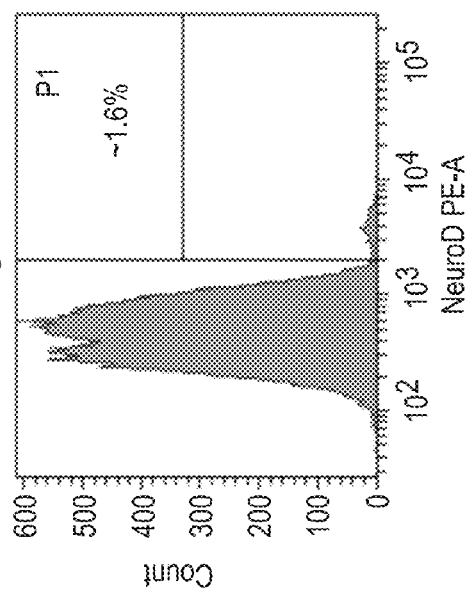
Figure 3D:
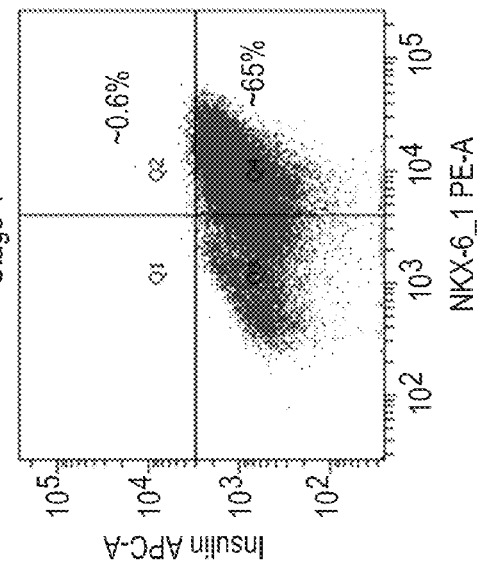

The following detailed description of the invention will be better understood when read in conjunction with the appended figures. For the purpose of illustrating the invention, the figures demonstrate embodiments of the present invention. However, the invention is not limited to the precise arrangements, examples, and instrumentalities shown. For clarity of disclosure, and not by way of limitation, the detailed description of the invention is divided into subsections that describe or illustrate certain features, embodiments, or applications of the present invention.

The present invention is directed to generating pancreatic endocrine cells of a more mature phenotype by treatment of less mature pancreatic endocrine cells with certain small molecules. In certain embodiments of the invention, pancreatic endocrine cells are cultured, in one or more stages, in the presence of small molecules that are one or more of a protein methyltransferase inhibitor, an aurora kinase inhibitor, and a p90 ribosomal S6 kinase ("RSK") inhibitor. Thus, the present invention provides cell cultures for differentiating pluripotent stem cells to cells exhibiting characteristics of pancreatic endocrine cells of a mature phenotype, as well as differentiation media that initiates and facilitates such differentiation, and differentiated cells and cell populations resulting from the differentiation. The methods of the invention provide for the formation of a pancreatic endocrine cell population wherein at least 10%, preferably at least 20%, more preferably at least 30% and most preferably at least 50%, of the cells express single hormonal insulin and are PDX1, NKX6.1 and MAFA positive.

Advantageously and preferably, the cell cultures and differentiation media of the invention may be used in conjunction with differentiation at the air-liquid interface. The culturing may occur at the air-liquid interface for all stages involved in the differentiation pathway from pluripotent stem cells to pancreatic endocrine cells of a mature phenotype or it may involve culturing on a planar culture submersed in medium for the early stages of differentiation followed by culturing at the air-liquid interface during one or more of the later stages of differentiation. More preferably, the processes of the invention involves the combination of culturing pluripotent stem cells on a support surface submerged in medium through the early stages, and then culturing at the air-liquid interface for the later stages of differentiation. In such embodiments, the cells may initially be seeded on a solid surface for submerged culturing and then removed from the solid support and re-seeded on a porous support for culturing at the air-liquid interface. Alternatively, the cells may be seeded initially on a porous support that is then submerged in media for the early stages of differentiation and subsequently positioned at the air-liquid interface for the later stages of differentiation.

In yet another embodiment, differentiation at one or more stages also is carried out in the presence of one or more of T3, T4, analogues thereof and, optionally but preferably, with an activin receptor-like kinase 5 ("ALK 5") inhibitor. In a preferred embodiment, a population of pancreatic endoderm/endocrine precursor cells are cultured in media containing one or more of T3, T4, analogues thereof and an ALK 5 inhibitor to pancreatic endocrine cells. In a more preferred embodiment, the resulting pancreatic endocrine cells are further differentiated in the presence of media containing one or more of T3. T4, analogues thereof and an ALK 5 inhibitor.

It is a particular discovery of the invention that treatment of pancreatic endoderm cells with a combination of one or more of an ALK 5 inhibitor and a thyroid receptor agonist followed by culturing of the resulting pancreatic endocrine cells in combination with one or more of an inhibitor of protein methyltransferase DOT1L, an aurora kinase inhibitor, and an RSK inhibitor significantly enhances the number of cells in a population expressing, single hormonal insulin, MAFA, PDX1, and NKX6.1 as well as increases the level of MAFA expression in the cells. The invention finds particular utility when used in conjunction with differentiation at the air-liquid interface.

Definitions

Stem cells are undifferentiated cells defined by their ability, at the single cell level, to both self-renew and differentiate. Stem cells may produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm, and ectoderm). Stem cells also give rise to tissues of multiple germ layers following transplantation and contribute substantially to most, if not all, tissues following injection into blastocysts.

Stem cells are classified by their developmental potential. Pluripotent stem cells are able to give rise to all embryonic cell types.

Differentiation is the process by which an unspecialized ("uncommitted") or less specialized cell acquires the features of a specialized cell, for example a nerve cell or a muscle cell. A differentiated cell is one that has taken on a more specialized ("committed") position within the lineage of a cell. The term "committed", when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. "De-differentiation" refers to the process by which a cell reverts to a less specialized (or committed) position within the lineage of a cell. As used herein, the lineage of a cell defines the heredity of the cell, i.e., which cells it came from and to what cells it can give rise. The lineage of a cell places the cell within a hereditary scheme of development and differentiation. A lineage-specific marker refers to a characteristic specifically associated with the phenotype of cells of a lineage of interest and can be used to assess the differentiation of an uncommitted cell to the lineage of interest.

"Markers", as used herein, are nucleic acid or polypeptide molecules that are differentially expressed in a cell of interest. In this context, differential expression means an increased level for a positive marker and a decreased level for a negative marker as compared to an undifferentiated cell or a cell at another stage of differentiation. The detectable level of the marker nucleic acid or polypeptide is sufficiently higher or lower in the cells of interest compared to other cells, such that the cell of interest can be identified and distinguished from other cells using any of a variety of methods known in the art.

As used herein, a cell is "positive for" a specific marker, "positive", or "+" when the specific marker is sufficiently detected in the cell. Similarly, the cell is "negative for", "negative" or "−" for a specific marker when the specific marker is not sufficiently detected in the cell. In particular, positive by fluorescence activated cell sorting cytometry ("FACS") is usually greater than about 2%, whereas the negative threshold by FACS is usually less than about 1%. Positive by polymerase chain reaction cytometry ("PCR") is usually less than or equal to about 30 cycles (Cts); whereas negative by PCR is usually more than about 31 cycles.

In attempts to replicate the differentiation of pluripotent stem cells into functional pancreatic endocrine cells in static in vitro cell cultures, the differentiation process is often viewed as progressing through a number of consecutive stages. In particular, the differentiation process is commonly viewed as progressing through multiple stages. In this stepwise differentiation, "Stage 1" refers to the first step in the differentiation process, the differentiation of pluripotent stem cells into cells expressing markers characteristic of the definitive endoderm ("Stage 1 cells"). "Stage 2" refers to the second step, the differentiation of cells expressing markers characteristic of the definitive endoderm cells into cells expressing markers characteristic of gut tube cells ("Stage 2 cells"). "Stage 3" refers to the third step, differentiation of cells expressing markers characteristic of gut tube cells into cells expressing markers characteristic of foregut endoderm cells ("Stage 3 cells"). "Stage 4" refers to the fourth step, the differentiation of cells expressing markers characteristic of foregut endoderm cells into cells expressing markers characteristic of pancreatic foregut precursor cells ("Stage 4 cells"). "Stage 5" refers to the fifth step, the differentiation of cells expressing markers characteristic of pancreatic foregut precursor cells into cells expressing markers characteristic of one or both of pancreatic endoderm cells and pancreatic endocrine precursor cells (collectively referred to as "Stage 5 cells" or, alternatively, "pancreatic endoderm/ endocrine precursor cells"). Stage 6 refers to the sixth step, the differentiation of cells expressing markers characteristic of pancreatic endoderm/endocrine precursor cells into cells expressing markers characteristic of pancreatic endocrine cells that are immature beta cell ("Stage 6 cells"). Stage 6 cells express single hormonal insulin and are PDX1, NKX6.1 and chromogranin positive. In the process of, and for purposes of producing the populations of and cells of the invention, a seventh step, "Stage 7", is used and refers to differentiation of cells expressing markers characteristic of pancreatic endocrine cells that are immature beta cells into cells expressing markers characteristic of pancreatic endocrine cells that are maturing beta cells and that have a more mature phenotype as compared to Stage 6 cells. By or "Stage 7 cells" is meant a pancreatic endocrine cell that is single hormonal insulin +, MAFA+, NKX6.1+, and PDX1+ but also expresses MAFA at a higher level than an immature beta cell. Additionally, the cell population resulting from carrying out Stage 7 has a higher percentage of MAFA positive and single hormonal insulin expressing cells as compared to populations of cells of Stage 6.

It is to be noted that not all cells in a particular population progress through these stages at the same rate. Consequently, it is not uncommon in in vitro cell cultures to detect the presence of cells that have progressed less, or more, down the differentiation pathways than the majority of cells present in the population, particularly at the later differentiation stages. For example, it is not uncommon to see the appearance of markers characteristic of pancreatic endocrine cells during the culture of cells at Stage 5. For purposes of illustrating the present invention, characteristics of the various cell types associated with the above-identified stages are described herein.

"Definitive endoderm" as used herein, refers to cells which bear the characteristics of cells arising from the epiblast during gastrulation and which form the gastrointestinal tract and its derivatives. Definitive endoderm cells express at least one of the following markers: FOXA2 (also known as hepatocyte nuclear factor 3-β ("HNF3-β")), GATA4, SOX17, CXCR4, Brachyury, Cerberus, OTX2, goosecoid, C-Kit, CD99, and MIXL1. Markers characteristic of the definitive endoderm cells are CXCR4, FOXA2, and SOX17. Thus, definitive endoderm cells may be characterized by their expression of CXCR4, FOXA2, and SOX17. In addition, depending on the length of time cells are allowed to remain in Stage 1, an increase in HNF4α may be observed.

"Gut tube cells", as used herein, refers to cells derived from definitive endoderm and that can give rise to all endodermal organs, such as lungs, liver, pancreas, stomach, and intestine. Gut tube cells may be characterized by their substantially increased expression of HNF4α over that expressed by definitive endoderm cells. For example, a ten- to forty-fold increase in mRNA expression of HNF4α may be observed during Stage 2.

"Foregut endoderm cells", as used herein, refers to cells that give rise to the esophagus, lungs, stomach, liver, pancreas, gall bladder, and a portion of the duodenum. Foregut endoderm cells express at least one of the following markers: PDX1, FOXA2, CDX2, SOX2, and HNF4α. Foregut endoderm cells may be characterized by an increase in expression of PDX1 compared to gut tube cells. For example, greater than fifty percent of the cells in Stage 3 cultures typically express PDX1.

"Pancreatic foregut precursor cells", as used herein, refers to cells that express at least one of the following markers: PDX1, NKX6.1, HNF6, NGN3, SOX9, PAX4, PAX6, ISL1, gastrin, FOXA2, PTF1a, PROX1 and HNF4α. Pancreatic foregut precursor cells may be characterized by being positive for the expression of at least one of PDX1, NKX6.1, and SOX9.

"Pancreatic endoderm cells", as used herein, refers to cells that express at least one of the following markers: PDX1, NKX6.1, HNF1β, PTF1α, HNF6, HNF4α, SOX9. NGN3, gastrin; HB9, or PROX1. Pancreatic endoderm cells may be characterized by their lack of substantial expression of CDX2 or SOX2.

"Pancreatic endocrine precursor cells", as used herein, refers to pancreatic endoderm cells capable of becoming a pancreatic hormone expressing cell. Pancreatic endocrine precursor cells express at least one of the following markers: NGN3; NKX2.2; NeuroD11; ISL1; PAX4; PAX6; or ARX. Pancreatic endocrine precursor cells may be characterized by their expression of NKX2.2 and NeuroD11.

"Pancreatic endocrine cells", as used herein, refer to cells capable of expressing at least one of the following hormones: insulin, glucagon, somatostatin, ghrelin, and pancreatic polypeptide. In addition to these hormones, markers characteristic of pancreatic endocrine cells include one or more of NeuroD1, ISL1, PDX1, NKX6.1, ARX, NKX2.2, HB9 and PAX6. One subset of pancreatic endocrine cells is "immature beta cells" that are cells capable of expressing insulin, but not glucagon, somatostatin, ghrelin, and pancreatic polypeptide. In addition, markers characteristic of immature beta cells include one or more of NeuroD1, ISL1, PDX1, NKX6.1, NKX2.2, HB9 and PAX6. A second subset of pancreatic endocrine cells is "maturing beta cells" that are cells capable of expressing insulin, but not glucagon, somatostatin, ghrelin, and pancreatic polypeptide. Additionally, markers characteristic of maturing beta cells include one or more of NeuroD1, ISL1, PDX1, NKX6.1, NKX2.2, HB9, PAX6 and MAFA. Yet another subset of pancreatic endocrine cells are those expressing markers characteristic of mature beta cells and that can be characterized by their expression of PDX1, NKX2.2, NKX6.1, NeuroD1, ISL1, HNF3β, HB9, MAFA and PAX6 along with an insulin release in response to a glucose challenge that is robust and increased in comparison to that of less mature beta cells.

"Air-liquid interface" or "ALI", as used herein, refers to the air-liquid interface that exists in an open culture vessel or a culture vessel partially filled with medium. Although referred to herein as "air" for convenience, the invention is not limited to the mixture of gases and compositions found in the ambient environment. The invention specifically contemplates and includes gaseous mixtures having compositions different from the ambient environment including, for example, mixtures enriched for a particular component or in which a particular component has been depleted or eliminated.

Used interchangeably herein are "d1", "1d", and "day 1"; "d2", "2d", and "day 2", and so on. These number letter combinations refer to a specific day of incubation in the different stages during the stepwise differentiation protocol of the instant application.

"LDN-193189" refers to ((6-(4-(2-(piperidin-1-yl) ethoxy)phenyl)-3-(pyridin-4-yl)pyrazolo[1,5-a]pyrimidine, hydrochloride)) a BMP receptor inhibitor available from Shanghai ChemPartner, Co., LTD.

Characterization, Source, Expansion and Culture of Pluripotent Stem Cells

A. Characterization of Pluripotent Stem Cells

Pluripotent stem cells may express one or more of the designated TRA-1-60 and TRA-1-81 antibodies (Thomson et al. 1998, *Science* 282:1145-1147). Differentiation of pluripotent stem cells in vitro results in the loss of TRA-1-60 and TRA-1-81 expression. Undifferentiated pluripotent stem cells typically have alkaline phosphatase activity, which can be detected by fixing the cells with 4% paraformaldehyde, and then developing with an alkaline phosphatase substrate kit sold under the trademark VECTOR® Red, as described by the manufacturer (Vector Laboratories, Inc., Burlingame, Calif.). Undifferentiated pluripotent stem cells also typically express OCT4 and TERT, as detected by reverse transcription polymerase chain reaction ("RT-PCR").

Another desirable phenotype of propagated pluripotent stem cells is a potential to differentiate into cells of all three germinal layers: endoderm, mesoderm, and ectoderm. Pluripotency of stem cells may be confirmed, for example, by injecting cells into severe combined immunodeficiency ("SCID") mice, fixing the teratomas that form using 4% paraformaldehyde, and then examining histologically for evidence of cell types from these three germ layers. Alternatively, pluripotency may be determined by the creation of embryoid bodies and assessing the embryoid bodies for the presence of markers associated with the three germinal layers.

Propagated pluripotent stem cell lines may be karyotyped using a standard G-banding technique and compared to published karyotypes of the corresponding primate species. It is desirable to obtain cells that have a "normal karyotype," which means that the cells are euploid, wherein all human chromosomes are present and not noticeably altered.

B. Sources of Pluripotent Stem Cells

Any pluripotent stem cells may be used in the methods of the invention. Exemplary types of pluripotent stem cells that may be used include established lines of pluripotent cells, including pre-embryonic tissue (such as, a blastocyst), embryonic tissue, or fetal tissue taken any time during gestation, typically but not necessarily, before approximately 10 to 12 weeks gestation. Non-limiting examples are established lines of human embryonic stem cells ("hESCs") or human embryonic germ cells, such as, the human embryonic stem cell lines H1 (NIH Code: WA01), H7 (NIH Code: WA07), H9 (NIH Code: WA09) (WiCell Research Institute, Madison, Wis., USA), and SA002 (Cellartis AB Corporation, Goteburg, Sweden).

Cells taken from a pluripotent stem cell population already cultured in the absence of feeder cells are also suitable. Induced pluripotent cells (IPS), or reprogrammed pluripotent cells, derived from adult somatic cells using forced expression of a number of pluripotent related transcription factors, such as OCT4, NANOG, SOX2, KLF4, and ZFP42 (*Annu Rev Genomics Hum Genet* 2011, 12:165-185; see also IPS, *Cell,* 126(4): 663-676) may also be used. The human embryonic stem cells used in the methods of the invention may also be prepared as described by Thomson et al. (U.S. Pat. No. 5,843,780; *Science,* 1998, 282:1145-1147; *Curr Top Dev Biol* 1998, 38:133-165; *Proc Natl Acad Sci U.S.A.* 1995, 92:7844-7848). Mutant human embryonic stem cell lines, such as, BG01v (BresaGen, Athens, Ga.), or cells derived from adult human somatic cells, such as, cells disclosed in Takahashi et al., *Cell* 131: 1-12 (2007) may also be used. In certain embodiments, pluripotent stem cells suitable for use in the present invention may be derived according to the methods described in: Li et al. (*Cell Stem Cell* 4: 16-19, 2009); Maherali et al. (*Cell Stem Cell* 1: 55-70, 2007); Stadtfeld et al. (*Cell Stem Cell* 2: 230-240); Nakagawa et al. (*Nature Biotechnol* 26: 101-106, 2008); Takahashi et al. (*Cell* 131: 861-872, 2007); and U.S. Patent App. Pub. No. 2011/0104805. In certain embodiments, pluripotent stem cells suitable for use in the present invention may be considered "naïve" and derived according to the methods described in: Gafni et al. (*Nature,* 504:282, 2013), and Ware et al. (PNAS, 111: 4484-4489, 2014). All of these references, patents, and patent applications are herein incorporated by reference in their entirety, in particular, as they pertain to the isolation, culture, expansion and differentiation of pluripotent cells.

Other sources of pluripotent stem cells include induced pluripotent stem cells (IPS, Cell, 126(4): 663-676). Yet other sources of suitable cells include human umbilical cord tissue-derived cells, human amniotic fluid-derived cells, human placental-derived cells, and human parthenotes. In one embodiment, the umbilical cord tissue-derived cells may be obtained by the method of U.S. Pat. No. 7,510,873. In another embodiment, the placental tissue-derived cells may be obtained using the methods of U.S. Patent Application Publication No. 2005/0058631. In another embodiment, the amniotic fluid-derived cells may be obtained using the methods of U.S. Patent App. Pub. No. 2007/0122903. The disclosure of each of these patent applications is incorporated in its entirety herein as it pertains to the isolation and characterization of the cells. In certain embodiments, the pluripotent stem cells may be of non-embryonic origins.

C. Expansion and Culture of Pluripotent Stem Cells

Pluripotent stem cells are typically cultured on a layer of feeder cells that support the pluripotent stem cells in various ways. Alternatively, pluripotent stem cells may be cultured in a culture system that is essentially free of feeder cells, but nonetheless supports proliferation of pluripotent stem cells without undergoing substantial differentiation. The growth of pluripotent stem cells in feeder-free culture without differentiation is often supported using a medium conditioned by culturing previously with another cell type. Alternatively, the growth of pluripotent stem cells in feeder-free culture without differentiation can be supported using a chemically defined medium.

Pluripotent cells may be readily expanded in culture using various feeder layers or by using matrix protein coated vessels. Alternatively, chemically defined surfaces in combination with defined media, such as media sold under the trademark mTESR®1 (StemCell Technologies, Inc., Vancouver, B.C., Canada), may be used for routine expansion of the cells. Pluripotent cells may be readily removed from culture plates using enzymatic digestion, mechanical separation, or various calcium chelators such as ethylenediaminetetraacetic acid ("EDTA"). Alternatively, pluripotent cells may be expanded in suspension in the absence of any matrix proteins or feeder layer.

Many different known methods of expanding and culturing pluripotent stem cells may be used in the claimed invention. For example, the methods of the invention may use the methods of Reubinoff et al., Thompson et al., Richards et al. and U.S. Patent App. Pub. No. 2002/0072117. Reubinoff et al. (*Nature Biotechnology* 18: 399-404 (2000)) and Thompson et al. (*Science* 282: 1145-1147 (1998)) disclose the culture of pluripotent stem cell lines from human blastocysts using a mouse embryonic fibroblast feeder cell layer. Richards et al. (*Stem Cells* 21: 546-556, 2003) evaluated a panel of eleven different human adult, fetal, and neonatal feeder cell layers for their ability to support human pluripotent stem cell culture, noting that "human embryonic stem cell lines cultured on adult skin fibroblast feeders retain human embryonic stem cell morphology and remain pluripotent." U.S. Patent App. Pub. No. 2002/0072117 discloses cell lines that produce media that support the growth of primate pluripotent stem cells in feeder-free culture. The cell lines employed are mesenchymal and fibroblast-like cell lines obtained from embryonic tissue or differentiated from embryonic stem cells. U.S. Patent App. Pub. No. 2002/072117 also discloses the use of the cell lines as a primary feeder cell layer.

Other suitable known methods of expanding and culturing pluripotent stem cells are disclosed, for example, in Wang et al., Stojkovic et al., Miyamoo et al. and Amit et al. Wang et al. (*Stem Cells* 23: 1221-1227, 2005) disclose methods for the long-term growth of human pluripotent stem cells on feeder cell layers derived from human embryonic stem cells. Stojkovic et al. (*Stem Cells* 2005 23: 306-314, 2005) disclose a feeder cell system derived from the spontaneous differentiation of human embryonic stem cells. Miyamoto et al. (*Stem Cells* 22: 433-440, 2004) disclose a source of feeder cells obtained from human placenta. Amit et al. (*Biol. Reprod* 68: 2150-2156, 2003) disclose a feeder cell layer derived from human foreskin.

Other suitable methods of expanding and culturing pluripotent stem cells are disclosed, for example, in Inzunza et al., U.S. Pat. No. 6,642,048, WO 2005/014799, Xu et al. and U.S. Patent App. Pub. No. 2007/0010011. Inzunza et al. (*Stem Cells* 23: 544-549, 2005) disclose a feeder cell layer from human postnatal foreskin fibroblasts. U.S. Pat. No. 6,642,048 discloses media that support the growth of primate pluripotent stem cells in feeder-free culture, and cell lines useful for production of such media. U.S. Pat. No. 6,642,048 reports mesenchymal and fibroblast-like cell lines obtained from embryonic tissue or differentiated from embryonic stem cells, as well as methods for deriving such cell lines, processing media, and growing stem cells using such media. WO 2005/014799 discloses a conditioned medium for the maintenance, proliferation, and differentiation of mammalian cells. WO 2005/014799 reports that the culture medium produced via the disclosure is conditioned by the cell secretion activity of murine cells; in particular, those differentiated and immortalized transgenic hepatocytes, named MMH (Met Murine Hepatocyte). Xu et al. (*Stem Cells* 22: 972-980, 2004) discloses a conditioned medium obtained from human embryonic stem cell derivatives that have been genetically modified to over express human telomerase reverse transcriptase. U.S. Patent App. Pub. No. 2007/0010011 discloses a chemically defined culture medium for the maintenance of pluripotent stem cells.

A known alternative culture system employs serum-free medium supplemented with growth factors capable of promoting the proliferation of embryonic stem cells. Examples of such culture systems include, but are not limited, to Cheon et al., Levenstein et al. and U.S. Patent App. Pub. No. 2005/0148070. Cheon et al. (BioReprod DOI:10.1095/biolreprod. 105.046870, Oct. 19, 2005) disclose a feeder-free, serum-free culture system in which embryonic stem cells are maintained in unconditioned serum replacement medium supplemented with different growth factors capable of triggering embryonic stem cell self-renewal. Levenstein et al. (*Stem Cells* 24: 568-574, 2006) disclose methods for the long-term culture of human embryonic stem cells in the absence of fibroblasts or conditioned medium, using media supplemented with bFGF. U.S. Patent App. Pub. No. 2005/0148070 discloses a method of culturing human embryonic stem cells in defined media without serum and without fibroblast feeder cells, the method comprising: culturing the stem cells in a culture medium containing albumin, amino acids, vitamins, minerals, at least one transferrin or transferrin substitute, at least one insulin or insulin substitute, the culture medium essentially free of mammalian fetal serum and containing at least about 100 ng/ml of a fibroblast growth factor capable of activating a fibroblast growth factor signaling receptor, wherein the growth factor is supplied from a source other than just a fibroblast feeder layer, the medium supported the proliferation of stem cells in an undifferentiated state without feeder cells or conditioned medium.

Still other known suitable methods of culturing and expanding pluripotent stem cells are disclosed in U.S. Patent App. Pub. No. 2005/0233446, U.S. Pat. No. 6,800,480, U.S. Patent App. Pub. No. 2005/0244962 and WO 2005/065354. U.S. Patent App. Pub. No. 2005/0233446 discloses a defined media useful in culturing stem cells, including undifferentiated primate primordial stem cells. In solution, the media is substantially isotonic as compared to the stem cells being cultured. In a given culture, the particular medium is a base medium and an amount of each of bFGF, insulin, and ascorbic acid necessary to support substantially undifferentiated growth of the primordial stem cells. U.S. Pat. No. 6,800,480 reports that a cell culture medium for growing primate-derived primordial stem cells in a substantially undifferentiated state is provided which includes a low osmotic pressure, low endotoxin basic medium that is effective to support the growth of primate-derived primordial stem cells. The disclosure of the U.S. Pat. No. 6,800,480 patent further reports that the basic medium is combined with a nutrient serum effective to support the growth of primate-derived primordial stem cells and a substrate selected from feeder cells and an extracellular matrix component derived from feeder cells. This medium is further noted to include non-essential amino acids, an anti-oxidant, and a first growth factor selected from nucleosides and a pyruvate salt. U.S. Patent App. Pub. No. 2005/0244962 reports that one aspect of the disclosure provides a method of culturing primate embryonic stem cells and that the stem cells in culture are essentially free of mammalian fetal serum (preferably also essentially free of any animal serum) and in the presence of fibroblast growth factor that is supplied from a source other than just a fibroblast feeder layer.

WO 2005/065354 discloses a defined, an isotonic culture medium that is essentially feeder-free and serum-free, that is a basal medium, bFGF, insulin and ascorbic acid in amounts sufficient to support growth of substantially undifferentiated mammalian stem cells. Furthermore, WO 2005/086845 discloses a method for maintenance of an undifferentiated stem cell, said method comprising exposing a stem cell to a member of the transforming growth factor-beta ("TGF-β") family of proteins, a member of the fibroblast growth factor ("FGF") family of proteins, or nicotinamide in an amount sufficient to maintain the cell in an undifferentiated state for a sufficient amount of time to achieve a desired result.

The pluripotent stem cells may be plated onto a suitable culture substrate. In one embodiment, the suitable culture substrate is an extracellular matrix component, such as those derived from basement membrane or that may form part of adhesion molecule receptor-ligand couplings. A suitable culture substrate is a reconstituted basement membrane sold under the trademark MATRIGEL™ (Corning Incorporated, Corning, N.Y.). MATRIGEL™ is a soluble preparation from Engelbreth-Holm Swarm tumor cells that gels at room temperature to form a reconstituted basement membrane.

Other extracellular matrix components and component mixtures known in the art are suitable as an alternative. Depending on the cell type being proliferated, this may include laminin, fibronectin, proteoglycan, entactin, heparin sulfate, and the like, alone or in various combinations.

The pluripotent stem cells may be plated onto the substrate in a suitable distribution and in the presence of a medium, that promotes cell survival, propagation, and retention of the desirable characteristics. All these characteristics benefit from careful attention to the seeding distribution and can readily be determined by one of skill in the art. Suitable culture media may be made from the following components, Dulbecco's Modified Eagle's medium ("DMEM") sold under the trademark GIBCO® (Catalog No. 11965-092) by Life Technologies Corporation, Grand Island N.Y.; Knockout Dulbecco's Modified Eagle's medium ("KO DMEM") sold under the trademark GIBCO® (Catalog No. 10829-018) by Life Technologies Corporation; Ham's F12/50% DMEM basal medium; 200 mM L-glutamine sold under the trademark GIBCO® (Catalog No. 25030-081) by Life Technologies; non-essential amino acid solution sold under the trademark GIBCO® (Catalog No. 11140-050) by Life Technologies; β-mercaptoethanol, Sigma-Aldrich Company, LLC Saint Louis, Mo., (Catalog No. M7522); human recombinant basic fibroblast growth factor ("bFGF") sold under the trademark GIBCO® (Catalog No. 13256-029) by Life Technologies.

Large-scale expansion and controlled differentiation processes of human embryonic stem cells can also be achieved using suspension bioreactors. Such systems may be able to generate clinically relevant cell numbers with greater efficacy in a controlled culture system. It is known to use established bioreactor culture systems that allow for the expansion of pluripotent murine and hES cells for example as disclosed in *Journal of Biotechnology*, May 2014, Vol. 178: 54-64, *Stem Cell Reports*, April 2014, Vol. 3, No. 6:1132, and *Tissue Engineering Part C: Methods*, February 2013, Vol. 19, No. 2: 166-180.

Differentiation of Pluripotent Stem Cells

As pluripotent cells differentiate towards β cells, they differentiate through various stages each of which may be characterized by the presence or absence of particular markers. Differentiation of the cells into these stages is achieved by the specific culturing conditions including the presence and lack of certain factors added to the culture media. In general, this differentiation may involve differentiation of pluripotent stem cells into definitive endoderm lineage, and definitive endoderm, cells. These cells may then be further differentiated into gut tube cells, which in turn may then be differentiated into foregut endoderm cells. Foregut endoderm cells may be differentiated into pancreatic foregut precursor cells which may then be further differentiated into pancreatic endoderm cells, pancreatic endocrine precursor cells or both. These cells may be differentiated into pancreatic hormone producing or secreting cells. This application provides for the staged differentiation of pluripotent stem cells towards the pancreatic endocrine cells, preferably by culturing the cells at the air-liquid interface that exists within a culture vessel partially filled with medium, specifically by culturing cells at the air-liquid interface in one or more of Stages 5 through 7.

One or more of the thyroid hormones triiodothyronine ("T3") and thyroxine ("T4"), and analogues thereof, alone or in further combination with an ALK 5 inhibitor may be used in the cell culturing at one or more of Stages 1 through 7 of differentiation, and preferably at each of Stages 5 through 7. Alternatively, the ALK 5 inhibitor may be used alone in one or more stages of differentiation, but preferably at each of Stages 5 through 7. More preferably, one or more of the thyroid hormones or their analogues and an ALK 5 inhibitor is used in one or more differentiation stages and preferably at each of Stages 5 through 7. Suitable thyroid hormone analogues may include, without limitation: GC-1 (Sobertirome) (available from R&D Systems, Inc. Minneapolis, Minn.); 3,5-diiodothryopropionic acid ("DIPTA"); KB-141 discussed in *J. Steroid Biochem. Mol. Biol.*, 2008, 111: 262-267 and *Proc. Natl. Acad. Sci.* US 2003, 100: 10067-10072; MB07344 discussed in *Proc. Natl. Acad. Sci.* US 2007, 104: 15490-15495; T0681 discussed in *J. Lipid Res.*, May 2009, 50:938 and *Endocr. Pract.* 2012, 18(6): 954-964, the disclosures of which are incorporated herein by reference in their entireties. Useful ALK5 inhibitors include: ALK5 inhibitor II (Enzo Life Sciences, Inc., Farmingdale, N.Y.), which is also the preferred ALK5 inhibitor; ALK5i (Axxora, Inc., San Diego, Calif.), SD208 (R&D Systems); TGF-β inhibitor SB431542 (Xcess Biosciences. Inc., San Diego, Calif.); ITD-1 (Xcess Biosciences); LY2109761 (Xcess Biosciences); A83-01 (Xcess Biosciences); LY2157299 (Xcess Biosciences); TGF-β receptor inh V (EMD Millipore Chemical, Gibstown, N.J.); TGF-β receptor inh I (EMD Millipore); TGF-β receptor inh IV (EMD Millipore); TGF-β receptor inh VII (EMD Millipore); TGF-β receptor inh VIII (EMD Millipore); TGF-β receptor inh II (EMD Millipore); TGF-β receptor inh VI (EMD Millipore); and TGF-β receptor inh VI (EMD Millipore).

In addition, in preferred embodiments of the invention, the methods include treating cells at one or more stages, but preferably treating cells during Stage 7, with a differentiation medium that includes one or both of an antioxidant, such as vitamin E, acetyl cysteine, vitamin C, Antioxidant Supplement (Catalog No. A1345, Sigma-Aldrich Company, LLC Saint Louis, Mo.), glutathione, superoxide dismutase, catalase and the like and combinations thereof. In still more preferred embodiments, in carrying out Stage 6, a gamma secretase inhibitor is used, which can be gamma secretase inhibitor XX (EMD Millipore), gamma secretase inhibitor XXI (EMD Millipore), gamma secretase inhibitor XVI (EMD Millipore), N-[(3,5-difluorophenyl)acetyl]-L-alanyl-2-phenyl]glycine-1,1-dimethylethyl ester ("DAPT") (Catalog. Ni. 2634, Tocris Bioscience, Bristol, United Kingdom), and the like and combinations thereof. Useful amounts of gamma secretase inhibitor may be about 50 nM to 5000 nM, preferably about 50 nM to 500 nM. The amount of antioxidant may be about 0.1 to 100 μM, alternatively about 0.1 to 20 μM, and preferably about 1 to 10 μM. Alternatively, useful amounts of antioxidant may be about 100 nM to 5 mM, about 1000 nM to 2 mM, and preferably about 0.1 to 1 mM.

In most preferred embodiments of the invention, certain small molecules are used in the medium of one or more stages of differentiation, preferably at one or both of Stages 6 and 7. The small molecules of interest are those capable of inhibiting aurora kinase, p90 ribosomal S6 kinase, or methyl transferase DOT1L and preferably are used along with antioxidants that reduce oxidative stress of cultured cells. Useful such inhibitors include aurora kinase inhibitor II (4-(4'-benzamidoanilino)-6,7-dimethoxyquinazoline), SNS 314 mesylate (N-(3-Chlorophenyl)-N'-[5-[2-(thieno[3,2-d]pyrimidin-4-ylamino)ethyl]-2-thiazolyl]urea methanesulfonate), GSK1070916 (3-(4-(4-(2-(3-((dimethylamino)methyl)phenyl)-1H-pyrrolo[2,3-b]pyridin-4-yl)-1-ethyl-1H-pyrazol-3-yl)phenyl)-1,1-dimethylurea), TAK-901 (5-(3-

(ethylsulfonyl)phenyl)-3,8-dimethyl-N-(1-methylpiperidin-4-yl)-9H-pyrido[2,3-b]indole-7-carboxamide), RSK inhibitor II (a racemic mixture of dihydropteridinone 2-(3,5-difluoro-4-hydroxy-anilino)-8-isopentyl-5,7-dimethyl-7H-pteridin-6-one), and EPZ-5676 (9H-Purin-6-amine, 9-[5-deoxy-5-[[cis-3-[2-[6-(1,1-dimethylethyl)-1H-benzimidazol-2-yl]ethyl]cyclobutyl](1-methylethyl)amino]-β-D-ribofuranosyl]-), and combinations thereof. Of particular interest are aurora kinase inhibitor II, and RSK inhibitor II, and an inhibitor of DOT1L, particularly EPZ-5676. In a preferred embodiment of the invention, the small molecule is used in the medium of one or more of Stage 6 and 7 and more preferably in Stage 7. The amount of small molecule useful may be determined by selecting the amount showing the best expression of maturation markers and which amounts are not producing toxic effects. Typically, the amounts useful will be about 500 nM to 10 µM, alternatively, about 500 nM to 5 µM, and preferably about 500 nM to 2 µM.

Differentiation of Pluripotent Cells into Cells Expressing Markers Characteristic of Pancreatic Endocrine Cells with a Mature Phenotype Characteristics of pluripotent stem cells are well known to those skilled in the art, and additional characteristics of pluripotent stem cells continue to be identified. Pluripotent stem cell markers include, for example, the expression of one or more of the following: ABCG2, cripto, FOXD3, CONNEXIN43, CONNEXIN45, OCT4, SOX2, NANOG, hTERT, UTF1, ZFP42, SSEA-3, SSEA-4, TRA-1-60, TRA-1-81. These may be detectable by RT-PCR.

Exemplary pluripotent stem cells include the human embryonic stem cell line H9 (NIH code: WA09), the human embryonic stem cell line H1 (NIH code: WA01), the human embryonic stem cell line H7 (NIH code: WA07), and the human embryonic stem cell line SA002. Also suitable are cells that express at least one of the following markers characteristic of pluripotent cells: ABCG2, cripto, CD9, FOXD3, CONNEXIN43, CONNEXIN45, OCT4, SOX2, NANOG, hTERT, UTF1, ZFP42, SSEA-3, SSEA-4, TRA-1-60, and TRA-1-81.

Suitable for use in the present invention is a cell that expresses at least one of the markers characteristic of the definitive endoderm lineage. In one aspect of the present invention, a cell expressing markers characteristic of the definitive endoderm lineage is a primitive streak precursor cell. In an alternate aspect, a cell expressing markers characteristic of the definitive endoderm lineage is a mesendoderm cell. In an alternate aspect, a cell expressing markers characteristic of the definitive endoderm lineage is a definitive endoderm cell.

Also suitable for use in the present invention is a cell that expresses at least one of the markers characteristic of the pancreatic endoderm lineage. In one aspect of the present invention, a cell expressing markers characteristic of the pancreatic endoderm lineage is a pancreatic endoderm cell wherein the expression of PDX1 and NKX6.1 are substantially higher than the expression of CDX2 and SOX2. In certain embodiments, more than 30% of the cells express PDX1 and NKX6.1 and less than 30% of the cells express CDX2 or SOX2 as measured by FACS. Particularly useful are cells in which the expression of PDX1 and NKX6.1 is at least two-fold higher than the expression of CDX2 or SOX2.

Still also suitable for use in the present invention is a cell that expresses at least one of the markers characteristic of the pancreatic endocrine lineage. In one aspect of the invention, a cell expressing markers characteristic of the pancreatic endocrine lineage is a pancreatic endocrine cell. The pancreatic endocrine cell may be a pancreatic hormone-expressing cell meaning a cell capable of expressing at least one of the following hormones: insulin, glucagon, somatostatin, ghrelin, or pancreatic polypeptide. In a preferred embodiment, the pancreatic endocrine cell is an insulin-producing β cell.

In certain embodiments of the invention, to arrive at the cells expressing markers characteristic of the pancreatic endocrine beta cells of a mature phenotype, a protocol starting with pluripotent stem cells is employed. This protocol includes:

Stage 1: Pluripotent stem cells such as embryonic stem cells obtained from cell culture lines are treated with the appropriate factors to induce formation of definitive endoderm cells.

Stage 2: Cells resulting from Stage 1 are treated with the appropriate factors to induce formation of cells into markers expressing characteristic of gut tube cells.

Stage 3: Cells resulting from Stage 2 cells are treated with the appropriate factors to induce further differentiation into cells expressing markers characteristic of foregut endoderm cells.

Stage 4: Cells resulting from Stage 3 are treated with the appropriate factors to induce further differentiation into cells expressing markers characteristic of pancreatic foregut precursor cells. The cells are optionally cultured at the air-liquid interface at late Stage 4.

Stage 5: Cells resulting from Stage 4 are treated with the appropriate factors, including in certain embodiments: (i) one or more of T3, T4 or an analogue thereof; (ii) an ALK5 inhibitor; or (iii) both of (i) and (ii) and cultured, optionally and preferably at the air-liquid interface, to induce differentiation to cells expressing markers characteristic of pancreatic endoderm/endocrine precursor cells.

Stage 6: Cells resulting from Stage 5 cells are treated with the appropriate factors including in certain embodiments: (i) one or more of T3, T4 or an analogue thereof; (ii) an ALK5 inhibitor, (iii) one or more of an aurora kinase inhibitor, an RSK inhibitor and an inhibitor of protein methyltransferase DOT1L; (iv) both of (i) and (ii); (v) (i), (ii) and (iii); (vi) (i) and (iii); or (vii) (ii) and (iii) and cultured, optionally and preferably at the air-liquid interface, to induce differentiation into cells expressing markers characteristic of pancreatic endocrine cells.

Stage 7: Cells resulting from Stage 6 cells are treated with appropriate factors including in certain embodiments: (i) one or more of T3, T4 or thereof; (ii) an ALK5 inhibitor, (iii) an anti-oxidant, (iv) one or more of an aurora kinase inhibitor, an RSK inhibitor and an inhibitor of protein methyltransferase DOT1L; (v) (i) and (ii); (vi) (i) and (iii); (vii) (i) and (iv); (viii) (ii) and (iii); (ix) (ii) and (iv); (x) (i), (ii), and (iii); (xi) (i), (iii), and (iv): (xii) (ii), (iii), and (iv); (xiii) (i), (ii) and (iv); (xiv) (iii) and (iv); or (xv) (i), (ii), (iii) and (iv) and cultured, optionally and preferably at the air-liquid interface, to induce formation of pancreatic endocrine cells that express single hormonal insulin and are PDX1, NKX6.1 and MAFA positive and which have a higher level of expression of MAFA than the Stage 6 cells and the resulting cell population has a higher percentage of both MAFA positive and single hormonal insulin expressing cells than the Stage 6 cells.

While the invention in certain embodiments encompasses differentiating pluripotent stem cells (e.g. pre-Stage 1 cells) to Stage 7 cells, the invention also encompasses differentiating cells at other stages towards Stage 7. In particular, the invention encompasses differentiation of Stage 4 to Stage 7 cells. Moreover, although the process is described in discrete stages, the treatment, as well as the progress of the cells through the differentiation process, may be sequential or continuous. Moreover, differentiation of pluripotent stem cells to Stage 6 or Stage 7 cells can be carried out in suspension cultures.

The efficiency of differentiation may be determined by exposing a treated cell population to an agent, such as an antibody, that specifically recognizes a protein marker expressed by the differentiated cells of interest. Methods for assessing expression of protein and nucleic acid markers in cultured or isolated cells are standard in the art. These methods include RT-PCR, Northern blots, in situ hybridization (see, e.g., *Current Protocols in Molecular Biology* (Ausubel et al., eds. 2001 supplement)), and immunoassays such as immunohistochemical analysis of sectioned material, Western blotting, and for markers that are accessible in intact cells, flow cytometry analysis (FACS) (see, e.g., Harlow and Lane, *Using Antibodies: A Laboratory Manual*, New York: Cold Spring Harbor Laboratory Press (1998)).

The differentiated cells may also be further purified. For example, after treating pluripotent stem cells with the methods of the present invention, the differentiated cells may be purified by exposing a treated cell population to an agent, such as an antibody, that specifically recognizes a protein marker characteristically expressed by the differentiated cells being purified.

Any suitable growth medium containing sufficient quantities of vitamins, minerals, salts, glucose, amino acids and carrier proteins desirable for cells differentiation may be used for the various Stages 1 through 7. However, preferably, the following are used: Stage 1—MCDB-131 (available from (Life Technologies Corporation, Grand Island, N.Y.) or RPMI (available from Sigma-Aldrich)); Stage 2—MCDB-131 or Dulbecco's Modified Eagle's Medium F12 ("DMEM-F12"); Stage 3 through 5—MCDB-131, BLAR (Table 1), or DMEM; and Stages 6 and 7—BLAR or CMRL (Life Technologies). Preferably, the glucose concentration of the medium is kept at or, more preferably, lower than about 10 mM for Stages 1 through 4 and greater than about 10 mM for Stages 5 through 7.

Stage 1: Differentiation of pluripotent cells into cells expressing markers characteristic of definitive endoderm cells.

Pluripotent stem cells may be differentiated into cells expressing markers characteristic of definitive endoderm cells by any method known in the art, or by any method proposed in the invention. Methods reportedly useful for differentiating pluripotent stem cells into cells expressing markers characteristic of the definitive endoderm lineage are disclosed in: D'Amour et al., *Nature Biotechnology* 23, 1534-1541 (2005); Shinozaki et al., *Development* 131, 1651-1662 (2004); McLean et al., *Stem Cells* 25, 29-38 (2007); D'Amour et al., *Nature Biotechnology* 24, 1392-1401 (2006). Additional suitable differentiation methods are disclosed in: U.S. Patent App. Pub. No. 2007/0254359; U.S. Patent App. Pub. 2009/0170198; U.S. Patent App. Pub. 2011/0091971; U.S. Patent App. Pub. 2010/0015711; U.S. Patent App. Pub. 2012/0190111; U.S. Patent App. Pub. 2012/0190112; and U.S. Patent App. Pub. 2012/0196365. These disclosures are incorporated herein by reference in their entireties as they pertain to the differentiation of pluripotent stem cells into definitive endoderm cells.

In one embodiment, the pluripotent cells are treated with a suitable growth medium, preferably MCDB-131 or RPMI. The medium is preferably supplemented with a growth differentiation factor, such as growth differentiation factor 8 ("GDF8"), and a glycogen synthase kinase-3 β ("GSK3β") inhibitor, such as the cyclic aniline-pyridintriazine compounds disclosed in U.S. Patent App. Pub. No. 2010/0015711 (incorporated herein in its entirety by reference) to induce differentiation into cells expressing markers characteristic of definitive endoderm cells. A preferred GSK3β inhibitor is 14-prop-2-en-1-yl-3,5,7,14,17,23,27-heptaazatetracyclo[19.3.1.1~2,6~.1~8,12~]heptacosa-1 (25),2(27),3,5,8(26),9,11,21,23-nonaen-16-one ("MCX Compound"). Treatment may involve contacting pluripotent stem cells with a medium supplemented with about 50 ng/ml to about 150 ng/ml, alternatively about 75 ng/ml to about 125 ng/ml, preferably about 100 ng/ml of GDF8. The treatment may also involve contacting cells with about 0.1 to about 5 µM, alternatively about 0.5 to about 2.5 µM, preferably about 1 µM of MCX Compound. The pluripotent cells may be cultured for about two to five days, preferably about two to three days, to facilitate differentiation into cells expressing markers characteristic of the definitive endoderm cells.

In a preferred embodiment, the cells are cultured in the presence of GDF8 and MCX Compound for one day, followed by culturing in the presence of GDF8 and a lower concentration of MCX Compound for one day, followed by culturing in the presence of GDF8 for one day in the absence of MCX Compound. In particular, the cells are cultured in the presence of GDF8 and about 1 µM MCX Compound for one day, followed by culturing in the presence of GDF8 and about 0.1 µM MCX Compound for one day, followed by culturing in the presence of GDF8 for one day in the absence of MCX Compound. Alternatively, the cells may be cultured in the presence of GDF8 and about 1 µM MCX Compound for one day, followed by culturing in the presence of GDF8 and about 0.1 µM MCX Compound for one day.

Alternatively, the pluripotent stem cells may be cultured in medium containing activin A in the absence of serum, then culturing the cells with activin A and serum, and then culturing the cells with activin A and serum of a different concentration as disclosed in D'Amour et al., *Nature Biotechnology* 23, 1534-1541 (2005). As yet another alternative, the pluripotent stem cells may be differentiated into cells expressing markers characteristic of definitive endoderm cells by culturing the pluripotent stem cells in medium containing activin A in the absence of serum, then culturing the cells with activin A with serum as disclosed in D'Amour et al., *Nature Biotechnology*, 2005. Still further, pluripotent stem cells may be differentiated into cells expressing markers characteristic of the definitive endoderm lineage by culturing the pluripotent stem cells in medium containing activin A and a WNT ligand in the absence of serum, then removing the WNT ligand and culturing the cells with activin A with serum as disclosed in D'Amour et al., *Nature Biotechnology* 24, 1392-1401 (2006).

In one embodiment of the invention, pluripotent stem cells are treated with activin A and WNT3A to result in the formation of cells expressing markers characteristic of definitive endoderm cells. Treatment may involve contacting pluripotent stem cells with about 50 ng/ml to about 150 ng/ml, alternatively about 75 ng/ml to about 125 ng/ml, alternatively about 100 ng/ml of activin A. The treatment may also involve contacting the cells with about 10 ng/ml to about 50 ng/ml, alternatively about 15 ng/ml to about 30 ng/ml, alternatively about 20 ng/ml of WNT3A. The pluripotent cells may be cultured for approximately three days to arrive at the definitive endoderm cells. In one embodiment, the cells are cultured in the presence of activin A and WNT3A for one day followed by culturing in the presence of activin A (without WNT3A being present) for the remainder.

Formation of cells expressing markers characteristic of definitive endoderm cells may be determined by testing for the presence of the markers before and after following a particular protocol. Pluripotent stem cells typically do not express such markers. Thus, differentiation of pluripotent cells can be detected when cells begin to express markers characteristic of definitive endoderm.

Stage 2: Differentiation of cells expressing markers characteristic of definitive endoderm cells into cells expressing markers characteristic of gut tube cells.

The cells expressing markers characteristic of the definitive endoderm cells may be further differentiated into cells expressing markers characteristic of gut tube cells in a growth medium, such as MCDB-131 or DMEM F12. In one embodiment, the formation of cells expressing markers characteristic of gut tube cells includes culturing the cells expressing markers characteristic of the definitive endoderm cells with a medium containing fibroblast growth factor ("FGF"), preferably FGF7 or FGF10, to differentiate the cells. For example, the cell culture may include from about 10 ng/ml to about 75 ng/ml, alternatively from about 25 ng/ml to about 75 ng/ml, still alternatively from about 30 ng/ml to about 60 ng/ml, alternatively about 50 ng/ml of a fibroblast growth factor, preferably FGF7 or FGF10, more preferably FGF7, and most preferably about 25 ng/ml FGF7. The cells may be cultured under these conditions for about two to three days, preferably about two days.

In another embodiment, the formation of cells expressing markers characteristic of gut tube cells includes culturing the cells expressing markers characteristic of the definitive endoderm lineage with a fibroblast growth factor, preferably, FGF7 or FGF10, and ascorbic acid (Vitamin C). The culture medium may include from about 0.1 mM to about 0.5 mM ascorbic acid, alternatively from about 0.2 mM to about 0.4 mM ascorbic acid, alternatively about 0.25 mM of ascorbic acid. The cell culture may also include from about 10 ng/ml to about 35 ng/ml, alternatively from about 15 ng/ml to about 30 ng/ml, alternatively about 25 ng/ml of the fibroblast growth factor, preferably FGF7 or FGF10, more preferably FGF7. For example, the cell culture may include about 0.25 mM of ascorbic acid and about 25 ng/ml of FGF7. In one embodiment, the Stage 1 cells are treated for 2 days with FGF7 and ascorbic acid.

Stage 3: Differentiation of cells expressing markers characteristic of gut tube cells into cells expressing markers characteristic of foregut endoderm cells.

The gut tube cells resulting from carrying out Stage 2 may be further differentiated into Stage 3 cells, or cells expressing markers characteristic of the foregut endoderm, by culturing these cells in a growth medium such as MCDB-131, DMEM, or a custom media such as BLAR (Table I). The medium may be supplemented with: (i) a fibroblast growth factor, preferably, FGF7 or FGF10 and more preferably FGF7; (ii) retinoic acid ("RA"); (iii) a Sonic Hedgehog ("SHH") signaling pathway antagonist (such as Smoothened Antagonist 1 ("SANT-1") which is 1-piperazinamine, N-[(3,5-dimethyl-1-phenyl-1H-pyrazol-4-yl)methylene]-4-(phenylmethyl)- or ((E)-4-benxyl-N-((3,5-dimethyl-1-phenyl-1H-pyrazol-4-yl),ethylene-piperazin-1-amine), HPI-1 which is 2-methoxyethyl 1,4,5,6,7,8-hexahydro-4-(3hydroxyphenyl)-7-(2-methoxyphenyl)-2-methyl-5-oxo-3-quinolinecarboxylate, and preferably SANT-1; (iv) a protein kinase C ("PKC") activator, such as ((2S,5S)-(E,E)-8-(5-(4-(trifluoromethyl)phenyl)-2,4-pentadieneoylamino)benzolactam) ("TPB"), phorbol-12,13-dibutyrate ("PDBu"), phorbol-12-myristate-13-acetate ("PMA") or indolactam V ("ILV") and preferably TPB; (v) a bone morphogenic protein ("BMP") inhibitor, such as LDN-193189, Noggin, or Chordin and preferably LDN-193189; and (vi) ascorbic acid. Alternatively, a Smoothened ("SMO") receptor inhibitor (such as MRT10 (N[[[3-benzoylamino)phenyl]amino]thioxomethyl]-3,4,5-trimethoxybenzamide)) or cyclopamine may also be used. For example, the cell culture may include from about 100 nM to about 500 nM, alternatively from about 100 nM to about 400 nM, alternatively about 200 nM of a PKC activator. The cells may be cultured in the presence of these growth factors, small molecule agonists and antagonists for about two to four days, preferably about two to three days, more preferably about two days.

Alternatively, the Stage 2 cells may be differentiated into Stage 3 cells by culturing these cells in a culture medium supplemented with a SMO receptor inhibitor, SANT-1, retinoic acid, and Noggin. The cells may be cultured for approximately two to four days, preferably about two days.

In one embodiment, the medium is supplemented with: from about 10 ng/ml to about 35 ng/ml, alternatively from about 15 ng/ml to about 30 ng/ml, alternatively about 25 ng/ml of the fibroblast growth factor, preferably FGF7 or FGF10, more preferably FGF7; from about 0.1 mM to about 0.5 mM ascorbic acid, alternatively from about 0.2 mM to about 0.4 mM, alternatively about 0.25 mM of ascorbic acid; from about 0.1 µM to about 0.4 µM of SANT-1; from about 100 to about 300 nM of TPB; and from about 50 nM to about 200 nM, and about 100 nM of LDN-193189. In another embodiment, the medium is supplemented with about 25 ng/ml of FGF-7, about 1 µM of retinoic acid, about 0.25 µM of SANT-1, about 200 nM of TPB, about 100 nM of LDN-193189, and about 0.25 mM of ascorbic acid.

In one embodiment, the medium is supplemented with from about 0.1 µM to about 0.3 µM of SANT-1, from about 0.5 µM to about 3 µM of retinoic acid and from about 75 ng/ml to about 125 ng/ml of Noggin.

Stage 4 through Stage 7: Differentiation of cells expressing markers characteristic of foregut endoderm cells into cells expressing markers characteristic of a mature phenotype pancreatic endocrine cells by treatment with culture medium supplemented with one or both of a thyroid hormone and ALK inhibitor along with one or more of an aurora kinase inhibitor, an RSK inhibitor, and an inhibitor of protein methyltransferase DOT1L, preferably by culturing at the air-liquid interface.

Although in one embodiment, the present invention contemplates culturing at the air-liquid interface for all stages in the path for pluripotent cell to pancreatic endocrine cell, the invention preferably provides for the formation of Stage 1 to Stage 4 cells in planar or submerged culture and Stage 5, 6, and 7 cells by culturing the cells at the air-liquid interface. In other embodiments, the present invention relates to a stepwise method of differentiation pluripotent cells comprising culturing Stage 4, 5 and 6 cells at the air-liquid interface. In certain embodiments, cells cultured during Stages 4 through 7, may be cultured at the air-liquid interface. In other embodiments, only late Stage 4 to Stage 6 cells, or Stage 5 and Stage 6 cells, are cultured at the air-liquid interface. In yet another alternative embodiment, Stage 1 through 4 are carried out by culturing the cells in submerged planar cultures and Stage 5 through 7 are carried out by culturing in submerged suspension cultures.

Additionally, culturing during one or more, and preferably all of, Stages 5, 6, and 7 is carried out in the presence of one or more of T3, T4 and their analogues, an ALK5 inhibitor, or both one or more of T3, T4 and their analogues and an ALK5 inhibitor. In preferred embodiments, culturing during one or more, and preferably all of, Stages 5, 6, and 7 is preferably carried out in the presence of T3 and an ALK5 inhibitor and more preferably in the presence of T3 and ALK5 inhibitor II. Suitable amounts of the thyroid hormones or their analogues are about 0 to about 1000 nM, alternatively about 10 to about 900 nM, alternatively about 100 to about 800 nM, alternatively about 200 to about 700 nM, alternatively about 300 to about 600 nM, alternatively about 400 to about 500 nM, alternatively about 1 to about 500 nM, alternatively about 1 to about 100 nM, alternatively about 100 to about 1000 nM, alternatively about 500 to about 1000 nM, alternatively about 100 to about 500 nM, alternatively about 1 µM, and preferably about 0.1 to 1 µM. The amounts of ALK5 inhibitor are about 250 nM to 2 µM, alternatively about 300 to about 2000 nM, alternatively about 400 to about 2000 nM, alternatively about 500 to about 2000 nM, alternatively about 600 to about 2000 nM, alternatively about 700 to about 2000 nM, alternatively about 800 to about 2000 nM, alternatively about 1000 to about 2000 nM, alternatively about 1500 to about 2000 nM, alternatively about 250 to about 1000 nM, alternatively about 250 to about 500 nM, alternatively about 300 to about 1000 nM, alternatively about 400 to about 1000 nM, alternatively about 500 to about 1000 nM, alternatively about 600 to about 1000 nM, alternatively about 700 to about 1000 nM, alternatively about 800 to about 1000 nM, alternatively about 500 nM, alternatively about 10 µM, and preferably about 10 µM.

When cells are cultured at the air-liquid interface ("ALI"), the cells may be cultured on a porous substrate such that the cells are in contact with air on the top side and with cell culture media at the bottom side. For example, a sufficient volume of media may be added to the bottom of a culture vessel containing the porous substrate (e.g. a filter insert) such that the media contacts the bottom surface of cells residing on the substrate but does not encapsulate or submerge them. Suitable porous substrates can be formed of any material that will not adversely affect the growth and differentiation of the cells. Exemplary porous substrates are made of polymers such as polyethylene terephthalate ("PET"), polyester, or polycarbonate. Suitable porous substrates may be coated or uncoated. In one embodiment, the coating may be MATRIGEL™. In one embodiment of the invention, the porous substrate is a porous filter insert, which may be coated with MATRIGEL™. In one embodiment of the invention, the porous substrate is an uncoated filter insert. The porosity of the substrate should be sufficient to maintain cell viability and promote differentiation of the cells. Suitable substrates include filter inserts having a pore size of from about 0.3 to about 3.0 µm, from about 0.3 to about 2.0 µm, about 0.3 to about 1.0 µm, from about 0.3 to about 0.8 µm, from about 0.3 to about 0.6 µm, from about 0.3 to about 0.5 µm, from about 0.3 to about 3.0 µm, from about 0.6 to about 3.0 µm, from about 0.8 to about 3.0 µm, from about 1.0 to about 3.0 µm, from about 2.0 to about 3.0 µm, preferably about 0.4 µm and a pore density of from about 50 to about 120 million pores/cm$^2$, from about 60 to about 110 million pores/cm$^2$, from about 70 to about 100 million pores/cm$^2$, preferably from about 80 to about 100 million pores/cm$^2$, from about 90 to about 100 million pores/cm$^2$, and more preferably about 100 million pores/cm$^2$.

The media may be exchanged or refreshed every other day or, preferably, daily. The cells grown on top of the porous substrate are generally not single cells, but rather they are in the form of a sheet or exist as an aggregate cell cluster. Cells cultured at the ALI may experience higher oxygen tension as compared to cells submerged in media.

The present invention encompasses formation of Stage 4 to 7, preferably Stage 5 to 7, cells at the air-liquid interface. The cells may be formed by differentiating pluripotent stem cells or by further differentiating Stage 3, 4, 5, or 6 cells. Stage 4 cells may be cultured entirely at the air-liquid interface or the cells may be cultured in submerged planar culture during the early portion of Stage 4, meaning about one to two days and then cultured at the air-liquid interface for the latter portion of Stage 4, meaning about day two to day three. Preferably, Stage 4 is not carried out at the ALI, but rather in submerged culture.

In one embodiment, the present invention provides a method for producing cells expressing markers characteristic of pancreatic endocrine cells from pluripotent stem cells, comprising culturing pluripotent stem cells, differentiating the pluripotent stem cells into cells expressing markers characteristic of the foregut endoderm; differentiating the cells expressing markers characteristic of the foregut endoderm into cells expressing markers characteristic of the pancreatic endocrine cells by culturing, optionally, at the air-liquid interface. The method may include treatment with a medium supplemented with one or both of (i) T3, T4 or their analogues, (ii) an ALK5 inhibitor, or both (i) and (ii). The method may include differentiating the cells expressing markers characteristic of foregut endoderm cells (Stage 3 cells) into cells expressing markers characteristic of pancreatic foregut precursor cells (Stage 4 cells) by treatment with a medium supplemented with (i) one or both of T3, T4 or their analogues, (ii) ALK5 inhibitor or both (i) and (ii) and culturing in a planar culture. The method may also include differentiating cells expressing markers characteristic of pancreatic foregut precursor cells (Stage 4 cells) into cells expressing markers characteristic of the pancreatic endocrine cells (Stage 6 cells) by treatment with a medium supplemented with (i) one or both of T3, T4 or their analogues, (ii) ALK5 inhibitor or both (i) and (ii) and culturing in a planar culture or, and preferably, culturing at the air-liquid interface. The method further includes differentiating Stage 6 cells into cells expressing markers characteristic of pancreatic endocrine cells and that have a more mature phenotype as compared to Stage 6 (Stage 7 cells) by treatment with a medium supplemented with (i) one or both of T3, T4 or their analogues, (ii) ALK5 inhibitor or both (i) and (ii) along with an one or more of an aurora kinase inhibitor, an RSK inhibitor, and an inhibitor of protein methyltransferase DOT1L and, optionally but preferably an anti-oxidant such as Vitamin E or, preferably, acetyl cysteine. The amount of acetyl cysteine that is useful is about 0.1 to about 2 mM. The amount of Vitamin E is about 0.1 to about 10 µM. In yet another embodiment, the method further includes carrying out Stage 6 by treatment of Stage 5 cells with a medium supplemented with (i) one or both of T3, T4 or their analogues, (ii) ALK5 inhibitor or both (i) and (ii) along with one or more of an aurora kinase inhibitor, an RSK inhibitor, and an inhibitor of protein methyltransferase DOT1L. In still another embodiment, Stage 6 is carried out by treatment of Stage 5 cells with a medium supplemented with (i) one or both of T3, T4 or their analogues, (ii) ALK5 inhibitor or both (i) and (ii) along with one or more of an aurora kinase inhibitor, an RSK inhibitor, and an inhibitor of protein methyltransferase DOT1L followed by carrying out Stage 7 by treatment with a medium supplemented with (i) one or both of T3, T4 or their analogues, (ii) ALK5 inhibitor or both (i) and (ii) along with an one or more of an aurora kinase inhibitor, an RSK inhibitor, and an inhibitor of protein methyltransferase DOT1L and, optionally but preferably an anti-oxidant such as Vitamin E or, preferably, acetyl cysteine.

One embodiment of the invention is a method of forming pancreatic endocrine cells expressing markers characteristic of maturing beta cells (Stage 7 cells) comprising differentiating cells expressing markers characteristic of the pancreatic foregut precursor cells (Stage 4 cells) into cells expressing markers characteristic of Stage 7 cells by culturing, preferably at the air-liquid interface. In another embodiment, the methods of the invention result in the formation of Stage 6 cells, or cells that are immature beta cells. The method, preferably at least during Stages 5 through 7, includes treatment with a medium supplemented with T3, T4, or an analogue thereof, an ALK5 inhibitor, or both.

Culturing of the cells at the air-liquid interface includes seeding the cells on a porous substrate such as a porous filter insert. In certain embodiments, the substrate pore size may range from about 0.3 to about 3 microns. Seeding may be accomplished by releasing cells as single cells from monolayer cultures or clusters of cells from monolayer cultures into a suspension and subsequently aliquoting the single cell suspension or suspended cell culture onto a porous substrate at the ALI. The cells may be seeded onto the porous substrate from a suspension having about 1000 cells/μl to about 100,000 cells/μl, about 1000 cells/μl to about 90,000 cells/μl, about 1000 cells/μl to about 80,000 cells/μl, about 1000 cells/μl to about 70,000 cells/μl, about 1000 cells/μl to about 60,000 cells/μl, about 1000 cells/μl to about 50,000 cells/μl, about 1000 cells/μl to about 40,000 cells/μl, about 1000 cells/μl to about 30,000 cells/μl, about 1000 cells/μl to about 20,000 cells/μl, about 1000 cells/μl to about 10,000 cells/μl, about 1000 cells/μl to about 5000 cells/μl, about 5000 cells/μl to about 100,000 cells/μl, about 10,000 cells/μl to about 100,000 cells/μl, about 20,000 cells/μl to about 100,000 cells/μl, about 30,000 cells/μl to about 100,000 cells/μl, about 40,000 cells/μl to about 100,000 cells/μl, about 50,000 cells/μl to about 100,000 cells/μl, about 60,000 cells/μl to about 100,000 cells/μl, about 20,000 cells/μl to about 80,000 cells/μl, about 30,000 cells/μl to about 70,000 cells/μl, about 40,000 cells/μl to about 60,000 cells/μl, and preferably about 50,000 cells/μl. The cells may be seeded as droplets of the cell suspension containing individual cells or aggregates or clusters of cells. The resulting cell deposit may contain about $5\times10^6$ to about $5\times10^7$ cells/cm$^2$, about $6\times10^6$ to about $5\times10^7$ cells/cm$^2$, about $7\times10^6$ to about $5\times10^7$ cells/cm$^2$, about $8\times10^6$ to about $5\times10^7$ cells/cm$^2$, about $9\times10^6$ to about $5\times10^7$ cells/cm$^2$, about $1\times10^7$ to about $5\times10^7$ cells/cm$^2$, about $2\times10^7$ to about $5\times10^7$ cells/cm$^2$, about $3\times10^7$ to about $5\times10^7$ cells/cm$^2$, about $4\times10^7$ to about $5\times10^7$ cells/cm$^2$, about $5\times10^6$ to about $4\times10^7$ cells/cm$^2$, about $5\times10^6$ to about $3\times10^7$ cells/cm$^2$, about $5\times10^6$ to about $2\times10^7$ cells/cm$^2$, about $5\times10^6$ to about $1\times10^7$ cells/cm$^2$, about $5\times10^6$ to about $9\times10^6$ cells/cm$^2$, about $5\times10^6$ to about $8\times10^6$ cells/cm$^2$, about $5\times10^6$ to about $7\times10^6$ cells/cm$^2$, about $5\times10^6$ to about $6\times10^6$ cells/cm$^2$, about $7\times10^6$ to about $4\times10^7$ cells/cm$^2$, about $8\times10^6$ to about $3\times10^7$ cells/cm$^2$, about $9\times10^6$ to about $2\times10^7$ cells/cm$^2$, and preferably on the order of about $1\times10^7$ cells/cm$^2$.

In another embodiment, the invention refers to a method of enhancing the number of single hormone positive cells (e.g. cells that co-express NKX6.1 and insulin or cells that co-express NKX6.1 and chromogranin by culturing and differentiating a population of PDX1 and NKX6.1 co-expressing cells, preferably at an air-liquid interface. In another embodiment, pancreatic endoderm cells cultured at the air-liquid interface are further differentiated to pancreatic endocrine cells by treatment with a compound selected from the following: ALK5 inhibitor, BMP inhibitor, gamma-secretase inhibitor, Ephrin ligands, EphB inhibitor, PKC inhibitor, EGFr inhibitor, retinoic acid, vitamin C, T3/T4, glucose, cell cycle regulators, WNT regulators, SHH inhibitor, aurora inhibitor, anti-oxidants, vitamin E, acetyl-cysteine, or combinations thereof.

In further embodiments, the present invention relates to a stepwise method of differentiating pluripotent cells that includes culturing Stage 4 through Stage 6 cells in a media containing sufficient amounts of (i) one or more of T3, T4 and their analogues, (ii) an ALK5 inhibitor, or both (i) and (ii) and further culturing the Stage 6 cells in a media that optionally, and preferably, contains one or more of an aurora kinase inhibitor, an RSK inhibitor, and an inhibitor of protein methyltransferase DOT1L, and an antioxidant to generate pancreatic endocrine cells and populations of pancreatic endocrine cells that express insulin, PDX1, NKX6.1, and MAFA.

In some embodiments, at least 10% of the cells of the resulting cell population express insulin, PDX1, NKX6.1, and MAFA. In other embodiments, at least 20% of the cells of the population express insulin, PDX1, NKX6.1, and MAFA. In other embodiments, at least 30% of the cells of the population express insulin, PDX1, NKX6.1, and MAFA. In still other embodiments, at least 40% of the cells of the population express insulin, PDX1, NKX6.1, and MAFA. In yet other embodiments, at least 50% of the cells of the population express insulin, PDX1, NKX6.1, and MAFA. In alternative embodiments, at least 60% of the cells express insulin, PDX1, NKX6.1, and MAFA. In still other alternative embodiments, at least 70% of the cells of the population express insulin, PDX1, NKX6.1, and MAFA. In yet other embodiments, at least 80% of the cells of the population express insulin, PDX1, NKX6.1, and MAFA. In other embodiments, at least 90% of the cells of the population express insulin, PDX1, NKX6.1, and MAFA. In alternative embodiments, at least 91, 92, 93, 94, 95, 96, 97, 98, or 99% of the cells of the population express insulin, PDX1, NKX6.1, and MAFA.

Stage 4: Differentiation of cells expressing markers characteristic of foregut endoderm cells into cells expressing markers characteristic of pancreatic foregut precursor cells.

In one embodiment, the methods of the invention include treating Stage 3 cells with a differentiation medium that may be any suitable growth medium and preferably is MCDB-131, DMEM, or a custom media such as BLAR (Table I). The medium may be supplemented with one or more of the following: (a) an ALK5 inhibitor selected from the group consisting of: TGF-β receptor inh V, TGF-β receptor inh I, TGF-β receptor inh IV, TGF-β receptor inh VII, TGF-β receptor inh VIII, TGF-β receptor inh II, TGF-β receptor inh VI, TGF-β receptor inh III, TGF-β inhibitor SB431542, SD-208, ITD-1, LY2109761, A83-01, LY2157299, ALK5i and ALK5 inhibitor II; (b) a thyroid hormone selected from the group consisting of: T3, T4, analogues of T3, analogues of T4 and mixtures thereof (c) a SHH signaling pathway antagonist selected from SANT-1 or HIP-1; (d) a BMP receptor inhibitor selected from LDN-193189, Noggin or Chordin; (e) a PKC activator selected from TPB, PPBu, PMA, and ILV; (f) a fibroblast growth factor selected from FGF-7 or FGF-10; (g) retinoic acid; and (h) ascorbic acid. For example, a growth medium such as MCDB131 or, and preferably, BLAR may be supplemented with a SHH signaling pathway antagonist (such as SANT-1 or HPI-1), a BMP inhibitor (such as LDN-193189, Noggin or Chordin), ascorbic acid, and a PKC activator (such as TPB, PDBu. PMA or ILV), to provide a useful differentiation media. Culturing Stage 3 cells in such medium for about two to four days, preferably about two to three days, more preferably about three days usually is sufficient to differentiate the Stage 3 cells into Stage 4 cells. In another embodiment, the medium may be supplemented with a SMO inhibitor and SHH signaling pathway antagonist. In a preferred embodiment, the Stage 3 cells may be treated with a medium supplemented with about 0.25 µM SANT-1; about 100 nM RA; about 2 ng/ml FGF7; about 100 nM LDN-193189; and about 0.25 mM ascorbic acid; and about 200 nM for three days.

In Stage 4, cells may be cultured at the air-liquid interface, either during the entire stage or, and preferably, after about 2 to 3 days of planar culturing. Specifically, the present invention provides an in vitro cell culture for differentiating cells derived from pluripotent stem cells at the air-liquid interface comprising: (a) a culture vessel; (b) a volume of growth medium within said vessel sufficient to fill only a portion of the volume of the vessel; (c) air within the vessel that fills a portion of the vessel adjoining the medium; (d) a porous substrate located at the interface between the medium and the air; and (e) cells derived from pluripotent stem cells disposed upon the surface of the substrate such that the medium contacts only a portion of the surface of the cells. Alternatively, Stage 4 may be carried out entirely in planar culture.

In a further embodiment, the cells at the completion of Stage 4 may be treated with a Rho-associated kinase ("ROCK") inhibitor such as Y27632 ((1R,4r)-4-((R)-1-aminoethyl)-N-(pyridin-4-yl)cyclohexanecarboxamide), GSK269962 (N-[3-[[2-(4-Amino-1,2,5-oxadiazol-3?-yl)-1-ethyl-1H-imidazo[4,5-c]pyridin-6-yl]oxy]phenyl]-4-[2-(4-morpholinyl)ethoxy]benzamide), H1152 ((S)-(+)-2-Methyl-1-[(4-methyl-5-isoquinolinyl)sulfonyl]homopiperazine, 2HCl) and, SR3677 (N-[2-[2-(Dimethylamino)ethoxy]-4-(1H-pyrazol-4-yl)phenyl-2,3-dihydro-1,4-benzodioxin-2-carboxamide dihydrochloride). In certain embodiments about 1 to 20 µM, alternatively about 1 to 15 µM, alternatively about 1 to 10 µM, preferably about 10 µM of the ROCK inhibitor may be used.

In certain embodiments, only late Stage 4 cells, meaning cells that have been cultured for 1 to 2 days in planar cultures, may subsequently be cultured at the air-liquid interface for completion of Stage 4. In one embodiment, only late Stage 4 cells that were treated with a ROCK inhibitor are cultured at the air-liquid interface. In other embodiments, 0.5 to about $0.75 \times 10^5$ cells/micro liter are seeded to be cultured at the air-liquid interface; alternatively, about 2 to $6 \times 10^6$ cells are seeded to be cultured at the air-liquid interface. In certain embodiments, the cells may be treated with a cell detachment solution, such as a solution containing proteolytic and collagenolytic enzymes such as TrypLE™, Accutase™, or Dispase™ prior to culturing at the air-liquid interface.

In an alternate embodiment, Stage 3 cells may be treated with a differentiation medium comprising a growth medium supplemented with an ALK5 inhibitor, Noggin, and a PKC activator, such as TPB. In certain embodiments, the medium may be supplemented with about 0.1 µM ALK5 inhibitor, about 100 ng/mL of Noggin, and about 500 nM TPB. The cell culture may be in a monolayer format. The treatment may last for a total of about three days. In certain embodiments, the cells may be treated for two days and then on the last day the cells may be treated with proteolytic enzymes, collagenolytic enzymes or both, such as Dispase™, and broken into cell clusters having a diameter of less than about 100 microns followed by culturing in the presence of an ALK5 inhibitor and LDN-193189. In certain embodiments, the cell clusters having a diameter of less than about 100 microns may be cultured in a medium supplemented with about 200 nM ALK5 inhibitor and about 100 nM LDN-193189. In an alternate embodiment, culturing Stage 4 cells at the air-liquid interface may significantly enhance pancreatic endoderm markers along with endocrine-related markers. Accordingly, the invention provides for methods of enhancing pancreatic endoderm and endocrine-related markers by culturing Stage 4 cells at the air-liquid interface Stage 5: Differentiation of cells expressing markers characteristic of pancreatic foregut precursor cells into cells expressing markers characteristic of pancreatic endoderm/endocrine precursor cells.

In one embodiment, the methods of the invention include treating Stage 4 cells with a differentiation medium that may be any suitable growth medium and preferably is MCDB-131, DMEM or, and preferably, a custom media such as BLAR (Table I). The medium may be supplemented with one or more of the following: (a) an ALK5 inhibitor selected from the group consisting of: TGF-β receptor inh V, TGF-β receptor inh I, TGF-β receptor inh IV, TGF-β receptor inh VII, TGF-β receptor inh VIII, TGF-β receptor inh II, TGF-β receptor inh VI, TGF-β receptor inh III, TGF-β inhibitor SB431542, SD-208, ITD-1, LY2109761, A83-01, LY2157299, ALK5i and ALK5 inhibitor II; (b) a thyroid hormone selected from the group consisting of T3. T4, analogues of T3, analogues of T4 and mixtures thereof; (c) a SHH signaling pathway antagonist selected from SANT-1 or HIP-1; (d) a BMP Receptor Inhibitor selected from LDN-193189, Noggin or Chordin; (e) retinoic acid; (f) ascorbic acid; (g) heparin; and (h) zinc sulfate, and culturing the cells, preferably at the air-liquid interface, for about two to four days, preferably about three days, to differentiate the cells into Stage 5 cells. In another embodiment, the growth medium is also supplemented with one or both of a SMO inhibitor (such as MRT10 or cyclopamine) and a fibroblast growth factor preferably selected from FGF-7 or FGF-10. The treatment of the Stage 4 cells is carried out for about two to four days, preferably about 3 days to differentiate the cells into Stage 5 cells.

In a preferred embodiment, the Stage 4 cells are differentiated into Stage 5 cells by treating the cells with a medium supplemented with from about 0.1 µM to about 0.4 µM of SANT-1 and preferably about 0.25 µM SANT-1, about 50 nM RA, from about 0.1 mM to about 0.5 mM ascorbic acid, alternatively from about 0.2 mM to about 0.4 mM and preferably about 0.25 mM ascorbic acid, from about 50 nM to about 200 nM and preferably about 100 nM LDN-193189, about 1 µM of T3, and about 10000 nM ALK5 inhibitor, more preferably ALK 5 inhibitor II. In still another embodiment, the cells are optionally and preferably also treated with about 1 to 15 µM, alternatively about 1 to 10 µM ZnSO$_4$, alternatively about 5 to 10 µM, preferably about 10 µM about 10 µM zinc sulfate and about 1 to 100 µg/ml, preferably about 10 µg/ml of heparin. The treatment of the Stage 4 cells is carried out for about two to four days, preferably about 3 days to differentiate the cells into Stage 5 cells.

In yet another embodiment, the methods of the invention include treating Stage 4 cells with a medium supplemented with heparin, a SMO inhibitor or SHH signaling pathway antagonist, RA, a BMP receptor inhibitor and an ALK5 inhibitor and culturing the cells at the air-liquid interface for about 3 days to differentiate the cells into Stage 5 cells. In an alternative embodiment, the medium may be supplemented with both a SMO inhibitor and an SHH signaling pathway antagonist, along with RA, a BMP receptor inhibitor and an ALK5 inhibitor. Thus, in one embodiment, the Stage 4 cells may be differentiated into Stage 5 cells by treating the Stage 4 cells with a medium supplemented with heparin, $ZnSO_4$, a SMO inhibitor or SHH signaling pathway antagonist. RA, LDN-193189 and ALK5 inhibitor II. In an alternative embodiment, the medium may be supplemented with both a SMO inhibitor and SHH signaling pathway antagonist. In one embodiment, the Stage 4 cells are differentiated into Stage 5 cells by treating the cells with a medium supplemented with about 10 μg/ml of heparin, about 0.25 μM SANT-1, about 50 nM RA, about 50 nM LDN-193189, about 10 nM of T3 and about 1000 nM ALK5 inhibitor. Suitable ALK5 inhibitors include but are not limited to SD-208, ALK5 inhibitor II, TGF-β receptor inh V, TGF-β receptor inh I, TGF-β receptor inh IV, TGF-1 receptor inh VII, TGF-β receptor inh VIII, TGF-β receptor inh II, TGF-β receptor inh VI, TGF-β 3 receptor inh III and combinations thereof. The treatment of the Stage 4 cells is carried out for about two to four days, preferably about 3 days to differentiate the cells into Stage 5 cells.

In a preferred embodiment, the ALK5 inhibitor is ALK5 inhibitor II. In another preferred embodiment, about 10000 nM of ALK5 inhibitor II is used. In an alternate preferred embodiment, the Stage 4 cells are treated with a medium supplemented with about 10 μg/ml of heparin, about 0.25 μM SANT-1, about 50 nM RA, about 100 nM LDN-193189, and about 10000 nM of ALK5 inhibitor II. In yet another alternate embodiment, the methods of the invention include treating Stage 4 cells with a medium supplemented with a SMO inhibitor or SHH signaling pathway antagonist, RA, and an ALK5 inhibitor and culturing the cells, preferably at the air-liquid interface for about two days to four days, preferably about 3 days, differentiate the cells into Stage 5 cells. In an alternate embodiment, the medium may be supplemented with both a SMO inhibitor and SHH signaling pathway antagonist. In one embodiment, the Stage 4 cells are differentiated into Stage 5 cells by treating the cells with a medium supplemented with about 0.25 μM SANT-1, about 50 nM RA, about 50 nM LDN-193189, about 1 μM T3 and about 1000 nM of an ALK5 inhibitor.

The amount of cells seeded for culturing at the air-liquid interface may vary. For example, to culture the cells at the air-liquid interface, droplets of a cell suspension containing about 0.5 to $6 \times 10^5$ cells/μl may be seeded on a porous substrate (e.g. filter). The suspension may contain from about $2 \times 10^5$ cells/μl to about $6 \times 10^5$ cells/μl; about $4 \times 10^7$ cells/μl to about $6 \times 10^5$ cells/μl; about $5 \times 10^5$ cells/μl to about $6 \times 10^5$ cells/μl; about $5 \times 10^5$ cells/μl to about $6 \times 10^7$ cells/μl; about $2 \times 10^5$ cells/μl to about $5 \times 10^5$ cells/μl; about $2 \times 10^5$ cells/μl to about $4 \times 10^7$ cells/μl; or about $3 \times 10^5$ cells/μl that may be seeded onto a porous substrate such as a filter located at the air-liquid interface. In some embodiments, droplets of a cell suspension containing from about $0.5 \times 10^5$ cells/μl to about $0.75 \times 10^5$ cells/μl; about $0.6 \times 10^7$ cells/μl to about $0.75 \times 10^5$ cells/μl; or about $0.5 \times 10^5$ cells/μl to about $0.6 \times 10^5$ cells/μl are seeded onto a porous support to be cultured at the ALI.

In another embodiment, the methods of the invention include treating Stage 4 cells with a medium supplemented with a BMP receptor inhibitor (e.g. LDN-193189, Noggin or Chordin) and an ALK5 inhibitor for about 1 day to differentiate Stage 4 cells into Stage 5 cells. For example, the medium may be supplemented with about 100 nM of LDN-193189 and with about 100 nM of ALK5 inhibitor and about 1 μM T3. The cells may be in the form of clusters. In certain embodiments, the cells may be treated with a cell detachment solution, such as a solution containing proteolytic and collagenolytic enzymes prior to culturing at the air-liquid interface.

In accordance with the foregoing method, the invention further provides a cell culture for differentiating cells expressing markers characteristic of the pancreatic foregut precursor into cells expressing markers characteristic of pancreatic endoderm/pancreatic endocrine precursor cells comprising: (a) a culture vessel; (b) a volume of growth medium within said vessel sufficient to fill only a portion of the volume of said vessel; (c) air within said vessel that fills a portion of said vessel adjoining said medium; (d) a porous substrate located at the interface between said medium and said air; and (e) cells expressing markers characteristic of pancreatic foregut precursor cells derived from pluripotent stem cells disposed upon the surface of said substrate such that said medium contacts only a portion of the surface of said cells.

Stage 6: Differentiation of cells expressing markers characteristic of pancreatic endoderm/endocrine precursor cells into cells expressing markers characteristic of pancreatic endocrine cells.

In one embodiment, the methods of the invention include treating Stage 5 cells with a differentiation medium that may be any suitable growth medium, preferably such as MCDB-131 or CMRL, and more preferably, a custom media such as BLAR (Table I). The medium may be supplemented with one or more of the following: (a) an ALK5 inhibitor selected from the group consisting of: TGF-β receptor inh V, TGF-β receptor inh I, TGF-β receptor inh IV, TGF-β receptor inh VII, TGF-β receptor inh VIII. TGF-β receptor inh II, TGF-β receptor inh VI, TGF-β receptor inh III, TGF-β inhibitor SB431542, SD-208, ITD-1, LY2109761, A83-01, LY2157299, ALK5i and ALK5 inhibitor II; (b) a thyroid hormone selected from the group consisting of T3. T4, analogues of thereof and mixtures thereof; (c) a BMP receptor inhibitor preferably selected from LDN-193189, Noggin or Chordin; (d) a gamma secretase inhibitor such gamma secretase inhibitor XX, gamma secretase inhibitor XXI, gamma secretase inhibitor XVI, or DAPT; (e) ascorbic acid; (f) heparin; and (g) zinc sulfate and culturing, preferably at the air-liquid interface, for about two to four, preferably for about three days, to differentiate the Stage 5 cells into Stage 6 cells. Optionally, the medium can additionally be supplemented with one or more of an SHH signaling pathway antagonist, a smoothened receptor inhibitor, a fibroblast growth factor, and retinoic acid.

In a preferred embodiment, the Stage 5 cells may be differentiated into Stage 6 cells by treatment with a medium supplemented with about 50 nM RA, about 0.25 mM ascorbic acid, about 100 nM LDN-193189, about 10000 nM of ALK5 inhibitor and preferably ALK 5 inhibitor II, 1 μM T3, about 100 nM of a gamma secretase inhibitor for about seven days. Alternatively, Stage 5 cells may be differentiated into Stage 6 cells by treatment with a medium supplemented with about 0.25 µM SANT-1, about 50 nM RA, about 0.25 mM ascorbic acid, about 1000 nM ALK5 inhibitor and 1 µM T3 for about three days. The cells may be cultured in such media for an additional two days, or more, if desired.

Alternatively, Stage 5 cells may be differentiated into Stage 6 cells by treatment with a medium supplemented with heparin, a SMO inhibitor or SHH signaling pathway antagonist, a BMP inhibitor, T3, T4, analogues thereof and mixtures thereof and an ALK5 inhibitor and culturing, preferably at the air-liquid interface, for about one to seven days, alternatively about six days, alternatively about seven days. In an alternate embodiment, the medium may be supplemented with both a SMO inhibitor and SHH signaling pathway antagonist. For example, the cells may be cultured in the medium supplemented with about 10 µg/ml of heparin, about 0.25 µM SANT-1, about 100 nM LDN-193189, about 1000 nM of T3 and about 500 to about 10,000 nM, alternatively about 500 nM, alternatively about 1000 mM, and alternatively about 10,000 nM of an ALK5 inhibitor. Suitable ALK5 inhibitors include but are not limited to SD-208, ALK5 inhibitor II, TGF-β receptor inh V, TGF-β receptor inh I, TGF-β receptor inh IV, TGF-β receptor inh VII, TGF-β receptor inh VIII, TGF-β receptor inh II, TGF-β receptor inh VI, TGF-β receptor inh III and combinations thereof.

In a preferred embodiment, the ALK5 inhibitor is ALK5 inhibitor II. In a more preferred embodiment, about 10000 nM of ALK5 inhibitor II is used. Accordingly, in one embodiment, Stage 5 cells may be differentiated into Stage 6 cells by treatment with a medium supplemented with heparin, SMO inhibitor or SHH signaling pathway antagonist, a BMP inhibitor, T3, T4, analogues thereof and mixtures thereof, and ALK5 inhibitor and culturing, preferably at the air-liquid interface, preferably for about seven days. In an alternate embodiment, the medium may be supplemented with both an SMO inhibitor and SHH signaling pathway antagonist. In certain embodiments, the cells may be treated with a cell detachment solution, such as a solution containing proteolytic and collagenolytic enzymes prior to culturing at the air-liquid interface.

In another embodiment, Stage 5 cells may be differentiated into Stage 6 cells by treatment with a medium supplemented with heparin, a SMO inhibitor or SHH signaling pathway antagonist, a BMP inhibitor, T3, T4, and ALK5 inhibitor II and culturing at the air-liquid interface for about 5 days to about 7 days, alternatively about 5 days, alternatively about 6 days, alternatively about 7 days In these embodiments, the medium may be supplemented with about 10 µg/ml of heparin, about 0.25 µM SANT-1, about 100 nM LDN-193189, about 1000 nM of T3 and about 10,000 nM of ALK5 inhibitor II. In certain embodiments, the medium may be further supplemented with Zinc sulfate ($ZnSO_4$). For example, the medium may be further supplemented with about 10 mM $ZnSO_4$. In an alternate embodiment, the medium may be supplemented with both a SMO inhibitor and SHH signaling pathway antagonist In a particularly preferred embodiment of the invention, one or more of an aurora kinase inhibitor, preferably aurora kinase inhibitor II, an RS K inhibitor, preferably RS K inhibitor II and an inhibitor of protein methyltransferase DOT1L, preferably EPZ-5676, is added to the medium. The amount added may be from about 100 to 5000 nM, alternatively about 1000 to 5000 nM, alternatively about 2000 to 5000 nM, alternatively about 3000 to 5000 nM, and preferably about 1000 to 2000 nM for the aurora kinase and RSK inhibitors and about 100 to 1000 nM for the DOT1L inhibitor, and more preferably about 1 µM to about 10 nM.

In accordance with the foregoing method, the invention further provides a cell culture for differentiating cells expressing markers characteristic of pancreatic endoderm/endocrine precursor cells into cells expressing markers characteristic of pancreatic endocrine cells, comprising: (a) a culture vessel; (b) a volume of growth medium within said vessel sufficient to fill only a portion of the volume of said vessel; (c) air within said vessel that fills a portion of said vessel adjoining said medium; (d) a porous substrate located at the interface between said medium and said air; and (d) cells expressing markers characteristic of pancreatic endoderm/endocrine precursor cells derived from pluripotent stem cells disposed upon the surface of said substrate such that said medium contacts only a portion of the surface of said cells.

In one embodiment, Stage 5 cells cultured according to embodiments of the invention are utilized and differentiated into Stage 6 cells, while in other embodiments Stage 5 cells cultured according to other protocols may be utilized.

In another embodiment, the methods of the invention result in the formation of Stage 6 cells that are single-hormone positive. Thus, in one embodiment, the methods of the invention result in Stage 6 cells, which co-express NKX6.1, insulin, chromogranin and PDX1. In another embodiment, the methods of the invention result in Stage 6 cells, which co-express NKX6.1 and insulin. In certain embodiments of the invention, the method employs BLAR a custom medium (see Table I) at Stages 4 to 6 or late Stage 4 to 6, or Stages 5 and 6. The medium may be, and preferably is, exchanged every day or alternatively every other day.

In another embodiment, the invention relates to a method of forming Stage 6 cells co-expressing NKX6.1 and chromogranin comprising culturing Stage 4, preferably late Stage 4 cells to Stage 6 cells at the air-liquid interface. In yet another embodiment, the invention relates to a method of forming single hormone insulin positive cells expressing NKX6.1 Stage 6 cells by culturing Stage 4, preferably late Stage 4 cells, to Stage 6 cells at the air-liquid interface.

Stage 7: Differentiation of cells expressing markers characteristic of pancreatic endocrine cells to cells expressing markers characteristic of pancreatic endocrine cells having a more mature phenotype.

In one embodiment, the methods of the invention include treating Stage 6 cells with a differentiation medium that may be any suitable growth medium, preferably such as MCDB-131 or CMRL or, and more preferably, a custom media such as BLAR (Table I) The medium is supplemented with one or more of the following: (a) an ALK5 inhibitor selected from the group consisting of: TGF-β receptor inh V, TGF-β receptor inh I, TGF-β receptor inh IV, TGF-β receptor inh VII, TGF-β receptor inh VIII, TGF-β receptor inh II, TGF-β receptor inh VI, TGF-β receptor inh III, TGF-β inhibitor SB431542, SD-208, ITD-1, LY2109761, A83-01, LY2157299, ALK5i and ALK5 inhibitor II; (b) a thyroid hormone selected from the group consisting of T3, T4, analogues thereof and mixtures thereof; (c) heparin; (d) zinc sulfate; (e) an antioxidant selected from the group consisting of vitamin E, vitamin C, acetyl cysteine, Antioxidant Supplement A1345, glutathione, peroxide dismutase, catalase, and combinations thereof; and (f) one or more of an aurora kinase inhibitor that is preferably aurora kinase inhibitor II, an RSK inhibitor that is preferably RSK inhibitor II, and an inhibitor of protein methyltransferase DOT1L that is preferably EPZ-5676 and culturing, preferably at the air-liquid interface, for about seven to twenty-one days, preferably for about seven to ten days, more preferably about seven days to differentiate the Stage 6 cells into Stage 7 Cells. In one embodiment, the growth medium is supplemented with T3, T4, analogues thereof and mixtures thereof, an ALK5 inhibitor, an antioxidant and an aurora kinase inhibitor, preferably aurora kinase inhibitor II or an RSK inhibitor, preferably RSK inhibitor II. The Stage 6 cells may be differentiated into Stage 7 cells by treatment with a medium supplemented with about 10000 nM of ALK5 inhibitor II, about 1000 nM of T3, about 10 µM of 6-hydroxy-2,5,7,8-tetramethyl chroman-2-carboxyluic acid ("Trolox"), and about 1 µM to about 1 µM of aurora kinase inhibitor II or RSK inhibitor II for about seven days.

In one embodiment, the Stage 6 cells may be differentiated into Stage 7 cells by treatment with a medium supplemented with about 10000 nM of ALK5 inhibitor, about 1 µM of T3, about 2 µM of one or more of aurora kinase inhibitor II, RSK inhibitor II, and a EPZ-5676, and about 1 mM N-acetyl cysteine. Alternatively, one or more of about 0.25 µM SANT-1, about 50 nM RA, about 0.25 mM ascorbic acid, and about 100 nM LDN-193189 also may be added.

Alternatively, Stage 6 cells may be differentiated into Stage 7 cells by treatment with a medium supplemented with heparin, T3, T4, analogues thereof or mixtures thereof, an ALK5 inhibitor, an antioxidant, and an aurora kinase inhibitor, an RSK inhibitor, a protein methyl transferase inhibitor of DOT1L or mixtures thereof and culturing, preferably at the air-liquid interface, for about seven to twenty-one days, alternatively about seven to ten days, preferably about seven days. In an alternate embodiment, the medium may be supplemented with one or more of retinoic acid, an SMO inhibitor, an SHH signaling pathway antagonist, a BMP receptor inhibitor, and N-acetyl cysteine.

In a preferred embodiment, the ALK5 inhibitor is ALK5 inhibitor II. In a more preferred embodiment, about 10000 nM of ALK5 inhibitor II is used. Accordingly, in one embodiment, Stage 6 cells may be differentiated into Stage 7 cells by treatment with a medium supplemented with heparin, T3, T4, analogues thereof and mixtures thereof, and an ALK5 inhibitor, an antioxidant, and an aurora kinase inhibitor, an RSK inhibitor or an inhibitor of protein methyltransferase DOT1L and culturing, preferably at the air-liquid interface, for about seven days. In certain embodiments, the cells may be treated with a cell detachment solution, such as a solution containing proteolytic and collagenolytic enzymes prior to culturing at the air-liquid interface. In a particularly preferred embodiment of the invention, one or more of an aurora kinase inhibitor, preferably aurora kinase inhibitor II, an RSK inhibitor, preferably RSK inhibitor II, and an inhibitor of protein methyltransferase DOT1L, preferably EPZ-5676 are added to the medium. The amount added may be from about 100 to 5000 nM, alternatively about 1000 to 5000 nM, alternatively about 2000 to 5000 nM, alternatively about 3000 to 5000 nM, and preferably about 1000 nM to 2000 nM aurora kinase inhibitor, more preferably about 2000 nM aurora kinase or RSK inhibitor or about 100 to 500 nM DOT1L inhibitor, and more preferably about 1 µM to about 10 nM of DOT1L inhibitor.

In accordance with the foregoing method, the invention further provides a cell culture for differentiating cells expressing markers characteristic of pancreatic endoderm/endocrine precursor cells into cells expressing markers characteristic of mature pancreatic endocrine cells, comprising: (a) a culture vessel; (b) a volume of growth medium within said vessel sufficient to fill only a portion of the volume of said vessel; (c) air within said vessel that fills a portion of said vessel adjoining said medium; (d) a porous substrate located at the interface between said medium and said air; and (d) cells expressing markers characteristic of pancreatic endoderm/endocrine precursor cells derived from pluripotent stem cells disposed upon the surface of said substrate such that said medium contacts only a portion of the surface of said cells.

In one embodiment, Stage 6 cells cultured according to embodiments of the invention are utilized and differentiated into Stage 7 cells, while in other embodiments Stage 6 cells cultured according to other protocols may be utilized.

In another embodiment, the methods of the invention result in the formation of Stage 7 cells that are single-hormone positive. Thus, in one embodiment, the methods of the invention result in Stage 7 cells, which co-express NKX6.1, insulin, PDX1, and MAFA. In another embodiment, the methods of the invention result in Stage 7 cells, which co-express NKX6.1, PDX1, insulin and MAFA. In still another embodiment, a population of cells in which each of the cells of at least about 10%, alternatively at least about 20%, alternatively at least about 30%, alternatively at least about 40%, alternatively at least about 50%, alternatively at least about 60%, alternatively at least about 70%, alternatively at least about 80%, or alternatively at least about 90% of the cell population express insulin, PDX1. NKX6.1, and MAFA result.

In certain and preferred embodiments of the invention, the method employs BLAR a custom medium (Table I) at Stages 4 through 7 or late Stage 4 through 7, or Stages 5, 6 and 7. The medium may preferably be exchanged every day or alternatively every other day.

In another embodiment, the invention relates to a method of forming Stage 7 cells co-expressing NKX6.1, PDX1, MAFA and insulin comprising culturing Stage 4, preferably late Stage 4 cells to Stage 7 cells at the air-liquid interface. In yet another embodiment, the invention relates to a method of forming single hormone insulin positive cells expressing NKX6.1, PDX1, and MAFA Stage 7 cells by culturing Stage 4, preferably late Stage 4 cells, to Stage 7 cells at the air-liquid interface.

Stage 6 and 7 cells generated according to the methods described herein are also well-suited for use in screening compounds for their effect on the secretion of pancreatic hormones and endocrine markers. In particular, Stage 4 through Stage 7 cells cultured at ALI can be tested in different culture formats from 384 to 6-well formats. Such formats allow for evaluation of a variety of small molecules or biologics at various doses and time intervals on subsequent expression of pancreatic endoderm, pancreatic endocrine precursor, pancreatic endocrine, and pancreatic beta cell markers. Such an evaluation may be accomplished by measuring gene expression by PCR, protein expression by FACS or immune staining, or by ELISA for secretion of factors by cells affected by addition of small molecules/biologics.

Cells Obtainable by the Methods of the Invention.

The invention provides a cell, or population of cells obtainable by a method of the invention. The invention also provides a cell, or cell population, preferably expressing markers characteristics of pancreatic endocrine cells of a mature phenotype. The invention also provides an insulin positive cell or population of insulin positive cells, preferably expressing markers characteristic of pancreatic endocrine cells of a mature phenotype, characterized by NKX6.1 expression (preferably greater than about 30%), PDX1 expression (preferably greater than about 30%), and MAFA expression (preferably greater than about 10%).

Methods for Treatment.

The invention provides methods of treatment and in particular for treating patients suffering from, or at risk of developing, diabetes. The invention also provides a population of cells obtainable or obtained by a method of the invention for use in a method of treatment. In particular the invention provides a cell or population of cells obtainable or obtained by a method of the invention for use in a method of treating a person suffering from, or at risk, of developing diabetes. The diabetes may be Type 1 or Type 2.

In one embodiment, the method of treatment comprises implanting cells obtained or obtainable by a method of the invention into a patient. In one embodiment, the method of treatment comprises differentiating pluripotent cells in vitro into Stage 1, Stage 2, Stage 3, Stage 4, Stage 5, Stage 6 or Stage 7 cells, for example as described herein, and implanting the differentiated cells into a patient. In another embodiment, the method further comprises the step of culturing pluripotent stem cells, for example as described herein, prior to the step of differentiating the pluripotent stem cells. In a still further embodiment, the method further comprises the step of differentiating the cells in vivo after the step of implantation. In one embodiment, the patient being treated by any of the methods is a mammal and preferably is a human.

In one embodiment, the cells may be implanted as dispersed cells or formed into clusters that may be infused into the vascular system, for example, the hepatic portal vein. Alternatively, the cells may be provided in a biocompatible, degradable, polymeric support, porous, non-degradable devices, or encapsulated to protect from the immune system of the host. In one embodiment, the method of treatment further comprises incorporating cells into a three-dimensional support prior to implantation. The cells can be maintained in vitro on this support prior to implantation into the patient. Alternatively, the support containing the cells can be directly implanted in the patient without additional in vitro culturing. The support can optionally be incorporated with at least one pharmaceutical agent that facilitates the survival and function of the transplanted cells. Cells may be implanted into an appropriate site in a recipient including, for example, the liver, natural pancreas, renal subscapular space, omentum, peritoneum, subserosal space, intestine, stomach, or a subcutaneous pocket.

To enhance further differentiation, survival or activity of the implanted cell in vivo, additional factors, such as growth factors, antioxidants, or anti-inflammatory agents may be administered before, simultaneously with, or after administration of the cells. These factors can be secreted by endogenous cells and exposed to the administered cells in situ. Implanted cells can be induced to differentiate by any combination of endogenous and exogenously administered growth factors known in the art.

The amount of cells used in implantation depends on a number of factors including the condition of the implantation subject and response to the implanted therapy and can be determined by one skilled in the art.

The invention will be further clarified by a consideration of the following, non-limiting examples.

EXAMPLES

Example 1

Pancreatic Endoderm Cells Cultured at the Air-Liquid Interface—Progressive Increase in Expression of MAFA from Stage 5 to Stage 7

This example demonstrates the kinetics of MAFA expression in pancreatic endoderm cells cultured at an air-liquid interface ("ALI") during Stages 5 through 7 and treated from Stage 5 to Stage 7 with T3 and ALK5 inhibitor II. Cells of the human embryonic stem cell line H1 (WA01 cells, WiCell Research Institute, Madison, Wis.) at passage 42 were seeded as single cells at $1\times10^5$ cells/cm$^2$ on MATRIGEL™ at a 1:30 dilution (Corning Incorporated, Corning N.Y., Catalog No. 354230) coated dishes in a media of Dulbecco's Modified Eagle's Medium; Nutrient mixture F-12 ("DMEM-F12") (Life Technologies Corporation, Carlsbad, Calif., Catalog No. 11330-032), GlutaMAX™ (Life Technologies, Catalog No. 35050-079) in a 1:100 dilution ("1× concentration"), 0.25 mM ascorbic acid (Sigma Aldrich Co. LLC, St. Louis Mo., Catalog No. A4544), 100 ng/ml of fibroblast growth factor 2 ("FGF2") (R & D Systems, Minneapolis, Minn., Catalog No. 233-FB-025), 1 ng/ml of transforming growth factor beta ("TGF-β") (R & D Systems Inc., Catalog No. 240-B-002), insulin-transferrin-selenium-ethanolamine ("ITS-X") (Life Technologies, Catalog No. 51500056) at a 1:100 dilution, 2% fatty-acid free bovine serum albumin ("FAF-BSA") (Proliant, Inc., Boone, Idaho, Catalog No. 68700), and 20 ng/ml of insulin-like growth factor-1 ("IGF-1") (R & D Systems, Catalog No. 291-G1-200), supplemented with 10 μM of Rock inhibitor Y-27632 (Catalog No. Y0503, Sigma-Aldrich). Forty-eight hours post-seeding, the cultures were washed in incomplete PBS (phosphate buffered saline without magnesium or calcium) followed by incubation with 1× TrypLE™ Express Enzyme (Life Science; Catalog No. 14190) for 3 to 5 minutes at 37° C. The released cells were rinsed with DMEM-F12 and spun at 1000 rpm for 5 minutes. The resulting cell pellet was resuspended in DMEM-F12 supplemented with 10 μM Y-27632, GlutaMAX™ in a 1:100 dilution ("1× concentration"), 0.25 mM ascorbic acid, 100 ng/ml FGF2, 1 ng/ml TGF-β, ITS-X at a 1:100 dilution, 2% FAF-BSA and 20 ng/ml IGF-1 and the single cell suspension was seeded at approximately 1.3 to $1.5\times10^5$ cells/cm$^2$. The cultures were fed every day with medium and differentiation, according to the following protocol, was initiated 48 hrs. following seeding resulting in an about 90% starting confluency. During Stages 1 through 4 of the differentiation protocol used, cultures were maintained on planar adherent cultures and at the air-liquid interface for Stages 5 through 7.

Stage 1 (3 Days):

Cells were plated on MATRIGEL™ (1:30 dilution)-coated dishes were first rinsed with 1× incomplete DPBS and then were cultured for one day in the following Stage 1 media: MCDB-131 medium (Life Technologies, Catalog No. 10372-019) supplemented with 0.5% FAF-BSA, 1.2 g/1000 ml sodium bicarbonate (Sigma-Aldrich Catalog No. S3187); GlutaMAX™ at a concentration of 1×; 4.5 mM D-glucose (Sigma-Aldrich, Catalog No. G8769) in this stage and the following stages where used, to obtain a concentration of 10 mM of glucose (Sigma-Aldrich, Catalog No. G8769); 100 ng/ml growth/differentiation factor 8 ("GDF8") (Peprotech, Rocky Hill, N.J. Catalog No. 120-00); and 1 μM of a 14-Prop-2-en-1-yl-3,5,7,14,17,23,27-heptaazatetracyclo[19.3.1.1~2,6~.1~8,12~]heptacosa-1(25),2(27),3,5,8(26),9,11,21,23-nonaen-16-one ("MCX compound"). Cells were then cultured for an additional day in MCDB-131 medium supplemented with 0.5% FAF-BSA, 0.0012 g/ml sodium bicarbonate, 1× concentration of GlutaMAX™, 4.5 mM D-glucose, 100 ng/ml GDF8, and 0.1 μM MCX compound. Cells were then cultured for an additional day in MCDB-131 medium supplemented with 0.5% fatty acid-free BSA, 1.2 g/1000 ml sodium bicarbonate, 1× GlutaMAX™, 4.5 mM D-glucose, and 100 ng/ml GDF8.

Stage 2 (2 Days):

Cells were first rinsed with 1× incomplete DPBS and then were treated for two days with MCDB-131 medium supplemented with 0.5% FAF-BSA; 1.2 g/1000 ml sodium bicarbonate; 1× GlutaMAX™; 4.5 mM D-glucose; 0.25 mM ascorbic acid and 25 ng/ml FGF7 (R & D Systems, Inc., Catalog No. 251-KG.).

Stage 3 (2 Days):

Cells were treated with BLAR custom medium (manufactured by Life Technologies, components listed on Table I) supplemented with a 1:200 dilution of ITS-X; 4.5 mM glucose; 1× GlutaMAX™; 2.5 g/1000 ml sodium bicarbonate; 2% FAF-BSA; 0.25 µM SANT-1 (N-[(3,5-dimethyl-1-phenyl-1H-pyrazol-4-yl)methylene]-4-(phenylmethyl)-1-piperazineamine) (Sigma Aldrich, Catalog No. S4572); 1 µM retinoic acid ("RA") (Sigma Aldrich, Catalog No. R2625); 25 ng/ml FGF7; 0.25 mM ascorbic acid; 200 nM the PKC activator ((2S,5S-(E,E)-8-(5-(4-trifluoromethyl)phenyl-2,4,-pentadienoylamino)benzolactam ("TPB") (EMD Millipore Corporation, Gibbstown, N.J.; Catalog No. 565740); and 100 nM of the bone morphogenic protein ("BMP") receptor inhibitor LDN-193189 (Shanghai ChemPartners Co Ltd., Shanghai, China) for two days.

Stage 4 (3 Days):

Cells were treated with BLAR medium supplemented with a 1:200 dilution of ITS-X; 4.5 mM glucose; 1× concentration of GlutaMAX™; 2.5 g/1000 ml sodium bicarbonate; 2% FAF-BSA; 0.25 µM SANT-1; 100 nM RA; 2 ng/ml FGF7; 100 nM LDN-193189; 0.25 mM ascorbic acid; and 200 nM TPB for three days. At end of Stage 4 (3 days), cells cultured on planar dishes were treated for 4 hours with 10 µM of Y27632, rinsed with PBS and treated for 5 minutes at room temperature with the enzyme TrypLE™ Express Enzyme (LifeTechnologies Corporation, Catalog No. 12604-013) at a concentration of 1× followed by removal of the enzyme, rinsing with BLAR media and scraping of cells by a cell scraper. The resulting suspension of cells were seeded at a density of 0.5-0.75×$10^6$ cells (in 5-10 µl aliquots) on 0.4 micron porous cell culture filter inserts (Corning, Catalog No. 353493) in 6-well plates. 1.5 ml of media was added to the bottom of each insert and no further media was added to the apical, or top, side of the filter. The media was replaced daily for the duration of Stages 5, 6 and 7.

Stage 5 (3 Days):

Cells cultured at the air-liquid interface were treated with BLAR medium supplemented with a 1:200 dilution of ITS-X; glucose to achieve a final concentration of 20 mM glucose; 1× GlutaMAX™; 1.5 g/1000 ml sodium bicarbonate; 2% FAF-BSA; 0.25 mM ascorbic acid; 10 µg/ml of heparin (Sigma Aldrich, Catalog No. H3149), 10 µM $ZnSO_4$ (Sigma Aldrich, Catalog No. Z0251), 0.25 µM SANT-1; 50 nM RA; 100 nM LDN-193189; 1 µM of T3 in the form of 3,3',5-triiodo-L-thyronine sodium salt (Sigma Aldrich, Catalog No. T6397), 10000 nM of 2-(3-(6-Methylpyridin-2-yl)-1H-pyrazol-4-yl)-1,5-naphthyridine ("ALK5 inhibitor II") (Enzo Life Sciences, Inc., Farmingdale, N.Y., Catalog No. ALX-270-445) for three days.

Stage 6 (7 Days):

Stage 5 cells were treated with BLAR medium supplemented with a 1:200 dilution of ITS-X; glucose to achieve a final concentration 20 mM Glucose; 1× concentration of GlutaMAX™; 1.5 g/1000 ml sodium bicarbonate; 2% FAF-BSA; 0.25 mM ascorbic acid; 10 µg/ml of heparin, 10 µM $ZnSO_4$, 100 nM LDN-193189, 1 µM T3, 100 nM (S,S)-2-[2-(3,5-Difluorophenyl)acetylamino]-N-(5-methyl-6-oxo-6,7-dihydro-5H-dibenzo[b,d]azepin-7-yl)propionamide ("gamma secretase inhibitor XX") (EMD Millipore, Catalog No. #565789), and 10000 nM ALK5 inhibitor II for 7 days.

Stage 7 (7 Days):

Stage 6 cells were treated with BLAR medium supplemented with a 1:200 dilution of ITS-X; glucose to achieve a final concentration 20 mM Glucose, 1× GlutaMAX™; 1.5 g/1000 ml sodium bicarbonate; 2% FAF-BSA; 10 µg/ml of heparin, 10 µM $ZnSO_4$, 1 µM T3, 10000 nM ALK5 inhibitor II, 10 µM the vitamin E analogue Trolox (EMD Millipore Catalog No. 648471) for 7-15 days.

FIGS. 1A, 1B, 1C, 1D, 1E, 1F, 1G, 1H, 1I, 1J, 1K, 1L, and 1M depict data from real-time PCR analyses of the following genes in cells of the human embryonic stem cell line H1 differentiated as outlined in Example 1: PDX1 (FIG. 1A); NKX6.1 (FIG. 1B); PAX4 (FIG. 1C); PAX6 (FIG. 1D); NGN3 (FIG. 1E); MAFA (FIG. 1F); ABCC8 (FIG. 1G); chromogranin-A (FIG. 1H); G6PC2 (FIG. 1I); IAPP (FIG. 1J); insulin (FIG. 1K); glucagon (FIG. 1L); and PTF1a (FIG. 1M). As shown in FIG. 1F, there was a clear increase, or upregulation, in MAFA comparing Stages 4 and 5 to Stages 6 and 7 demonstrating an increased maturation of cells towards a beta cell lineage. However, at Stages 6 and 7, the mRNA expression for MAFA was lower than adult human islets.

TABLE I

List of components of BLAR media

| Component | Concentration (mM) |
| --- | --- |
| Amino Acids | |
| Glycine | 3.0E-02 |
| Alanine | 3.0E-02 |
| Arginine | 3.0E-01 |
| Aspargine | 1.0E-01 |
| Aspartic Acid | 1.0E-01 |
| Cysteine | 2.0E-01 |
| Glutamic acid | 3.0E-02 |
| Histidine | 1.1E-01 |
| Isoleucine | 1.0E-02 |
| Leucine | 9.0E-02 |
| Lysine hydrochloride | 1.5E-01 |
| Methiane | 3.0E-02 |
| Phenylalanine | 3.0E-02 |
| Proline | 1.0E-01 |
| Serine | 1.0E-01 |
| Theronine | 3.0E-02 |
| Tryptophan | 2.0E-03 |
| Tyrosinedisodium | 1.0E-02 |
| Valine | 3.0E-02 |
| Vitamins | |
| Biotin | 3.0E-05 |
| Choline chloride | 5.0E-03 |
| D-Calcium pantothenate | 1.5E-03 |
| Folinic Acid Calcium salt | 2.3E-03 |
| Niacinamide | 4.9E-03 |
| Pyridoxine hydrochloride | 9.7E-04 |
| Riboflavin | 1.0E-05 |
| Thiamine hydrochloride | 3.0E-03 |
| Vitamin B12 | 3.7E-06 |
| i-Inositol | 2.8E-03 |
| Minerals/other | |
| Calcium Chloride ($CaCl_2$—2$H_2O$) | 3.0E-01 |
| Cupric sulfate ($CuSO_4$—5H2O) | 4.8E-06 |
| Ferric sulfate ($FeSO_4$—7$H_2O$) | 1.0E-03 |
| Magnesium Sulfate (MgSO4—7$H_2O$) | 4.1E-01 |
| Potassium Chloride (KCl) | 3.8E+00 |
| Sodium Bicarbonate ($NaHCO_3$) | 1.4E+01 |
| Sodium Chloride (NaCl) | 1.1E+02 |
| Sodium Phosphate dibasic (Na2HPO4—7$H_2O$) | 5.0E-01 |
| Zinc Sulfate ($ZnSO_4$—$H_2O$) | 1.0E-04 |
| Adenine | 1.0E-03 |

TABLE I-continued

List of components of BLAR media

| Component | Concentration (mM) |
|---|---|
| D-Glucose (Dextrose) | 5.0E+00 |
| Lipoic Acid | 1.2E+05 |
| Phenol Red | 1.0E−02 |
| Sodium Pyruvate | 1.0E+00 |
| Thymidine | 9.8E−05 |

For additional characterization of various stages, cells were harvested at Stages 3, 4, 5, 6, and 7 and analyzed by fluorescence-activated flow cytometry ("FACS"). FACS staining was conducted as described in *Diabetes*, 61, 2016, 2012 and using the antibodies listed in Table III. In brief, cells were incubated in TrypLE™ Express (Life Technologies, Catalog No. 12604) for 3-5 minutes at 37° C. and released into single cell suspensions after which they were washed twice with a staining buffer of PBS containing 0.2% BSA (BD Sciences, Catalog No. 554657). Cells ($1\times10^5$ to $1\times10^6$) were re-suspended in 100 µl blocking buffer of 0.5% human gamma globulin diluted 1:4 in staining buffer for surface marking. Added to the cells at a final dilution of 1:20 were directly conjugated primary antibodies followed by incubation at 4° C. for 30 minutes. The stained cells were twice washed in the staining buffer, followed by re-suspension in 200 µl staining buffer and then incubated in 15 µl of 7AAD for live/dead discrimination before FACS analysis on the BD Canto II. Intracellular antibody staining was accomplished by first incubating with Green Fluorescent LIVE/DEAD cell dye (Life Technologies, Catalog No. L23101) at 4° C. for 20 minutes followed by a single wash in cold PBS. Fixing of cells was in 250 µl of Cytofix/Cytoperm Buffer (BD Catalog No. 554723) followed by re-suspension of the cells in 100 µl of Perm wash buffer staining/blocking solution with 2% normal goat serum. Cells were incubated at 4° C. for 30 minutes with primary antibodies at empirically pre-determined dilutions followed by two washes in Perm/Wash buffer. Cells were then incubated with the appropriate antibodies at 4° C. for 30 minutes and then washed twice prior to analysis on a BD FACS Canto II. The concentrations of antibodies used are shown on Table III. The antibodies for pancreas markers were tested for specificity using human islets or undifferentiated H1 cells as a positive control. For secondary antibodies, the following were added and incubated at 4° C. for 30 minutes: anti-mouse Alexa Fluor® 647 at 1:500 (Life Technologies), goat anti-rabbit PE at 1:200 (v) or donkey anti-goat Alexa 647 at 1:800 (Life Technologies) followed by a final wash in Perm/Wash buffer and analysis on a BD FACS Canto II using BD FACS Diva Software with at least 30,000 events being acquired.

Figure 7:
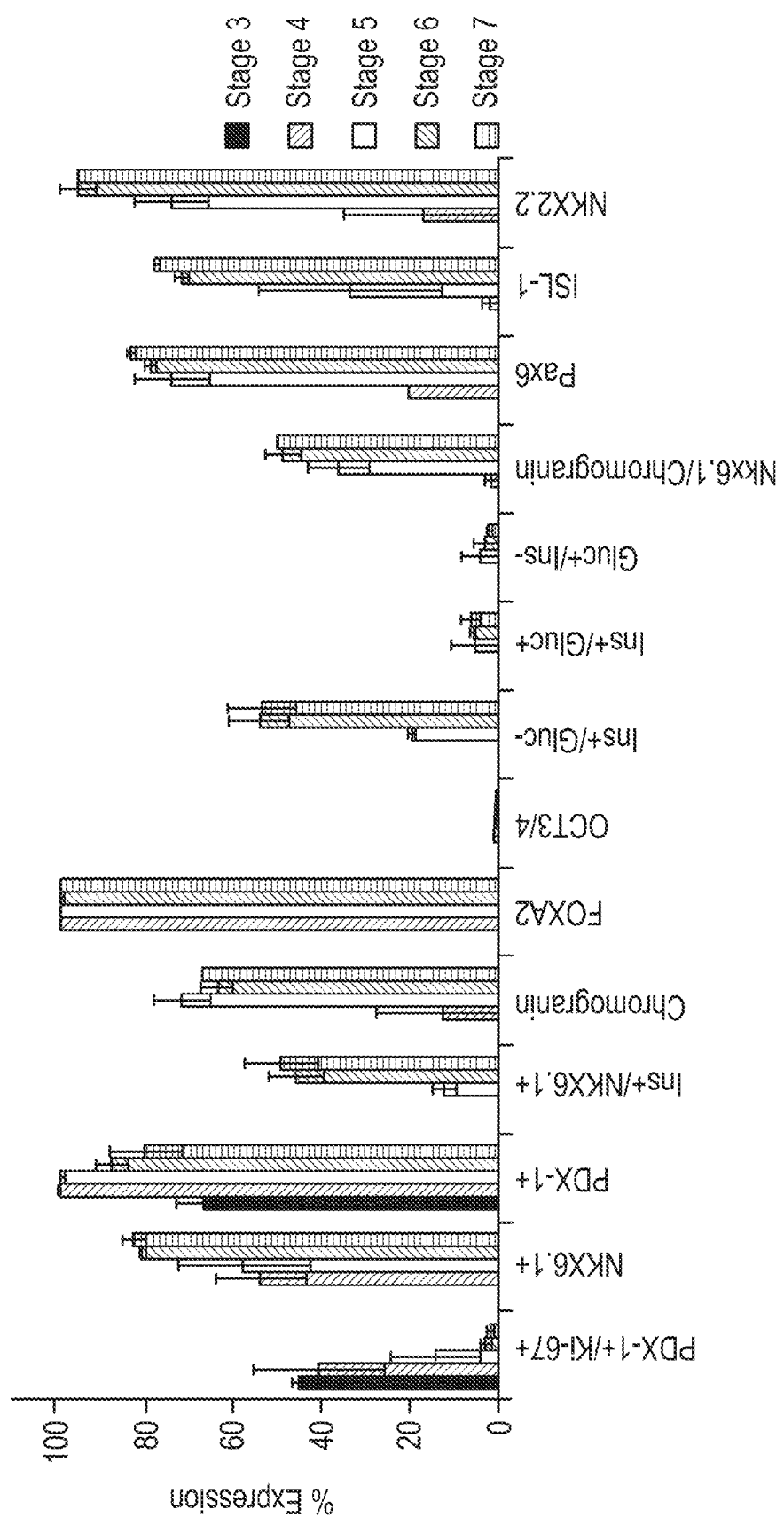
FIG. 7 is a graph of the percent expression of multiple pancreatic endoderm markers (FOXA2, PDX1, NKX6.1), an undifferentiated ES cell marker (Oct3/4), endocrine markers (PAX6, IS1-1, NKX2.2, chromogranin), and hormone (insulin, glucagon) from Stage 3 through Stage 7 cells differentiated according to Example 1.
Figure 8E:
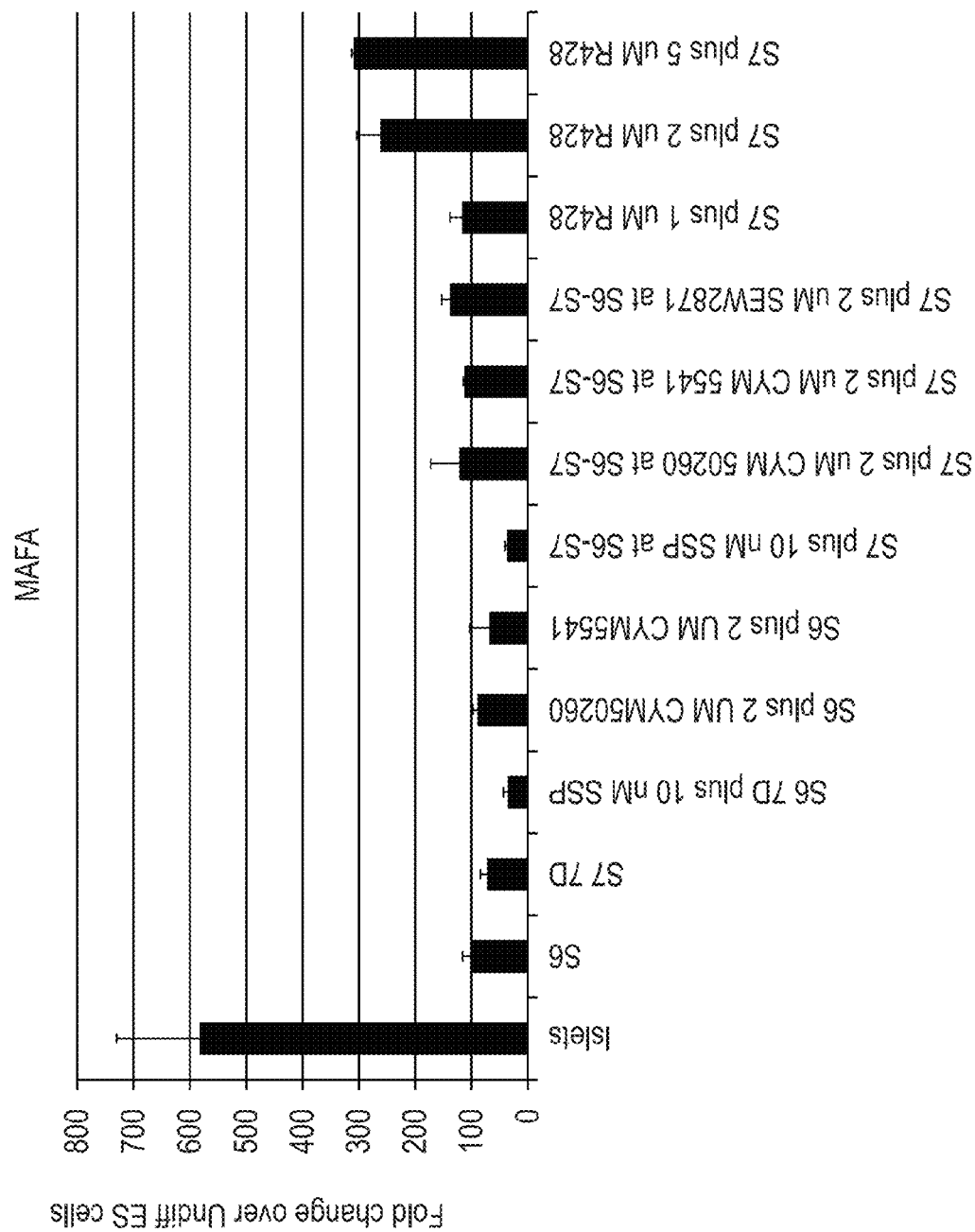
FIGS. 8A, 8B. 8C, 8D and 8E are graphs depicting data from real-time PCR analyses of the fold change of expression of insulin and MAFA of differentiated cells over undifferentiated cells after treatment with small molecules in Stage 6-7.
Figure 11A:
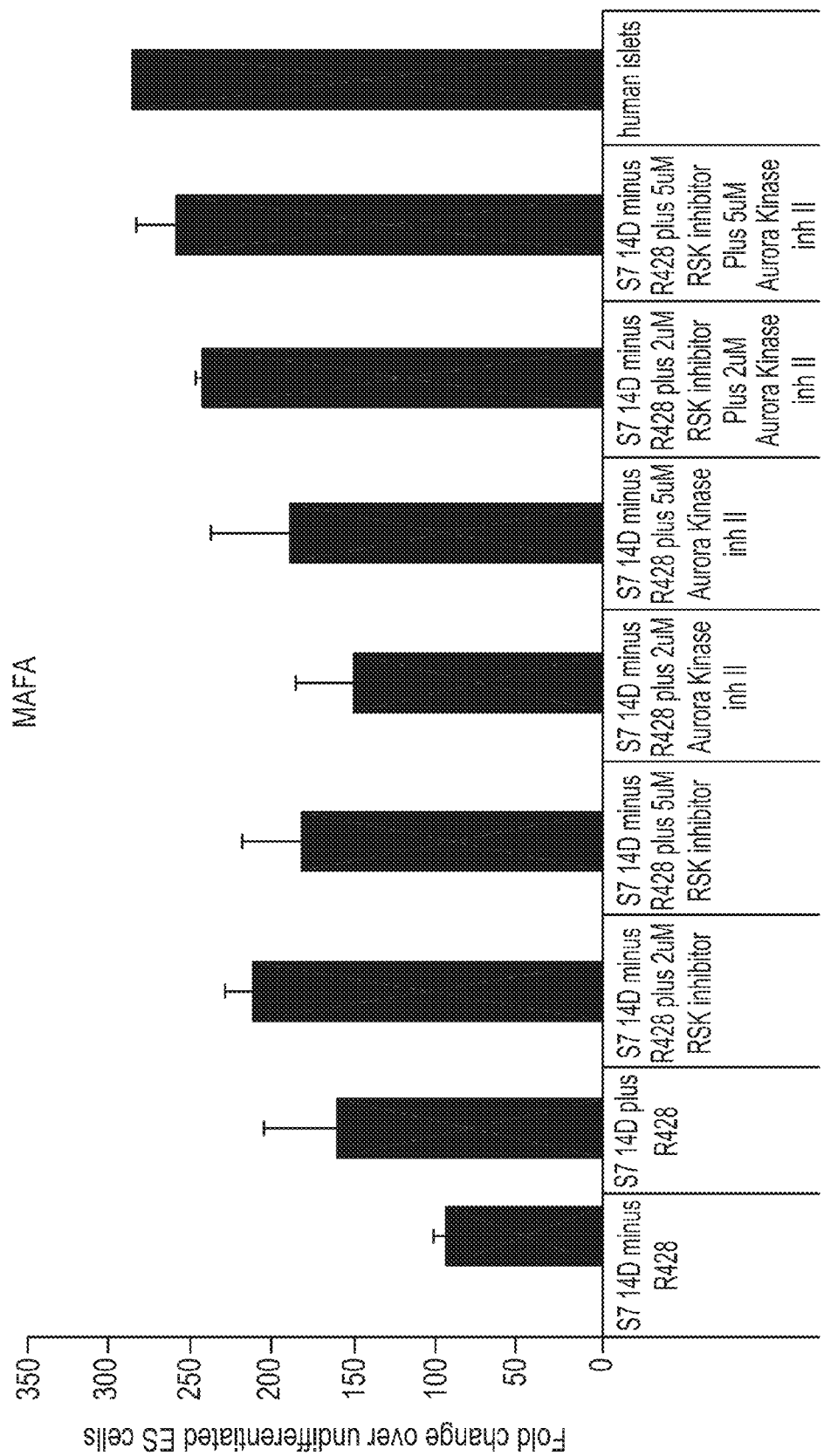
Figure 11C:
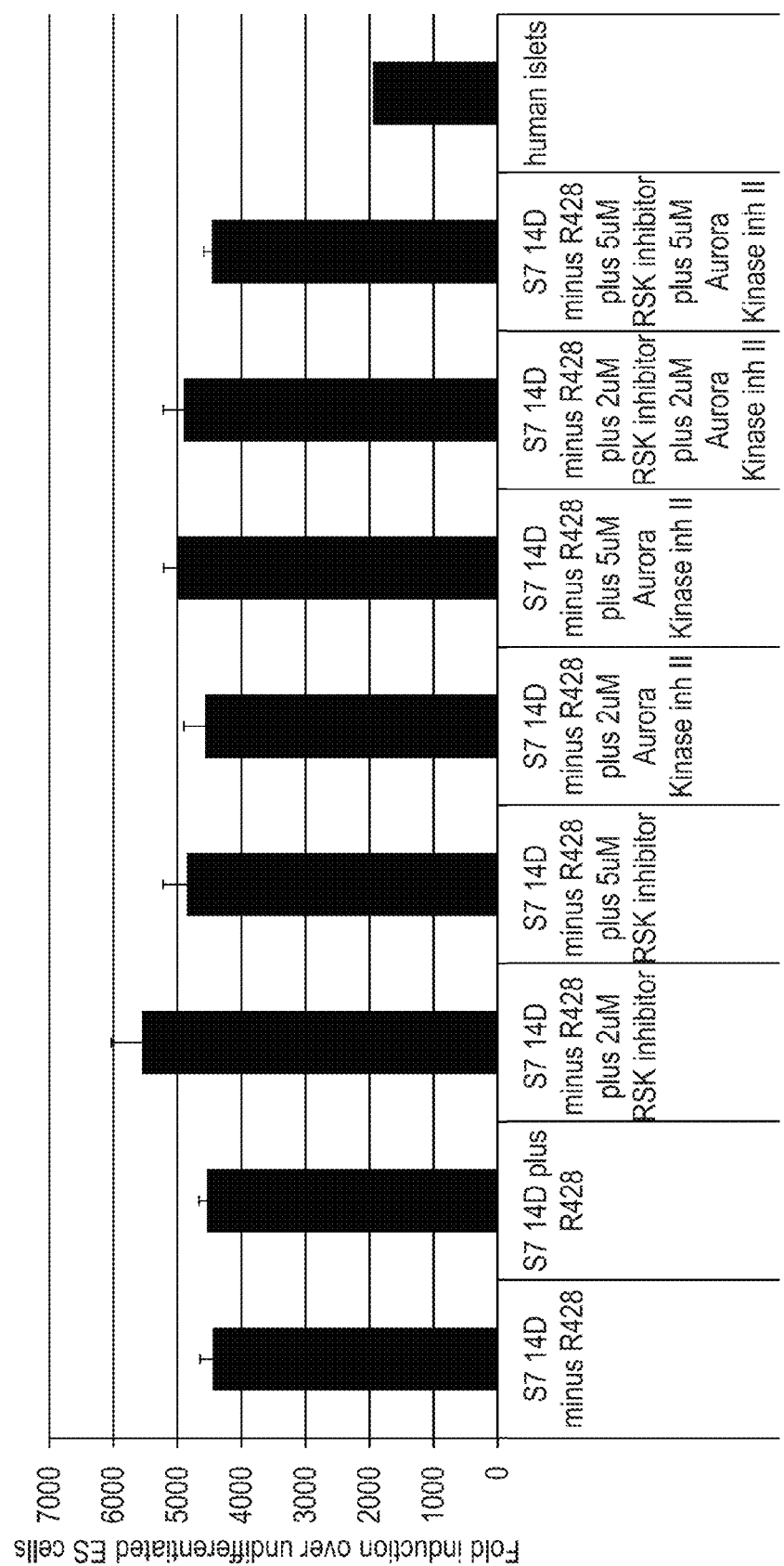

FIGS. 2A, 2B, 2C, 3A, 3B, 3C, 3D, 4A, 4B, 4C, 4D, 4E, 5A, 5B, 5C, 5D, 5E, 5F, 6A, 6B, 6C, 6D, 6E and 6F depict FACS profiles of cells collected at Stages 3, 4, 5, 6, and 7, respectively. As shown in FIGS. 4A, 4B, 4C, 4D and 4E, at Stage 5, approximately 15% of cells were co-expressing insulin and NKX6.1 and approximately 21% of PDX1 positive cells were in active cell cycle as measured by co-expression of PDX1 and KI-67 (~23%; KI-67 is indicative of cells that are in active cell cycle). However, by Stage 6 and Stage 7 (FIGS. 5A, 5B, 5C, 5D, 5E, 5F, 6A, 6B, 6C, 6D, 6E and 6F), there was a significant drop in proliferating PDX1+ cells (1-2%) while there was a significant increase in the number of NKX6.1+ cells co-expressing insulin (~39% at Stage 6 and ~50% at Stage 7). Moreover, there was a significant rise in cells expressing endocrine precursor markers ISL-1, NeuroD1, and NKX2.2. These results indicate that the cultures of Stages 6 and 7 allowed for rapid maturation of cells away from a proliferating progenitor fate to early maturing endocrine cells. In addition, an increase in the percentage of cells co-expressing insulin and NXK6.1 (33%) was observed by prolonging going from Stage 6 to Stage 7 (FIGS. 5A, 5B, 5C, 5D, 5E, 5F as compared to FIGS. 6A, 6B, 6C, 6D, 6E and 6F). FIG. 7 summarizes the percent expression of multiple pancreatic endoderm (FOXA2, PDX-1, NKX6.1), undifferentiated ES cells (Oct3/4), endocrine (Pax6, IS1-1, NKX2.2, chromogranin), and hormone (insulin, glucagon) from Stage 3 through Stage 7.

TABLE II

List of Antibodies used for FACS analysis

| Antigen | Species | Source/Catalogue Number | Dilution |
|---|---|---|---|
| Glucagon | Mouse | Sigma-Aldrich Co. LLC/G2654 | 1:250 |
| Insulin | Rabbit | Cell Signaling Technology. Inc., Danvers. MA/3014B | 1:10 |
| NKX6.1 | Mouse | Developmental Studies Hybridoma Bank. Iowa City, Iowa/F55A12 | 1:50 |
| NKX2.2 | Mouse | Developmental Studies Hybridoma Bank/74.5A5 | 1:100 |
| PDX1 | Mouse | BD BioSciences, San Jose, CA/562161 | 1:50 |
| Ki67 | Mouse | BD Biosciences/558595 | 1:20 |
| Pax6 | Mouse | BD Biosciences, 561552 | 1:20 |
| Chromogranin A | Rabbit | Dako, Carpinteria, CA/A0430 | 1:40 |
| ISL-1 | Mouse | BD Biosciences/562547 | 1:20 |
| NeuroD1 | Mouse | BD Bioscience/563001 | 1:40 |
| FOXA2 | Mouse | BD Bioscience/561589 | 1:80 |
| OCT3/4 | Mouse | BD Biosciences/560329 | 1:20 |

Example 2

Screening to Identify Small Molecules that can Significantly Upregulate One or Both of MAFA and Insulin Expression This example is directed to identify small molecules that can significantly enhance maturation of cells towards a pancreatic beta cell. Cells of the human embryonic stem cell line H1 (WA01) at passage 42 were seeded as single cells at $1\times10^5$ cells/cm² on MATRIGEL™ (1:30 dilution)-coated dishes in a media comprising of DMEM-F12, GlutaMAX™ (1:100 dilution), 0.25 mM ascorbic acid, 100 ng/ml of FGF2 (R & D systems, MN), 1 ng/ml of TGF-β, ITS-X (1:100 dilution), 2% FAF-BSA, and 20 ng/ml of IGF-1, supplemented with 10 µM of Y-27632. Forty-eight hours post-seeding, the cultures were washed in incomplete PBS (phosphate buffered saline without Mg or Ca) followed by incubation with 1× TrypLE™ Express Enzyme (Life Science; Catalog No. 14190) for 3 to 5 minutes at 37° C. The released cells were rinsed with DMEM-F12 and spun at 1000 rpm for 5 minutes. The resulting cell pellet was resuspended in DMEM-F12 supplemented with 10 µM Y-27632, 1× GlutaMAX™, 0.25 mM ascorbic acid, 100 ng/ml FGF2, 1 ng/ml TGF-β, ITS-X at a 1:100 dilution, 2% FAF-BSA and 20 ng/ml of IGF-1 and the single cell suspension was seeded at approximately 1.3 to $1.5\times10^5$ cells/cm². The cultures were fed every day with medium and differentiation, according to the following protocol, was initiated 48 hrs. following seeding resulting in an about 90% starting confluency. Unless otherwise stated, the sources for the media, reagents, molecules and the like used in the examples are as stated in Example 1.

Stage 1 (3 Days):

Cells were plated on MATRIGEL™ (1:30 dilution)-coated dishes were first rinsed with 1× incomplete DPBS and then were cultured for one day in Stage 1 media: MCDB-131 medium supplemented with 0.5% FAF-BSA, 0.0012 g/ml sodium bicarbonate; 1× concentration of GlutaMAX™; 4.5 mM D-glucose; 100 ng/ml GDF8; and 1 µM MCX compound. Cells were then cultured for an additional day in MCDB-131 medium supplemented with 0.5% FAF-BSA, 0.0012 g/ml sodium bicarbonate, 1× concentration of GlutaMAX™, 4.5 mM D-glucose, 100 ng/ml GDF8, and 0.1 µM MCX compound. Cells were then cultured for an additional day in MCDB-131 medium supplemented with 0.5% FAF-BSA, 0.0012 g/ml sodium bicarbonate, 1× concentration of GlutaMAX™, 4.5 mM D-glucose, and 100 ng/ml GDF8.

Stage 2 (2 Days):

Cells were first rinsed with 1× incomplete DPBS and then were treated for two days with MCDB-131 medium supplemented with 0.5% FAF-BSA; 0.0012 g/ml sodium bicarbonate; 1× concentration of GlutaMAX™; 4.5 mM D-glucose; 0.25 mM ascorbic acid and 25 ng/ml FGF7.

Stage 3 (2 Days):

Cells were treated with BLAR custom medium supplemented with a 1:200 dilution of ITS-X; 4.5 mM glucose; 1× concentration of GlutaMAX™; 0.0025 g/ml sodium bicarbonate; 2% FAF-BSA; 0.25 µM SANT-1; 1 µM RA; 25 ng/ml FGF7; 0.25 mM ascorbic acid; 200 nM TPB; and 100 nM LDN-193189 for two days.

Stage 4 (3 Days):

Cells were treated with BLAR medium supplemented with a 1:200 dilution of ITS-X; 4.5 mM glucose; 1× concentration of GlutaMAX™; 0.0025 g/ml sodium bicarbonate; 2% FAF-BSA; 0.25 µM SANT-1; 100 nM RA; 2 ng/ml FGF7; 100 nM LDN-193189; 0.25 mM ascorbic acid; and 200 nM TPB for three days, then at end of Stage 4 cells cultured on planar dishes were treated for 4 hours with 10 µM of Y-27632, rinsed with PBS and treated for 5 minutes at room temperature with 1× concentration of TrypLE™ followed by removal of the enzyme, rinsing with BLAR basal media and scraping of cells by a cell scraper. The resulting suspension of cells were seeded at a density of $0.5$-$0.75 \times 10^6$ cells (in 5-10 µl aliquots) on 0.4 micron porous cell culture filter inserts in 6-well plates. 1.5 ml of media was added to the bottom of each insert and no further media was added to the apical side of the filter. The media was replaced daily for the duration of Stages 5, 6 and 7.

Stage 5 (3 Days):

Cells cultured at the air-liquid interface were treated with BLAR medium supplemented with a 1:200 dilution of ITS-X; 20 mM glucose; 1× GlutaMAX™; 0.0015 g/ml sodium bicarbonate; 2% FAF-BSA; 0.25 mM ascorbic acid; 10 µg/ml of heparin, 10 µM $ZnSO_4$, 0.25 µM SANT-1; 50 nM RA; 100 nM LDN-193189; 1 µM of T3 as 3,3',5-triiodo-L-thyronine sodium salt, and 10000 nM of ALK5 inhibitor II for three days.

Stage 6 (7 Days):

Stage 5 cells were cultured at the air-liquid interface and treated with BLAR medium supplemented with a 1:200 dilution of ITS-X; 20 mM Glucose; 1× concentration of GlutaMAX™; 0.0015 g/ml sodium bicarbonate; 2% FAF-BSA; 0.25 mM ascorbic acid; 10 µg/ml of heparin, 10 µM $ZnSO_4$, 100 nM LDN-193189, 1 µM T3 as 3,3',5-triiodo-L-thyronine sodium salt, 100 nM gamma secretase inhibitor XX, and 10000 nM ALK5 inhibitor II for 7 days.

Stage 7 (7 Days):

Stage 6 cells were cultured at the air-liquid interface and treated with BLAR medium supplemented with a 1:200 dilution of ITS-X; 20 mM Glucose; 1× concentration of GlutaMAX™; 0.0015 g/ml sodium bicarbonate; 2% FAF-BSA; 10 µg/ml of heparin, 10 µM $ZnSO_4$, 1000 nM T3 as 3,3',5-triiodo-L-thyronine sodium salt, 10000 nM ALK5 inhibitor II, 10 µM Trolox for 7 days At Stages 6 or 7, various small molecules were added and their effect was evaluated by real-time PCR. Table III lists the small molecules evaluated and when they were added.

TABLE III

| Small molecules evaluated | | | |
|---|---|---|---|
| Chemical name/CAS #/Molecular formula | Target | Small Molecule Name/Vendor/Catalog No. | Concentration |
| 4-(Acetylamino)-N-(2-aminophenyl)benzamide/112522-64-2/$C_{15}H_{15}N_3O_2$ | histone deacetylase (HDAC) inhibitor | CI-994/Sigma Aldrich Co LLC./EPI109A | 1 µM at S6 |
| (E)-N-hydroxy-3-[4-[[2-(2-methyl-1H-indol-3-yl)ethylamino]methyl]phenyl]prop-2-enamide/404950-80-7/$C_{21}H_{23}N_3O_2$ | inhibitor of both histone deacetylase 1 (HDAC1) activity | Panobinostat (LBH-589)/Sigma Aldrich Co LLC./EPI009B | 1 µM at S6 |
| N-hydroxy-N'-phenyl-octanediamide/149647-78-9/$C_{14}H_{20}N_2O_3$ | inhibitor of histone deacetylase 1 (HDAC1) and 3 (HDAC3) | SAHA/Sigma Aldrich Co LLC./EPI009C | 1 µM at S6 |
| N,N'-Dihydroxyoctanediamide/38937-66-5/$C_8H_{16}N_2O_4$ | Histone deacetylase (HDAC) inhibitor that has been shown to inhibit HDAC1 | SBHA/Sigma Aldrich Co LLC./EPI009D | 1 µM at S6 |
| 6-(1,3-Dioxo-1H,3H-benzo[de]isoquinolin-2-yl)-hexanoic acid hydroxyamide/287383-59-9/$C_{18}H_{18}N_2O_4$ | Inhibitor of histone deacetylase (HDAC) | Scriptaid/Sigma Aldrich Co LLC./EPI009E | 1 µM at S6 |
| [R-(E,E)]-7-[4-(Dimethylamino)phenyl]-N-hydroxy-4,6-dimethyl-7-oxo-2,4-heptadienamide/58880-19-6/$C_{17}H_{22}N_2O_3$ | Inhibitor of histone deacetylase | Trichostatin A/Sigma Aldrich Co LLC./EPI009F | 1 µM at S6 |
| N1-[4-[(2R,4R,6S)-4-[[(4,5-diphenyl-2-oxazolyl)thio]methyl]-6-[4-(hydroxymethyl)phenyl]-1,3-dioxan-2-yl]phenyl]-N8-hydroxy-octanediamide/537049-40-4/$C_{41}H_{43}N_3O_7S$ | Inhibitor of histone deacetylase 6 | Tubacin/Sigma Aldrich Co LLC./EPI009G | 1 µM at S6 |

TABLE III-continued

Small molecules evaluated

| Chemical name/CAS #/Molecular formula | Target | Small Molecule Name/Vendor/Catalog No. | Concentration |
|---|---|---|---|
| 1,4-Dimethoxy-9(10H)-acridinethione/141992-47-4/$C_{15}H_{13}NO_2S$ | Cyclin-dependent kinase (cdk) 4 inhibitor | NSC625987/Tocris Bioscience/2152 | 1 µM at S6 |
| 4-[4,5-Dihydro-5-(4-methoxyphenyl)-3-phenyl-1H-pyrazol-1-yl]benzenesulfonamide/71203-35-5/$C_{22}H_{21}N_3O_3S$ | Inhibitor of Cdc42 GTPase | ML141/Tocris Bioscience/4266 | 1 µM at S6 |
| N-(2-chlorophenyl)-6-(piperidin-4-yl)imidazo[1,2-a]pyridine-3-carboxamide oxalate/1198408-39-7/$C_{21}H_{21}ClN_4O_5$ | Inhibitor of EphB3 receptor tyrosine kinase | LDN211904 (EphB3 inhibitor)/EMD Millipore Corporation, Billerica, MA/428201-5MG | 1 µM at S6 |
| (S)-2-(4-(4-chlorophenyl)-2,3,9-trimethyl-6H-thieno[3,2-f][1,2,4]triazolo[4,3-a][1,4]diazepin-6-yl)acetamide/1446144-04-2/$C_{19}H_{18}ClN_5OS$ | CPIe inhibitor of the bromodomain and extra terminal (BET) family protein BRD4 | CPI203/Xcess Biosciences, Inc., San Diego, CA/M60124-2 | 1 µM at S6 |
| 1-(3,6-dibromo-9H-carbazol-9-yl)-3-(phenylamino)propan-2-ol/301353-96-8/$C_{21}H_{18}Br_2N_2O$ | pro-neurogenic, neuro-protective small molecule | P7C3/Xcess Biosciences, Inc./M60017-2 | 1 µM at S6 |
| 2-(4-benzoylphenoxy)-N-(1-benzylpiperidin-4-yl)acetamide/924416-43-3/$C_{27}H_{28}N_2O_3$ | agonist of adiponectin receptor (AdipoR) | AdipoRon/Xcess Biosciences, Inc./M60152-2s | 1 µM at S6 |
| (S)-2-((S)-2-(3,5-difluorophenyl)-2-hydroxyacetamido)-N-((S)-5-methyl-6-oxo-6,7-dihydro-5H-dibenzo[b,d]azepin-7-yl)propanamide/209984-57-6/$C_{26}H_{23}F_2N_3O_4$ | inhibitor of gamma secretase | LY411575/Xcess Biosciences, Inc./M60078-5s | 1 µM at S6 |
| 2-(4-(tert-butyl)phenyl)1H-benzo[d]imidazole/49671-76-3/$C_{17}H_{18}N_2$ | transcriptional activator of PGC-1α | ZLN005/Xcess Biosciences, Inc./M60142-5s | 1 µM at S6 |
| 2-chloro-4-fluoro-3-methyl-N-(2-(4-methylpiperazin-1-yl)-5-nitrophenyl)benzamide/1422389-91-0/$C_{19}H_{20}ClFN_4O_3$ | antagonist of WDR5-MLL interaction | WDR5-C47/Xcess Biosciences, Inc./M60118-2 | 1 µM at S6 |
| 3-pyridinylmethyl [[4-[[(2-aminophenyl)amino]carbonyl]phenyl]methyl]carbamate/209783-80-2/$C_{21}H_{20}N_4O_3$ | HDAC inhibitor; antiproliferative; Preferentially inhibits HDAC1 over HDAC3 | MS-275/Sigma Aldrich Co LLC./EPS002 | 1 µM at S6 |
| 4-(Dimethylamino)-N-[7-(hydroxyamino)-7-oxoheptyl]-benzamide/251456-60-7/$C_{16}H_{25}N_3O_3$ | HDAC inhibitor; subtype selective for HDAC6 over HDAC1 | M344/Sigma Aldrich Co LLC./M5820 | 1 µM at S6 |
| 1-[[4-Ethyl-5-[5-(4-phenoxyphenyl)-1,2,4-oxadiazol-3-yl]-2-thienyl]methyl]-3-azetidinecarboxylic acid/913827-99-3/$C_{25}H_{23}N_3O_4S$ | Sphingosine-1-phosphate receptor 1 (S1P1) agonist; Exhibits 5000-fold selectivity for human S1P1 over S1P3 | CS2100/Tocris Bioscience, Bristol, BS11 0QL, UK/4543 | 1 µM at S6 |
| 2-(4-Bromo-2-chlorophenoxy)-N-[[[4-[[(4,6-dimethyl-2-pyrimidinyl)amino]sulfonyl]phenyl]amino]thioxomethyl]acetamide/587841-73-4/$C_{21}H_{19}BrClN_5O_4S_2$ | Selective inhibitor of Cdc42 | ZCL278/Tocris Bioscience/4794 | 1 µM at S6 |
| N-(4-(2-amino-3-chloropyridin-4-yloxy)-3-fluorophenyl)-4-ethoxy-1-(4-fluorophenyl)-2-oxo-1,2-dihydropyridine-3-carboxamide/1025720-94-8/$C_{25}H_{19}ClF_2N_4O_4$ | Met-related inhibitor for c-Met, Axl, Ron and Tyro3 | BMS-777607/Selleck Chemicals, Houston, TX/S1561 | 1 µM at S6 |
| N-(2,6-difluorophenyl)-5-(3-(2-(5-ethyl-2-methoxy-4-(4-(methylsulfonyl)piperazin-1-yl)piperidin-1-yl)phenylamino)pyrimidin-4-yl)H-imidazo[1,2-a]pyridin-2-yl)-2-methoxybenzamide/1089283-49-7/$C_{44}H_{47}F_2N_9O_5S$ | Inhibitor of IGF-1R and IR | GSK1904529A/Selleck Chemicals/S1093 | 1 µM at S6 |
| N-(4-(3-(2-aminopyrimidin-4-yl)pyridin-2-yloxy)phenyl)-4-(4-methylthiophen-2-yl)phthalazin-1-amine/945595-80-2/$C_{28}H_{21}N_7OS$ | pan-Aurora kinases inhibitor for Aurora A/B/C | AMG-900/Selleck Chemicals/S2719 | 1 µM at S6 |
| 5-((1-(3-isopropyl-1,2,4-oxadiazol-5-yl)piperidin-4-yl)methoxy)-2-(4-(methylsulfonyl)phenyl)pyridine/1032823-75-8/$C_{23}H_{28}N_4O_4S$ | GPR119 agonist | GSK1292263/Selleck Chemicals/S2149 | 1 µM at S6 |
| 4-(5-Amino-1-(2,6-difluorobenzoyl)-1H-[1,2,4]triazol-3-ylamino)-benzenesulfonamide/443797-96-4/$C_{15}H_{12}F_2N_6O_3S$ | pan-CDK inhibitor with the highest potency on CDK1/2 | JNJ-7706621/Selleck Chemicals/S1249 | 1 µM at S6 |

TABLE III-continued

Small molecules evaluated

| Chemical name/CAS #/Molecular formula | Target | Small Molecule Name/Vendor/Catalog No. | Concentration |
|---|---|---|---|
| 6-(difluoro(6-(1-methyl-1H-pyrazol-4-yl)-[1,2,4]triazolo[4,3-b]pyridazin-3-yl)methyl)quinoline/943540-75-8/$C_{19}H_{13}F_2N_7$ | inhibitor of c-Met | JNJ-38877605/Selleck Chemicals/S1114 | 1 μM at S6 |
| (R)-4-(8-cyclopentyl-7-ethyl-5-methyl-6-oxo-5,6,7,8-tetrahydropteridin-2-ylamino)-3-methoxy-N-(1-methylpiperidin-4-yl)benzamide/755038-02-9/$C_{28}H_{39}N_7O_3$ | Plk1 inhibitor | BI 2536/Selleck Chemicals/S1109 | 1 μM at S6 |
| N-hydroxy-2-(4-(((1-methyl-1H-indol-3-yl)methylamino)methyl)piperidin-1-yl)pyrimidine-5-carboxamide/875320-29-9/$C_{21}H_{26}N_6O_2$ | HDAC inhibitor with highest potency for HDAC1 and lowest potency for HDACs 6 and 7; Phase 2 | Quisinostat (JNJ-26481585)/Selleck Chemicals/S1096 | 1 μM at S6 |
| cyclohexyl 2,7,7-trimethyl-4-(4-nitrophenyl)-5-oxo-1,4,5,6,7,8-hexahydroquinoline-3-carboxylate/313967-18-9/$C_{25}H_{30}N_2O_5$ | inhibitor of Notch signaling | FLI-06/Selleck Chemicals/S7399 | 1 μM at S6 |
| 4H-[1,2,4]Triazolo[4,3-a][1,4]benzodiazepine-4-acetamide, 6-(4-chlorophenyl)-N-ethyl-8-methoxy-1-methyl-, (4S)-/1260907-17-2/$C_{22}H_{22}ClN_5O_2$ | inhibitor for BET proteins | I-BET-762 (GSK525762)/Selleck Chemicals/S7189 | 1 μM at S6 |
| N-(6-(4-(2-((4-((4-methylpiperazin-1-yl)methyl)-3-(trifluoromethyl)phenyl)amino)-2-oxoethyl)phenoxy)pyrimidin-4-yl)cyclopropanecarboxamide/1421227-53-3/$C_{29}H_{31}F_3N_6O_3$ | small molecule that promotes pancreatic β cell proliferation in rodent and human primary islets | WS6/Xcess Biosciences, Inc./M60097-2s | 1 μM at S6 |
| 1-[3-[[[(2R,3S,4R,5R)-5-(4-Amino-5-bromo-7H-pyrrolo[2,3-d]pyrimidin-7-yl)-3,4-dihydro-xytetrahydrofuran-2-yl]methyl](isopropyl)amino]pro-pyl]-3-[4-(2,2-dimethylethyl)phenyl]urea/—/$C_{28}H_{40}BrN_7O_4$ | DOT1L methyltransferase inhibitor | SGC0946/Selleck Chemicals/S7079 | 1 μM at S6 |
| 9H-Purin-6-amine, 9-[5-deoxy-5-[[cis-3-[2-[6-(1,1-dimethylethyl)-1H-benzimidazol-2-yl]ethyl]cyclobutyl](1-methylethyl)amino]-β-D-ribofuranosyl]-/1380288-87-8/$C_{30}H_{42}N_8O_3$ | inhibitor of protein methyltransferase DOT1L | EPZ5676/Selleck Chemicals/S7062 | 1 μM at S6 |
| (2R)-2-(N-(2-fluoro-4-(1,2,4-oxadiazol-3-yl)benzyl)-4-chlorophenylsulfonamido)-5,5,5-trifluoropentanamide/1146699-66-2/$C_{20}H_{17}ClF_4N_4O_4S$ | γ-secretase inhibitor of Aβ40 and Aβ42 | Avagacestat (BMS-708163)/Selleck Chemicals/S1262 | 1 μM at S6 |
| [1,1'-Biphenyl]-3-carboxamide, N-[(1,2-dihydro-4,6-dimethyl-2-oxo-3-pyridinyl)methyl]-5-[ethyl(tetrahydro-2H-pyran-4-yl)amino]-4-methyl-4'-(4-morpholinylmethyl)-/1403254-99-8/$C_{34}H_{44}N_4O_4$ | EZH2 inhibitor | EPZ-6438/Selleck Chemicals/S7128 | 1 μM at S6 |
| N-(4-(6,7-dimethoxyquinolin-4-yloxy)phenyl)-N-(4-fluorophenyl)cyclopropane-1,1-dicarboxamide/849217-68-1/$C_{28}H_{24}FN_3O_5$ | VEGFR2 inhibitor | Cabozantinib (XL184, BMS-907351)/Selleck Chemicals/S1119 | 1 μM at S6 |
| 3-(benzo[d]thiazol-2-yl)-6-ethyl-7-hydroxy-8-(piperidin-1-ylmethyl)-4H-chromen-4-one/222716-34-9/$C_{24}H_{24}N_2O_3S$ | Skp2 inhibitor | SKP2-C25/Xcess Biosciences, Inc./M60136-2s | 1 μM at S6 |
| 5-Chloro-2-[(E)-2-[phenyl(pyridin-2-yl)methylidene]hydrazin-1-yl]pyridine/199596-05-9/C17H13ClN4 | Jumonji histone demethylase inihibitor | JIB-04/Selleck Chemicals/S7281 | 1 μM at S6 |
| 1H-1,2,4-Triazole-3,5-diamine,1-(6,7-dihydro-5H-benzo[6,7]cyclohepta[1,2-c]pyridazin-3-yl)-N3-[(7S)-6,7,8,9-tetrahydro-7-(1-pyrrolidinyl)-5H-benzocyclohepten-2-yl]-/1037624-75-1/$C_{30}H_{34}N_8$ | inhibitor of Axl | R428 (BGB324)/Selleck Chemicals/S2841 | 1 μM at S7 |
| 2-Chloro-3-[2-(2,4-dichlorophenoxy)ethoxy]-6-(fluoromethyl)pyridine/1355026-60-6/$C_{14}H_{11}Cl_3FNO_2$ | Potent sphingosine-1-phosphate receptor 4 (S1P4) agonist | CYM50260/Tocris Bioscience/4677 | 2 μM at S6-S7 |
| N,N-Dicyclohexyl-5-cyclopropyl-3-isoxazolecarboxamide/945128-26-7/$C_{19}H_{28}N_2O_2$ | Selective sphingosine-1-phosphate receptor 3 (S1P3) allosteric | CYM5541/Tocris Bioscience/4897 | 2 μM at S6-S7 |
| 5-[4-Phenyl-5-(trifluoromethyl)thiophen-2-yl]-3-[3-(trifluoromethyl)phenyl]1,2,4-oxadiazole/256414-75-2/$C_{20}H_{10}F_6N_2OS$ | potent and selective sphingosine-1-phosphate 1 (S1P1) receptor agonist | SEW2871/Tocris Bioscience/2284 | 2 μM at S6-S7 |

TABLE III-continued

Small molecules evaluated

| Chemical name/CAS #/Molecular formula | Target | Small Molecule Name/Vendor/Catalog No. | Concentration |
|---|---|---|---|
| [9S-(9α,10β,11β,13α)]-2,3,10,11,12,13-Hexahydro-10-methoxy-9-methyl-11-(methylamino)-9,13-epoxy-1H,9H-diindolo[1,2,3-gh:3',2',1'-lm]pyrrolo[3,4-j][1,7]benzodiazonin-1-one/62996-74-1/$C_{20}H_{26}N_4O_3$ | Broad spectrum protein kinase inhibitor | Staurosporine/Tocris Bioscience/1285 | 10 nM at S6-S7 |

As shown in FIGS. 8A, 8B, 8C, 8D and 8E, which are graphs depicting data from real-time PCR analyses of the expression of insulin and MAFA after treatment with small molecules, addition of EPZ-5676 (inhibitor of protein methyltransferase DOT1L) and AXL inhibitor (R428) significantly upregulated expression of MAFA as compared to untreated cultures at Stage 6 and Stage 7, respectively.

Example 3 (Prophetic)

Generation of Endocrine Cells Co-Expressing Insulin, PDX-1, NKX6.1, and MAFA in Suspension Cultures Cells of the human embryonic stem cell line H1 (WA01) are seeded as single cells at $1 \times 10^5$ cells/cm² on MATRIGEL™ (1:30 dilution)-coated dishes in a media comprising of DMEM-F12, GlutaMAX™ (1:100 dilution), 0.25 mM ascorbic acid, 100 ng/ml of FGF2 (R & D systems, MN), 1 ng/ml of TGF-β, ITS-X (1:100 dilution), 2% FAF-BSA, and 20 ng/ml of IGF-1, supplemented with 10 μM of Y-27632. Forty-eight hours post-seeding, the cultures are washed in incomplete PBS (phosphate buffered saline without Mg or Ca) followed by incubation with 1× TrypLE™ Express Enzyme for 3 to 5 minutes at 37° C. The released cells are rinsed with DMEM-F12 and spun at 1000 rpm for 5 minutes. The resulting cell pellet are resuspended in DMEM-F12 supplemented with 10 μM Y-27632, 1× GlutaMAX™, 0.25 mM ascorbic acid, 100 ng/ml FGF2, 1 ng/ml TGF-β, ITS-X at a (1:100 dilution, 2% FAF-BSA, and 20 ng/ml of IGF-1 and the single cell suspension seeded at approximately 1.3 to $1.5 \times 10^5$ cells/cm². The cultures are fed every day with medium and differentiation, according to the following protocol, was initiated 48 hrs. following seeding resulting in an about 90% starting confluency. Stage 1 through Stage 4 are maintained on planar adherent cultures while Stages 5 through 7 are maintained in suspension cultures.

Stage 1 (3 Days):
Cells are plated on MATRIGEL™ (1:30 dilution)-coated dishes were first rinsed with 1× incomplete DPBS and then are cultured for one day in Stage 1 media: MCDB-131 medium supplemented with 0.5% FAF-BSA, 1.2 g/1000 ml sodium bicarbonate; 1× concentration of GlutaMAX™; 4.5 mM D-glucose; 100 ng/ml GDF8; and 1 μM MCX compound. Cells are then cultured for an additional day in MCDB-131 medium supplemented with 0.5% FAF-BSA, 1.2 g/1000 ml sodium bicarbonate, 1× concentration of GlutaMAX™, 4.5 mM D-glucose, 100 ng/ml GDF8, and 0.1 μM MCX compound. Cells are then cultured for an additional day in MCDB-131 medium supplemented with 0.5% FAF-BSA, 1.2 g/1000 ml sodium bicarbonate, 1× concentration of GlutaMAX™, 4.5 mM D-glucose, and 100 ng/ml GDF8.

Stage 2 (2 Days):
Cells are first rinsed with 1× incomplete DPBS and then are treated for two days with MCDB-131 medium supplemented with 0.5% FAF-BSA; 1.2 g/1000 ml sodium bicarbonate; 1× concentration of GlutaMAX™; 4.5 mM D-glucose; 0.25 mM ascorbic acid and 25 ng/ml FGF7.

Stage 3 (2 Days):
Cells are treated with BLAR custom medium supplemented with a 1:200 dilution of ITS-X; 4.5 mM glucose; 1× concentration of GlutaMAX™; 2.5 g/1000 ml sodium bicarbonate; 2% FAF-BSA; 0.25 μM SANT-1; 1 μM RA; 25 ng/ml FGF7; 0.25 mM ascorbic acid; 200 nM TPB; and 100 nM LDN-193189 for two days.

Stage 4 (3 Days):
Cells are treated with BLAR medium supplemented with a 1:200 dilution of ITS-X; 4.5 mM glucose; 1× concentration of GlutaMAX™; 2.5 g/1000 ml sodium bicarbonate; 2% FAF-BSA; 0.25 μM SANT-1; 100 nM RA; 2 ng/ml FGF7; 100 nM LDN-193189; 0.25 mM ascorbic acid; and 200 nM TPB for three days, then at end of Stage 4 cells cultured on planar dishes are treated for 4 hours with 10 μM of Y-27632, are rinsed with PBS and are treated for 5 minutes at room temperature with 1× concentration of StemPro® Accutase® enzyme (Life Technologies, #A11105-01) and the enzyme is removed, and are rinsed with BLAR basal media and cells are scraped using a cell scraper and broken into cell clusters (<100 micron). The cell clusters are transferred into a disposable polystyrene 125 ml Spinner Flask (Corning), and spun at 80 to 100 rpm in suspension with Stage 5 media specified below.

Stage 5 (3 Days):
Stage 4 cells are prepared as clusters are cultured in suspension in BLAR medium supplemented with a 1:200 dilution of ITS-X; 20 mM glucose (final); 1× GlutaMAX™; 1.5 g/1000 ml sodium bicarbonate; 2% FAF-BSA; 0.25 mM ascorbic acid; 10 μg/ml of heparin, 10 μM $ZnSO_4$, 0.25 μM SANT-1; 50 nM RA; 100 nM LDN-193189; 1 μM of T3 as 3,3',5-triiodo-L-thyronine sodium salt, and 10000 nM of ALK5 inhibitor II for three days.

Stage 6 (7 Days):
Stage 5 cells are cultured in suspension and treated with BLAR medium supplemented with a 1:200 dilution of ITS-X; 20 mM Glucose (final); 1× concentration of GlutaMAX™; 1.5 g/1000 ml sodium bicarbonate; 2% FAF-BSA; 0.25 mM ascorbic acid; 10 μg/ml of heparin, 10 μM $ZnSO_4$, 100 nM LDN-193189, 1 μM T3 as 3,3',5-triiodo-L-thyronine sodium salt, 100 nM gamma secretase inhibitor XX, and 10000 nM ALK5 inhibitor II for 7 days.

Stage 7 (15 Days):
Stage 6 cells are cultured in suspension and are treated with BLAR medium supplemented with a 1:200 dilution of ITS-X; 20 mM Glucose (final); 1× concentration of GlutaMAX™; 0.0015 g/ml sodium bicarbonate; 2% FAF-BSA; 10 μg/ml of heparin, 10 μM $ZnSO_4$, 1 μM T3 as 3,3',5-triiodo-L-thyronine sodium salt, 10000 nM ALK5 inhibitor II, 10 µM Trolox, 1 mM N-acetyl cysteine, and 2 µM AXL inhibitor (R428) for up to 15 days.

At Stages 5-7, aliquots of cell clusters are removed and characterized by PCR, FACS and immune histochemistry for co-expression of insulin, NKX6.1, PDX-1, and MAFA. It is expected that the results of such testing will show co-expression of insulin, PDX1, NKX6.1 and MAFA within the same cell and a population of cells in which at least about 10% of the cell population showed such expression.

Example 4 mRNA Expression of AXL and Co-Ligand GAS6 is Very Low for Stage 7 or Human Islet Cells Cells of the human embryonic stem cell line H1 (WA01) were seeded as single cells at $1\times10^5$ cells/cm$^2$ on MATRIGEL™ (1:30 dilution)-coated dishes in a media comprising of Essential 8™ ("E8") (BD Biosciences; Catalog No. 356231). At 48 hours post-seeding, the cultures were washed in 1× incomplete PBS followed by incubation with 1× TrypLE™ Express Enzyme (Life Science; Catalog No. 14190) for 3 to 5 minutes at 37° C. The released cells were rinsed with E8 and spun at 1000 rpm for 5 minutes. The resulting cell pellet was resuspended in E8 supplemented with 10 µM Y-27632 and the single cell suspension was seeded at approximately 1.3 to $1.5\times10^5$ cells/cm$^2$. The cultures were fed every day with E8 medium and differentiation, according to the following protocol, was initiated 48 hrs. following seeding resulting in an about 90% starting confluency.

Stage 1 (3 Days):
Cells were plated on MATRIGEL™ (1:30 dilution)-coated dishes were first rinsed with 1× incomplete DPBS and then cultured for one day in Stage 1 media: MCDB-131 medium supplemented with 0.5% FAF-BSA, 1.5 g/1000 ml sodium bicarbonate; 1× concentration of Glutamax™, 4.5 mM D-glucose; 100 ng/ml GDF8; and 1.5 µM MCX compound. Cells were then cultured for an additional day in MCDB-131 medium supplemented with 0.5% FAF-BSA, 1.5 g/1000 ml sodium bicarbonate, 1× concentration Glutamax™, 4.5 mM D-glucose concentration, 100 ng/ml GDF8, and 0.1 µM MCX compound. Cells were then cultured for an additional day in MCDB-131 medium supplemented with 0.5% FAF-BSA, 1.5 g/1000 ml sodium bicarbonate, 1× concentration of Glutamax™, 4.5 mM D-glucose, and 100 ng/ml GDF8.

Stage 2 (2 Days):
Cells were first rinsed with 1× incomplete DPBS and then cultured for two days with MCDB-131 medium supplemented with 0.5% FAF-BSA; 1.5 g/1000 ml sodium bicarbonate; 1× concentration of Glutamax™, 4.5 mM D-glucose; 0.25 mM ascorbic acid and 50 ng/ml FGF7.

Stage 3 (2 Days):
Cells were cultured in BLAR custom medium supplemented with a 1:100 dilution of ITS-X; 1× concentration Glutamax™, 4.5 mM D-glucose; 2.5 g/1000 ml sodium bicarbonate; 2% FAF-BSA; 0.25 µM SANT-1; 1 µM RA; 25 ng/ml FGF7; 0.25 mM ascorbic acid; 300 nM TPB; and 100 nM LDN-193189 for two days.

Stage 4 (3 Days):
Cells were cultured in BLAR medium supplemented with a 1:100 dilution of ITS-X; 1× concentration Glutamax™, 4.5 mM D-glucose; 2.5 g/1000 ml sodium bicarbonate; 2% FAF-BSA; 0.25 µM SANT-1; 0.1 µM RA; 2 ng/ml FGF7; 100 nM LDN-193189; 0.25 mM ascorbic acid; and 200 nM TPB for three days, then at end of Stage 4 cells cultured on planar dishes were treated for 4 hours with 10 µM of Y-27632, rinsed with 1× incomplete PBS and treated for 3 to 5 minutes at room temperature with 1× TrypLE™. The enzyme was removed, the cells released and rinsed with BLAR media and transferred into a disposable polystyrene 125 ml Spinner Flask, and spun at 1000 rpm for 3 mins. The resulting cell pellet was resuspended as single cells at a density of approximately $0.5\times10^5$ cells/cm$^2$ on filter inserts (BD Biosciences; Catalog No. 3420) (5 to 10 µL per spot for a total of 0.25 to 0.5 million cells/spot). Each spotted area measured approximately 1 to 2 mm in diameter depending on the volume of cells added. For 6-well inserts, 1.5 mL/well was added to the bottom of each insert whereas 8 mL was added for 10 cm filter inserts. Typically, 20 to 15 spots were used per well of a 6-well insert and 80 to 90 spots were used for 10 cm inserts.

Stage 5 (3 Days):
Stage 4 cells were cultured in BLAR medium supplemented with a 1:100 dilution of ITS-X; 20 mM glucose (final); 1.5 g/1000 ml sodium bicarbonate; 2% FAF-BSA; 10 µg/ml of heparin, 10 µM ZnSO$_4$, 0.25 µM SANT-1; 0.05 µM RA; 100 nM LDN-193189, 1 µM of T3 as 3,3',5-triiodo-L-thyronine sodium salt, and 10 µM of ALK5 inhibitor II for three days.

Stage 6 (7 Days):
Stage 5 cells were cultured in BLAR medium supplemented with a 1:100 dilution of ITS-X; 20 mM glucose (final); 1.5 g/1000 ml sodium bicarbonate; 2% FAF-BSA; 10 µg/ml of heparin, 10 µM ZnSO$_4$, 100 nM LDN-193189, 1 µM T3 as 3,3',5-triiodo-L-thyronine sodium salt, 100 nM gamma secretase inhibitor XX, and 10 µM ALK5 inhibitor II for 7 days.

Stage 7 (7 days):
Stage 6 cells were cultured in BLAR medium supplemented with a 1:100 dilution of ITS-X; 20 mM glucose (final); 1.5 g/L sodium bicarbonate; 2% FAF-BSA; 10 µg/ml of heparin, 10 µM ZnSO$_4$, 1 µM T3 as 3,3',5-triiodo-L-thyronine sodium salt, 10 µM ALK5 inhibitor II, 1 mM N-acetyl cysteine, and 2 µM AXL inhibitor (R428) for 7 days.

At Stage 4, day 3, Stage 5, day 3, Stage 6, day 3, and Stage 7, day 7 mRNA was collected and expression of AXL and GAS 6 evaluated as compared to undifferentiated human stem cells and cadaveric human islets (Prodo Labs, California). As depicted in FIG. 9, expression of AXL was present at a high level in undifferentiated stem cells. However, differentiation of stem cells towards pancreatic endoderm, pancreatic endocrine and immature beta cells resulted in a precipitous drop in AXL expression. Moreover, there was a low level of GAS6 expression maintained at Stages 4 through 7. Expression of AXL was also significantly lower in human islets as compared to undifferentiated stem cells. The results show that Stage 6 and 7 cells have very low expression of AXL.

Example 5

R428 Inhibits AXL and Many Additional Kinases

The efficiency of the AXL inhibitor R428 for targeting different kinases was assessed by Kinase Profiling Services using 100 µM ATP concentration (EMD Millipore). R428 was tested at 1 and 10 µM. Table IV lists the kinases profiled along with the efficiency in targeting the kinases with a lower number indicating a more robust inhibition of a particular kinase.

TABLE IV

Kinase profiling of R428

| Kinase | R428 1001010 @ 1 μM | R428 1001010 @ 10 μM |
|---|---|---|
| ALK4(h) | 84 | 48 |
| Aurora-A(h) | 20 | 3 |
| Aurora-B(h) | 1 | 0 |
| Axl(h) | −1 | −1 |
| Blk(h) | 27 | 2 |
| CaMKIIβ(h) | 76 | 5 |
| CaMKIδ(h) | 76 | 24 |
| CDK1/cyclinB(Hh) | 101 | 88 |
| CDK5/p35(h) | 101 | 94 |
| CHK1(h) | 71 | 23 |
| CHK2(h) | 47 | 9 |
| CK2(h) | 103 | 106 |
| CK2α2(h) | 112 | 97 |
| CLK2(h) | 78 | 28 |
| cSRC(h) | 51 | 10 |
| EGFR(h) | 89 | 40 |
| Eph A 2(h) | 54 | 12 |
| FGFR1(h) | 17 | 1 |
| Flt3(h) | 9 | 1 |
| GSK3α(h) | 95 | 105 |
| GSK3β(h) | 106 | 99 |
| IGF-1R(h) | 93 | 58 |
| IKKβ(h) | 86 | 53 |
| IR(h) | 83 | 24 |
| IRAK4(h) | 94 | 51 |
| JAK2(h) | 96 | 41 |
| JAK3(h) | 69 | 18 |
| MAPK1(h) | 108 | 106 |
| Met(h) | 49 | −1 |
| NEK2(h) | 60 | 10 |
| PAK4(h) | 97 | 73 |
| PDGFRβ(h) | 37 | 21 |
| Pim-2(h) | 87 | 74 |
| PKA(h) | 88 | 35 |
| PKBα(h) | 87 | 57 |
| PKCα(h) | 101 | 96 |
| PKCβ1(h) | 102 | 95 |
| Plk1(h) | 83 | 65 |
| Plk3(h) | 101 | 81 |
| Ret(h) | 1 | 1 |
| ROCK-1(h) | 93 | 41 |
| Rsk3(h) | 2 | 1 |
| SAPK3(h) | 106 | 108 |
| SAPK4(h) | 94 | 91 |
| TGFBR1(h) | 97 | 69 |
| TrkC(h) | 47 | 13 |
| ZAP-70(h) | 92 | 66 |
| ZIPK(h) | 97 | 46 |

The kinase profiling results indicate that R428 inhibits AXL as expected. However, additionally R428 potently inhibits RSK3, Ret, Flt, FGFrl, AuroraA and AuroraB kinases at 1 and 10 μM. This signifies that the mechanism of R428 action in induction of MAFA, may not be through AXL receptor inhibition. In fact, the examples herein show that mRNA expression for AXL at Stage 7 is very low highlighting that the mechanism of action of R428 in inducing MAFA expression is not through inhibition of AXL, but rather through the inhibition of other kinases, such as RSK3 and aurora kinases.

Example 6

Inhibition of Aurora Kinase Expression Enhanced MAFA Expression at Stage 7 in the Absence of R428

Cells of the human embryonic stem cell line H1 (WA01) were seeded as single cells at 1×10⁵ cells/cm² on MATRIGEL™ (1:30 dilution) coated dishes in E8 media. At about 70 to 80% confluency, the cultures were washed in 1× incomplete DPBS followed by incubation with 1× TrypLE™ Express Enzyme for 3 to 5 minutes at 37° C. The released cells were rinsed with E8 and spun at 1000 rpm for 5 minutes. The resulting cell pellet was resuspended in E8 supplemented with 10 μM Y-27632 and the single cell suspension was seeded at approximately 1.3 to 1.5×10⁵ cells/cm². The cultures were fed every day with E8 medium and differentiation, according to the following protocol, was initiated 48 hrs. following seeding resulting in an about 90% starting confluency.

Stage 1 (3 Days):
Cells were plated on MATRIGEL™ (1:30 dilution) coated dishes were first rinsed with 1× incomplete DPBS and then cultured for one day in Stage 1 media: MCDB-131 medium supplemented with 0.5% FAF-BSA, 1.5 g/1000 ml sodium bicarbonate; 10 mM final glucose concentration; 100 ng/ml GDF8; and 1.5 μM MCX compound. Cells were then cultured for an additional day in MCDB-131 medium supplemented with 0.5% FAF-BSA, 1.5 g/1000 ml sodium bicarbonate, 10 mM final glucose concentration, 100 ng/ml GDF8, and 0.1 μM MCX compound. Cells were then cultured for an additional day in MCDB-131 medium supplemented with 0.5% FAF-BSA, 1.5 g/1000 ml sodium bicarbonate, 10 mM final glucose concentration, and 100 ng/ml GDF8.

Stage 2 (2 Days):
Cells were rinsed with 1× incomplete DPBS and then cultured for two days with MCDB-131 medium supplemented with 0.5% FAF-BSA; 1.5 g/1000 ml sodium bicarbonate; 10 mM final glucose concentration; 0.25 mM ascorbic acid and 50 ng/ml FGF7.

Stage 3 (2 Days):
Cells were cultured in BLAR custom medium supplemented with a 1:100 dilution of ITS-X; 10 mM final glucose concentration; 2.5 g/1000 ml sodium bicarbonate; 2% FAF-BSA; 0.25 μM SANT-1; 1 μM RA; 25 ng/ml FGF7; 0.25 mM ascorbic acid; 300 nM TPB; and 100 nM LDN-193189 for two days.

Stage 4 (3 Days):
Cells were cultured in BLAR medium supplemented with a 1:100 dilution of ITS-X; 10 mM final glucose concentration; 2.5 g/1000 ml sodium bicarbonate; 2% FAF-BSA; 0.25 μM SANT-1; 0.1 μM RA; 2 ng/ml FGF7; 100 nM LDN-193189; 0.25 mM ascorbic acid; and 200 nM TPB for three days, then at end of Stage 4 cells cultured on planar dishes were treated for 4 hours with 10 μM of Y-27632, rinsed with 1× incomplete PBS and treated for 3 to 5 minutes at room temperature with 1× TrypLE™. The enzyme was removed, the cells released and rinsed with BLAR media and transferred into a disposable polystyrene 125 ml Spinner Flask, and spun at 1000 rpm for 3 mins. The resulting cell pellet was resuspended as single cells at a density of approximately 0.5×10⁵ cells/cm² on filter inserts (5 to 10 μl per spot for a total of 0.25 to 0.5 million cells/spot). Each spotted area measured approximately 1 to 2 mm in diameter depending on the volume of cells added. For 6-well inserts, 1.5 mL/well was added to the bottom of each insert whereas 8 mL was added for 10 cm filter inserts. Typically, 20 to 15 spots were used per well of a 6-well insert ad 80 to 90 spots were used for 10 cm inserts.

Stage 5 (3 Days):
Stage 4 cells were cultured in BLAR medium supplemented with a 1:100 dilution of ITS-X; 20 mM glucose (final); 1.5 g/1000 ml sodium bicarbonate; 2% FAF-BSA; 10 μg/ml of heparin, 10 μM ZnSO₄, 0.25 μM SANT-1; 0.05 μM RA; 100 nM LDN-193189, 1 μM of T3 as 3,3',5-triiodo-L-thyronine sodium salt, and 10 μM of ALK5 inhibitor II for three days.

Stage 6 (7 Days):

Stage 5 cells were cultured in BLAR medium supplemented with a 1:100 dilution of ITS-X; 20 mM glucose (final); 1.5 g/1000 ml sodium bicarbonate; 2% FAF-BSA; 10 μg/ml of heparin, 10 μM ZnSO$_4$, 100 nM LDN-193189, 1 μM T3 as 3,3',5-triiodo-L-thyronine sodium salt, 100 nM gamma secretase inhibitor XX, and 10 μM ALK5 inhibitor II for 7 days.

Stage 7 (7 Days):

Stage 6 cells were cultured for seven days in BLAR medium supplemented with a 1:100 dilution of ITS-X; 20 mM glucose (final); 1.5 g/L sodium bicarbonate; 2% FAF-BSA; 10 μg/ml of heparin, 10 μM ZnSO$_4$, 1 μM T3 as 3,3',5-triiodo-L-thyronine sodium salt, 10 μM ALK5 inhibitor II, 1 mM N-acetyl cysteine. Some cultures also included one of 2 μM R428, 2 μM aurora kinase inhibitor VI (4-(4-(N-Benzoylamino)anilino)-6-methoxy-7-(3-(1-morpholino)propoxy)quinazoline) (EMD Millipore; Catalog No, 18941), or 2 μM aurora kinase inhibitor II (4-(4'-Benzamidoanilino)-6,7-dimethoxyquinazoline) (EMD Millipore; Catalog No. 189404).

At Stage 7, day 7, mRNA was collected and expression of MAFA, UCN3, PDX1, NKX6.1, insulin and G6PC2 evaluated as compared to undifferentiated human stem cells. As depicted in FIGS. 10A, 10B, 10C, 10D, 10E and 10F, removal of R428 resulted in a significant decrease in MAFA expression. A significant rise in UCN3 and G6PC2 expression, both markers of mature beta cells, was noted for cultures not treated with R428 suggesting that, although R428 increases MAFA expression, the compound reduces other beta cell maturation markers. Substitution of aurora kinase inhibitors for R428 restored MAFA expression while not decreasing G6PC2 levels. Thus, the induction of MAFA expression by R428 at Stage 7 was likely not through AXL inhibition, but rather through inhibition of aurora kinases. The use of aurora kinase inhibitor II resulted in an increase in MAFA expression and maintenance of UCN3 and G6PC2 expression.

Example 7

Inhibition of Aurora Kinase or RSK Enhanced Expression of MAFA Expression at Stage 7 in the Absence of R428

Cells of the human embryonic stem cell line H1 (WA01) were seeded as single cells at 1×10$^5$ cells/cm$^2$ on MATRIGEL™ (1:30 dilution) coated dishes in E8 media. At about 70 to 80% confluency, the cultures were washed in 1× incomplete DPBS followed by incubation with 1× TrypLE™ Express Enzyme for 3 to 5 minutes at 37° C. The released cells were rinsed with E8 and spun at 1000 rpm for 5 minutes. The resulting cell pellet was resuspended in E8 supplemented with 10 μM Y-27632 and the single cell suspension was seeded at approximately 1.3 to 1.5×10$^5$ cells/cm$^2$. The cultures were fed every day with E8 medium and differentiation, according to the following protocol, was initiated 48 hrs. following seeding resulting in an about 90% starting confluency.

Stage 1 (3 Days):

Cells were plated on MATRIGEL™ (1:30 dilution) coated dishes were first rinsed with 1× incomplete DPBS and then cultured for one day in Stage 1 media: MCDB-131 medium supplemented with 0.5% FAF-BSA, 1.5 g/1000 ml sodium bicarbonate; 10 mM final glucose concentration; 100 ng/ml GDF8; and 1.5 μM MCX compound. Cells were then cultured for an additional day in MCDB-131 medium supplemented with 0.5% FAF-BSA, 1.5 g/1000 ml sodium bicarbonate, 10 mM final glucose concentration, 100 ng/ml GDF8, and 0.1 μM MCX compound. Cells were then cultured for an additional day in MCDB-131 medium supplemented with 0.5% FAF-BSA, 1.5 g/1000 ml sodium bicarbonate, 10 mM final glucose concentration, and 100 ng/ml GDF8.

Stage 2 (2 Days):

Cells were rinsed with 1× incomplete DPBS and then cultured for two days with MCDB-131 medium supplemented with 0.5% FAF-BSA; 1.5 g/1000 ml sodium bicarbonate; 10 mM final glucose concentration; 0.25 mM ascorbic acid and 50 ng/ml FGF7.

Stage 3 (2 Days):

Cells were cultured in BLAR custom medium supplemented with a 1:100 dilution of ITS-X; 10 mM final glucose concentration; 2.5 g/1 000 ml sodium bicarbonate; 2% FAF-BSA; 0.25 μM SANT-1; 1 μM RA; 25 ng/ml FGF7; 0.25 mM ascorbic acid; 300 nM TPB; and 100 nM LDN-193189 for two days.

Stage 4 (3 Days):

Cells were cultured in BLAR medium supplemented with a 1:100 dilution of ITS-X; 10 mM final glucose concentration; 2.5 g/1000 ml sodium bicarbonate; 2% FAF-BSA; 0.25 μM SANT-1; 0.1 μM RA; 2 ng/ml FGF7; 100 nM LDN-193189; 0.25 mM ascorbic acid; and 200 nM TPB for three days, then at end of Stage 4 cells cultured on planar dishes were treated for 4 hours with 10 μM of Y-27632, rinsed with 1× incomplete PBS and treated for 3 to 5 minutes at room temperature with 1× TrypLE™. The enzyme was removed, the cells released and rinsed with BLAR media and transferred into a disposable polystyrene 125 ml Spinner Flask, and spun at 1000 rpm for 3 mins. The resulting cell pellet was resuspended as single cells at a density of approximately 0.5×10$^5$ cells/cm$^2$ on filter inserts (5 to 10 μl per spot for a total of 0.25 to 0.5 million cells/spot). Each spotted area measured approximately 1 to 2 mm in diameter depending on the volume of cells added. For 6-well inserts, 1.5 mL/well was added to the bottom of each insert whereas 8 mL was added for 10 cm filter inserts. Typically, 20 to 15 spots were used per well of a 6-well insert ad 80 to 90 spots were used for 10 cm inserts.

Stage 5 (3 Days):

Stage 4 cells were cultured in BLAR medium supplemented with a 1:100 dilution of ITS-X; 20 mM glucose (final); 1.5 g/1000 ml sodium bicarbonate; 2% FAF-BSA; 10 μg/ml of heparin, 10 μM ZnSO$_4$, 0.25 μM SANT-1; 0.05 μM RA; 100 nM LDN-193189, 1 μM of T3 as 3,3',5-triiodo-L-thyronine sodium salt, and 10 μM of ALK5 inhibitor II for three days.

Stage 6 (7 Days):

Stage 5 cells were cultured in BLAR medium supplemented with a 1:100 dilution of ITS-X; 20 mM glucose (final); 1.5 g/1000 ml sodium bicarbonate; 2% FAF-BSA; 10 μg/ml of heparin, 10 μM ZnSO$_4$, 100 nM LDN-193189, 1 μM T3 as 3,3',5-triiodo-L-thyronine sodium salt, 100 nM gamma secretase inhibitor XX, and 10 μM ALK5 inhibitor II for 7 days.

Stage 7 (7 Days):

Stage 6 cells were cultured for fourteen days in BLAR medium supplemented with a 1:100 dilution of ITS-X; 20 mM glucose (final); 1.5 g/L sodium bicarbonate; 2% FAF-BSA; 10 μg/ml of heparin, 10 M ZnSO$_4$, 1 μM T3 as 3,3',5-triiodo-L-thyronine sodium salt, 10 μM ALK5 inhibitor II, 1 mM N-acetyl cysteine. Some cultures also included one of 2 µM R428, 2-5 µM RSK inhibitor II (2-(3,5-Difluoro-4-hydroxy-anilino)-8-isopentyl-5,7-dimethyl-7H-pteridin-6-one) (EMD Millipore; Catalog No, 559286-5MG), 2-5 µM aurora kinase inhibitor II (EMD Millipore, or a combination of 2-5 µM RSK inhibitor II and 2-5 µM aurora kinase II inhibitor.

At Stage 7, day 14, mRNA was collected and compared to undifferentiated human stem cells. As depicted in FIG. 1, removal of R428 resulted in a significant decrease in MAFA expression. Substitution with aurora kinase inhibitor II for R428 restored MAFA expression. Similarly, substitution with RSK inhibitor for R428 restored MAFA expression. Substitution with aurora kinase inhibitor II and RSK inhibitor for R428 further enhanced MAFA expression. This data indicates that the induction of MAFA expression by R428 was likely not through AXL inhibition, but rather through inhibition of aurora kinase, RSK or a combination thereof.

What is claimed is:

1. An in vitro cell culture comprising (i) a population of human pancreatic endocrine cells, in which at least 10% of the differentiated cells express insulin, PDX1, NKX6.1, and MAFA, and (ii) a differentiation medium supplemented with L-alanyl-glutamine and an inhibitor selected from the group consisting of an aurora kinase inhibitor, an RSK inhibitor, an inhibitor of protein methyltransferase DOT1L, and combinations thereof, wherein the population is obtained by a step-wise differentiation protocol comprising:
   (a) culturing human pluripotent stem cells in a medium supplemented with either (i) activin A and wnt3A or (ii) GDF-8 and 14-Prop-2-en-1-yl-3,5,7,14,17,23,27-heptaazatetracyclo[19.3.1.1~2,6~.1-8,12~]heptacosa-1(25),2(27),3,5,8(26),9,11,21,23-nonaen-16-one to obtain definitive endoderm cells;
   (b) differentiating the definitive endoderm cells into pancreatic endocrine cells; and
   (c) culturing the pancreatic endocrine cells in the differentiation medium supplemented with L-alanyl-glutamine and an inhibitor selected from the group consisting of an aurora kinase inhibitor, an RSK inhibitor, an inhibitor of protein methyltransferase DOT1L, and combinations thereof.

2. A method of inducing MAFA expression in cells comprising treating human pancreatic endocrine cells with a medium supplemented with an inhibitor selected from the group consisting of an RSK inhibitor, an inhibitor of protein methyltransferase DOT1L, and combinations thereof, wherein the treatment with the inhibitor induces MAFA expression.

3. The method of claim 2, wherein the inhibitor is an RSK inhibitor.

4. The method of claim 3, wherein the RSK inhibitor is RSK inhibitor II.

5. The method of claim 2, wherein the medium further comprises an antioxidant.

6. The method of claim 2, wherein the inhibitor is an inhibitor of protein methyltransferase DOT1L.

7. The method of claim 6, wherein the inhibitor of protein methyltransferase DOT1L is EPZ-5676.

8. An in vitro cell culture comprising (i) a population human pancreatic endocrine cells, in which at least 10% of the differentiated cells express insulin, PDX1, NKX6.1, and MAFA, and (ii) a differentiation medium supplemented with an RSK inhibitor, wherein the population is obtained by a step-wise differentiation protocol comprising:
   (a) culturing human pluripotent stem cells in a medium supplemented with either (i) activin A and wnt3A or (ii) GDF-8 and 14-Prop-2-en-1-yl-3,5,7,14,17,23,27-heptaazatetracyclo[19.3.1.1~2,6~.1~8,12~]heptacosa-1(25),2(27),3,5,8(26),9,11,21,23-nonaen-16-one to obtain definitive endoderm cells;
   (b) differentiating the definitive endoderm cells into pancreatic endocrine cells; and
   (c) culturing the pancreatic endocrine cells in the differentiation medium supplemented with the RSK inhibitor.

9. The in vitro culture of claim 8, wherein the RSK inhibitor is RSK inhibitor II.

10. An in vitro cell culture comprising (i) a population human pancreatic endocrine cells, in which at least 10% of the differentiated cells express insulin, PDX1, NKX6.1, and MAFA, and (ii) a differentiation medium supplemented with an inhibitor of protein methyltransferase DOT1L, wherein the population is obtained by a step-wise differentiation protocol comprising:
   (a) culturing human pluripotent stem cells in a medium supplemented with either (i) activin A and wnt3A or (ii) GDF-8 and 14-Prop-2-en-1-yl-3,5,7,14,17,23,27-heptaazatetracyclo[19.3.1.1~2,6~.1~8,12~]heptacosa-1(25),2(27),3,5,8(26),9,11,21,23-nonaen-16-one to obtain definitive endoderm cells;
   (b) differentiating the definitive endoderm cells into pancreatic endocrine cells; and
   (c) culturing the pancreatic endocrine cells in the differentiation medium supplemented with L-alanyl-glutamine and an inhibitor selected from the group consisting of an aurora kinase inhibitor, an RSK inhibitor, an inhibitor of protein methyltransferase DOT1L, and combinations thereof.

11. The in vitro culture of claim 10, wherein the inhibitor of protein methyltransferase DOT1L is EPZ-5676.

12. The in vitro culture of claim 1, further comprising an antioxidant.

13. A method for inducing MAFA expression in pancreatic endocrine cells comprising culturing the human foregut endoderm cells with an RSK inhibitor, an inhibitor of protein methyltransferase DOT1L, and combinations thereof to obtain mature pancreatic endocrine cells which express MAFA.

14. An in vitro cell culture comprising (i) a population human pancreatic endocrine cells, in which at least 10% of the differentiated cells express insulin, PDX1, NKX6.1, and MAFA, and (ii) a differentiation medium supplemented with L-alanyl-glutamine and an inhibitor selected from the group consisting of an aurora kinase inhibitor, an RSK inhibitor, an inhibitor of protein methyltransferase DOT1L, and combinations thereof, wherein the population is obtained by a step-wise differentiation protocol which comprises culturing human pancreatic endocrine cells in the differentiation medium.

15. The method of claim 13, wherein the method comprises culturing the human foregut endoderm cells with an RSK inhibitor.

16. The method of claim 15, wherein the RSK inhibitor is RSK inhibitor II.

17. The method of claim 13, wherein the method comprises culturing the human foregut endoderm cells with an inhibitor of protein methyltransferase DOT1L.

18. The method of claim 17, wherein the inhibitor of protein methyltransferase DOT1L is EPZ-5676.

19. The method of claim 2, wherein the method comprises culturing the cells in a suspension culture.

20. The method of claim 2, wherein the method comprises culturing the cells at the air-liquid interface.

* * * * *